United States Patent
Sasaki et al.

(10) Patent No.: US 8,314,088 B2
(45) Date of Patent: Nov. 20, 2012

(54) PYRAZINOOXAZEPINE DERIVATIVES

(75) Inventors: Shigekazu Sasaki, Osaka (JP); Tomokazu Kusumoto, Osaka (JP)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

(21) Appl. No.: 13/192,845

(22) Filed: Jul. 28, 2011

(65) Prior Publication Data

US 2011/0282054 A1    Nov. 17, 2011

Related U.S. Application Data

(62) Division of application No. 12/814,692, filed on Jun. 14, 2010.

(30) Foreign Application Priority Data

Jun. 15, 2009  (JP) ................. 2009-142673

(51) Int. Cl.
*A61P 13/00* (2006.01)
*A61K 31/55* (2006.01)
*C07D 498/02* (2006.01)

(52) U.S. Cl. ..................... 514/211.1; 540/552

(58) Field of Classification Search ............ 540/552; 514/211.1
See application file for complete search history.

(56) References Cited

U.S. PATENT DOCUMENTS

| | | |
|---|---|---|
| 2006/0199795 A1 | 9/2006 | Itoh et al. |
| 2007/0142357 A1 | 6/2007 | Smith et al. |
| 2008/0045502 A1 | 2/2008 | Wolgast et al. |
| 2008/0305162 A1 | 12/2008 | Lluel et al. |
| 2009/0062253 A1 | 3/2009 | Gahman et al. |
| 2009/0131402 A1 | 5/2009 | Shirai et al. |
| 2010/0087418 A1 | 4/2010 | Shirai et al. |
| 2010/0173894 A1 | 7/2010 | Brian et al. |

FOREIGN PATENT DOCUMENTS

| | | |
|---|---|---|
| EP | 2018863 | * 1/2009 |
| EP | 2 213 675 | 8/2010 |
| JP | 2006-56881 | 3/2006 |
| WO | 02/08178 | 1/2002 |
| WO | 02/40457 | 5/2002 |
| WO | 02/083863 | 10/2002 |
| WO | 03/097636 | 11/2003 |
| WO | 04/000829 | 12/2003 |
| WO | 04/000830 | 12/2003 |
| WO | 2004/067008 | 8/2004 |
| WO | 2004/096196 | 11/2004 |
| WO | 2007/074291 | 7/2007 |
| WO | 2007/132841 | 11/2007 |
| WO | 2008/108445 | 9/2008 |
| WO | 2009/032754 | 3/2009 |
| WO | 2009/063992 | 5/2009 |
| WO | 2009/063993 | 5/2009 |

OTHER PUBLICATIONS

International Search Report corresponding to PCT/JP2010/060408, Aug. 24, 2010.

* cited by examiner

*Primary Examiner* — Brenda Coleman
(74) *Attorney, Agent, or Firm* — Wenderoth, Lind & Ponack, L.L.P.

(57) ABSTRACT

Provided is a compound having a serotonin 5-$HT_{2C}$ receptor activating action.

A compound represented by the formula ($I_0$):

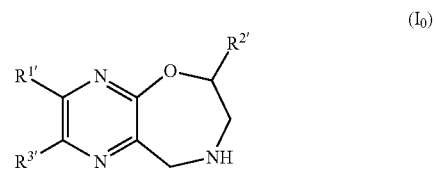

wherein each symbol is as defined in the specification, or a salt thereof.

2 Claims, No Drawings

PYRAZINOOXAZEPINE DERIVATIVES

This is a divisional of Ser No. 12/814,692, filed Jun. 14, 2010.

TECHNICAL FIELD OF THE INVENTION

The present invention relates to a pyrazinooxazepine derivative having a superior serotonin 5-$HT_{2C}$ receptor activating action and useful as an agent for the prophylaxis or treatment of a lower urinary tract symptom, obesity and/or organ prolapse etc., and the like.

BACKGROUND OF THE INVENTION

Serotonin 5-$HT_{2C}$ receptor is one of the receptors of the biological transmitter serotonin, which is distributed mainly in the central nervous system and controls many physiological functions in vivo. A representative example is the control of appetite. It has been demonstrated in a study using rodents that stimulation of the central serotonin 5-$HT_{2C}$ receptor decreases eating behavior, resulting in decreased body weight. It has also been reported that, in human as well, administration of a serotonin 5-$HT_{2C}$ receptor activator suppresses appetite and decreases body weight (see non-patent document 1). In addition, it has been demonstrated in a rat test using a serotonin 5-$HT_{2C}$ receptor activator that stimulation of the central serotonin 5-$HT_{2C}$ receptor suppresses depression-related behaviors (see non-patent document 2), and has also been reported to be effective for many central nervous diseases such as anxiety etc. (see non-patent document 3). The serotonin 5-$HT_{2C}$ receptor is also highly expressed in the parasympathetic nucleus and motor neurons in the sacral spinal cord, and is considered to control the peripheral nervous functions (see non-patent document 4). It has been reported that when a serotonin 5-$HT_{2C}$ receptor activator is administered to rats, penile erection is induced (see non-patent document 5), and urethral resistance is increased (see patent document 1); all these actions are attributed to stimulation of the serotonin 5-$HT_{2C}$ receptor in the sacral spinal cord. For serotonin 5-$HT_{2C}$ receptor activators, many clinical applications are likely, with particular expectations for anti-obesity drugs, anti-depressants, anti-anxiety drugs, therapeutic drugs for male erectile dysfunction, and therapeutic drugs for stress urinary incontinence and the like.

In addition, a serotonin 5-$HT_{2C}$ receptor activator is useful as a drug for the prophylaxis or treatment of diseases caused by prolapse of organ from the normal position due to weakening of pelvic floor muscles, for example, organ prolapse (e.g., pelvic organ prolapse, genital prolapse, uterine prolapse, bladder prolapse, rectal prolapse, urethral prolapse, urethral hypermobility, enteroceles, rectoceles, cystoceles, laceration of perineal body, pelvic floor hernia etc.) (see, for example, patent document 2).

"Pelvic organ prolapse" is a disease wherein the anterior wall of the vagina, the posterior wall of the vagina, the uterus, the vaginal stump after hysterectomy or the urinary bladder descends and protrudes beyond the vaginal orifice, and further, rectal prolapse is characterized by the symptom of descent and protrusion from the anal area of the rectal. In addition, cystoceles and enteroceles are diseases wherein bladder and small intestine descend and protrude beyond the vaginal orifice (see, for example, non-patent document 6 and non-patent document 7). Such descent becomes conspicuous when abdominal pressure rises transiently as a result of straining or bearing a heavy load and the like. These diseases are prevalent in females, with childbirth, aging, and obesity being known as risk factors, and one of suggested causes thereof is the weakening of the pelvic floor muscles, fascias and perivisceral connective tissue that support pelvic organs including the bladder and the like. The pelvic floor muscles are skeletal muscles that unite with the pelvis in a hammock-like way, serving constantly to maintain some contraction and support the organs in the pelvis from below. In pelvic organ prolapse, rectal prolapse, cystoceles and enteroceles, organ weights reportedly become unendurable because of the weakening of these pelvic floor muscles, resulting in the descent of the pelvic organs and the rectum (see, for example, non-patent document 6 and non-patent document 7); it is thought that when abdominal pressure rises particularly, the increased pressure becomes unendurable and the protrusion becomes more conspicuous. On the other hand, it has been reported that when abdominal pressure rises, the urinary bladder is compressed, reflex via the urinary bladder-spinal cord-pelvic floor muscles and the urethra causes the pelvic floor muscles and the urethral sphincter to contract to increase urethral internal pressure, whereby urinary incontinence is prevented (see, for example, non-patent document 8). Similarly, upon a rise in abdominal pressure, the pelvic floor muscles contract reflexly to prevent not only urinary incontinence, but also the descent of the pelvic organs including bladder, small intestine (see, for example, patent document 2). When there is a disorder in this reflex pathway or the pelvic floor muscles, sufficient contraction of the pelvic floor muscles cannot be obtained and support for the pelvic organs including bladder, small intestine becomes inadequate. Organ prolapse is a disease wherein the pelvic floor organs (urinary tract, bladder, uterus, small intestine, rectal and the like) and the like protrude from the vaginal orifice or rectal orifice to the outside due to the insufficient contractile strength of the pelvic floor muscles. Organ prolapse includes the forms of rectal prolapse, uterine prolapse, urethral prolapse, cystoceles, enteroceles and the like depending on the kind of the protruded organ.

A condensed heterocyclic compound having a serotonin 5-$HT_{2C}$ receptor activating action is known (see, for example, patent documents 3 and 4). In addition, it is known that compounds that bind to the serotonin 5-$HT_{2C}$ receptor are useful in the treatment of stress urinary incontinence and the like (e.g., see patent documents 5-9).

Moreover, condensed heterocyclic compounds such as benzodiazepine compounds, pyridooxazepine compounds and the like are also known (see, for example, patent documents 10 and 11).

PRIOR ART

[Patent Documents]
patent document 1: WO04/096196
patent document 2: WO07/132,841
patent document 3: WO02/040457
patent document 4: WO08/108,445
patent document 5: WO02/083863
patent document 6: WO03/097636
patent document 7: WO04/000829
patent document 8: WO04/000830
patent document 9: WO02/008178
patent document 10: WO04/067008
patent document 11: JP-A-2006-056881
[Non-Patent Documents]
non-patent document 1: Expert Opinion on Investigational Drugs, 2006, vol. 15, p. 257-266
non-patent document 2: J. Pharmacol. Exp. Ther., 1998, vol. 286, p. 913-924 non-patent document 3: Pharmacology Biochemistry Behavior, 2002, vol. 71, p. 533-554 non-patent document 4: Neuroscience, 1999, vol. 92, p. 1523-1537 non-patent document 5: Eur. J. Pharmacol., 2004, vol. 483, p. 37-43 non-patent document 6: Lancet, 2007, vol. 369, p. 1027-38 non-patent document 7: European Urology, 2007, vol. 51, p. 884-886 non-patent document 8: American Journal of Physiology Renal Physiology, 2004, vol. 287, p. F434-441

DISCLOSURE OF THE INVENTION

Problems to be Solved by the Invention

There is a demand on the development of a compound having a serotonin 5-$HT_{2C}$ receptor activating action, which is useful as an agent for the prophylaxis or treatment of lower urinary tract symptom, obesity and/or organ prolapse and the like, and has superior properties in terms of receptor selectivity, efficacy, duration of action, specificity, lower toxicity and the like.

The present invention aims to provide a pyrazinooxazepine derivative having a serotonin 5-$HT_{2C}$ receptor activating action and the like, which has a chemical structure different from that of known compounds (including the aforementioned compounds), and an agent containing the pyrazinooxazepine derivative for the prophylaxis or treatment of diseases such as a lower urinary tract symptom, obesity and/or organ prolapse and the like.

Means of Solving the Problems

The present inventors had conducted intensive studies in an attempt to solve the above-mentioned problems, and found that a compound represented by the following formula ($I_0$) or a salt thereof has a superior serotonin 5-$HT_{2C}$ receptor activating action, and made further studies, which resulted in the completion of the present invention.

Accordingly, the present invention relates to

[1] a compound represented by the formula ($I_0$)

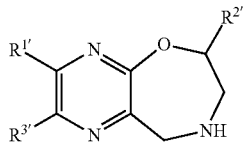

($I_0$)

wherein $R^{1'}$ is (1) a morpholinyl group optionally substituted by $C_{1-6}$ alkyl group(s), (2) a piperidyl group optionally substituted by $C_{1-6}$ alkyl group(s), (3) a pyrrolidinyl group optionally substituted by $C_{1-6}$ alkyl group(s) optionally substituted by $C_{1-6}$ alkoxy group(s), (4) a pyrrolyl group optionally substituted by $C_{1-6}$ alkyl group(s), (5) an imidazolyl group optionally substituted by $C_{1-6}$ alkyl group(s), (6) an amino group optionally substituted by 1 or 2 substituents selected from (a) a $C_{1-6}$ alkyl group optionally substituted by substituent(s) selected from a $C_{3-6}$ cycloalkyl group and a phenyl group, and (b) a $C_{3-6}$ cycloalkyl group, (7) a $C_{1-6}$ alkylsulfanyl group, (8) a $C_{1-6}$ alkoxy group optionally substituted by $C_{3-6}$ cycloalkyl group(s), (9) a $C_{3-6}$ cycloalkyl group, or

(10) a $C_{3-6}$ cycloalkenyl group;

$R^{2'}$ is a hydrogen atom or a $C_{1-6}$ alkyl group optionally substituted by $C_{1-6}$ alkoxy group(s); and $R^{3'}$ is a hydrogen atom, a halogen atom or a $C_{1-6}$ alkyl group, or a salt thereof [hereinafter to be sometimes referred to as compound ($I_0$)];

[2] the compound of the above-mentioned [1], wherein $R^{1'}$ is (1) a morpholinyl group optionally substituted by $C_{1-6}$ alkyl group(s), (2) a piperidyl group substituted by $C_{1-6}$ alkyl group(s), (3) a pyrrolidinyl group substituted by $C_{1-6}$ alkyl group(s) optionally substituted by $C_{1-6}$ alkoxy group(s), (4) a pyrrolyl group substituted by $C_{1-6}$ alkyl group(s), (5) an imidazolyl group substituted by $C_{1-6}$ alkyl group(s), (6) an amino group optionally substituted by 1 or 2 substituents selected from (a) a $C_{1-6}$ alkyl group optionally substituted by substituent(s) selected from a $C_{3-6}$ cycloalkyl group and a phenyl group, and (b) a $C_{3-6}$ cycloalkyl group, (7) a $C_{1-6}$ alkylsulfanyl group, (8) a $C_{1-6}$ alkoxy group optionally substituted by $C_{3-6}$ cycloalkyl group(s), (9) a $C_{3-6}$ cycloalkyl group, or

(10) a $C_{3-6}$ cycloalkenyl group, or a salt thereof;

[3] a compound represented by the formula (I)

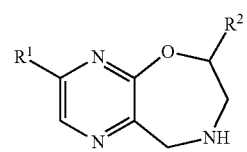

(I)

wherein $R^1$ is a morpholino group optionally substituted by $C_{1-6}$ alkyl group(s), a di($C_{1-6}$ alkyl)amino group, a $C_{1-6}$ alkoxy group optionally substituted by $C_{3-6}$ cycloalkyl group(s), a $C_{3-6}$ cycloalkyl group or a $C_{3-6}$ cycloalkenyl group; and $R^2$ is a hydrogen atom or a $C_{1-6}$ alkyl group, or a salt thereof [hereinafter to be sometimes referred to as compound (I)];

[4] the compound of the above-mentioned [3], wherein $R^1$ is a morpholino group optionally substituted by $C_{1-6}$ alkyl group(s), a di($C_{1-6}$ alkyl) amino group, a $C_{1-6}$ alkoxy group or a $C_{3-6}$ cycloalkyl group, or a salt thereof;

[5] the compound of the above-mentioned [3], wherein $R^1$ is a morpholino group optionally substituted by substituent(s) selected from a methyl group and an ethyl group, an N-methyl-N-(1-methylethyl)amino group, an isopropoxy group or a cyclopropyl group; and $R^2$ is a hydrogen atom or a methyl group, or a salt thereof;

[6] 3-(1-methylethoxy)-6,7,8,9-tetrahydropyrazino[2,3-f][1,4]oxazepine or a salt thereof;

[7] 3-(3-methylmorpholin-4-yl)-6,7,8,9-tetrahydropyrazino[2,3-f][1,4]oxazepine or a salt thereof;

[8] 6-methyl-3-(morpholin-4-yl)-6,7,8,9-tetrahydropyrazino[2,3-f][1,4]oxazepine or a salt thereof;

[9] 6-methyl-3-(3-methylmorpholin-4-yl)-6,7,8,9-tetrahydropyrazino[2,3-f][1,4]oxazepine or a salt thereof;
[10] N-methyl-N-(1-methylethyl)-6,7,8,9-tetrahydropyrazino[2,3-f][1,4]oxazepin-3-amine or a salt thereof;
[11] 3-(3-ethylmorpholin-4-yl)-6,7,8,9-tetrahydropyrazino[2,3-f][1,4]oxazepine or a salt thereof;
[12] 3-cyclopropyl-6,7,8,9-tetrahydropyrazino[2,3-f][1,4]oxazepine or a salt thereof;
[13] 3-(2-methylpiperidin-1-yl)-6,7,8,9-tetrahydropyrazino[2,3-f][1,4]oxazepine or a salt thereof;
[14] 3-(2-methylpyrrolidin-1-yl)-6,7,8,9-tetrahydropyrazino[2,3-f][1,4]oxazepine or a salt thereof;
[15] a prodrug of the compound of any one of the above-mentioned [1]-[14], or a salt thereof;
[16] a medicament comprising the compound of any one of the above-mentioned [1]-[14], or a salt thereof, or a prodrug thereof;
[17] the medicament of the above-mentioned [16], which is a serotonin 5-$HT_{2C}$ receptor activator;
[18] the medicament of the above-mentioned [16], which is a drug for the prophylaxis or treatment of a lower urinary tract symptom, obesity, and/or organ prolapse;
[19] a method for the prophylaxis or treatment of a lower urinary tract symptom, obesity, and/or organ prolapse in a mammal, comprising administering an effective amount of the compound of any one of the above-mentioned [1]-[14], or a salt thereof, or a prodrug thereof to the mammal;
[20] use of the compound of any one of the above-mentioned [1]-[14], or a salt thereof, or a prodrug thereof for the production of a drug for the prophylaxis or treatment of a lower urinary tract symptom, obesity and/or organ prolapse; and the like.

Effect of the Invention

Since compound ($I_0$) or a prodrug thereof has a superior serotonin 5-$HT_{2C}$ receptor activating action, it is useful as a safe drug for the prophylaxis or treatment of any serotonin 5-$HT_{2C}$-associated disease, for example, a lower urinary tract symptom, obesity and/or organ prolapse and the like.

MODE FOR CARRYING OUT THE INVENTION

The definition of each symbol in the formula ($I_0$) is explained in detail in the following.

The "$C_{1-6}$ alkyl group" in the present specification means, unless otherwise specified, a methyl group, an ethyl group, a propyl group, an isopropyl group, a butyl group, an isobutyl group, a sec-butyl group, a tert-butyl group, a pentyl group, an isopentyl group, a neopentyl group, a 1-ethylpropyl group, a hexyl group, an isohexyl group, an 1,1-dimethylbutyl group, a 2,2-dimethylbutyl group, a 3,3-dimethylbutyl group, a 2-ethylbutyl group and the like.

The "$C_{1-6}$ alkoxy group" in the present specification means, unless otherwise specified, a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a 1-ethylpropyloxy group, a hexyloxy group, an isohexyloxy group, a 1,1-dimethylbutyloxy group, a 2,2-dimethylbutyloxy group, a 3,3-dimethylbutyloxy group, a 2-ethylbutyloxy group and the like.

The "$C_{3-6}$ cycloalkyl group" in the present specification means, unless otherwise specified, a cyclopropyl group, a cyclobutyl group, a cyclopentyl group, a Cyclohexyl group and and the like.

The "morpholinyl group" of the "morpholinyl group optionally substituted by $C_{1-6}$ alkyl group(s)" for $R^{1'}$ may be substituted by any number of substituents selected from the above-mentioned "$C_{1-6}$ alkyl group". The number of the "$C_{1-6}$ alkyl group" is not limited as long as the substitution is possible, and is preferably 1 to 3 (More preferably 1 or 2, particularly preferably 1). When two or more "$C_{1-6}$ alkyl groups" are present, they may be the same or different.

As the "morpholinyl group optionally substituted by $C_{1-6}$ alkyl group(s)", a morpholinyl group optionally substituted by 1 to 3 (preferably 1 or 2, more preferably 1) alkyl groups is preferable, a morpholinyl group (preferably, a morpholino group) optionally substituted by 1 or 2 (preferably 1) $C_{1-4}$ alkyl groups (preferably, a methyl group, an ethyl group) is more preferable, and a morpholino group, a methylmorpholino group (preferably, a 3-methylmorpholino group) and an ethylmorpholino group (preferably, a 3-ethylmorpholino group) are more preferable.

In other embodiments, as the "morpholinyl group optionally substituted by $C_{1-6}$ alkyl group(s)", a morpholino group optionally substituted by $C_{1-6}$ alkyl group(s) is preferable.

The "piperidyl group" of the "piperidyl group optionally substituted by $C_{1-6}$ alkyl group(s)" for $R^{1'}$ may be substituted by any number of substituents selected from the above-mentioned "$C_{1-6}$ alkyl group". The number of the "$C_{1-6}$ alkyl group" is not limited as long as the substitution is possible, and is preferably 1 to 3 (More preferably 1 or 2, particularly preferably 1). When two or more "$C_{1-6}$ alkyl groups" are present, they may be the same or different.

As the "piperidyl group optionally substituted by $C_{1-6}$ alkyl group(s)", a piperidyl group optionally substituted by 1 to 3 (preferably 1 or 2, more preferably 1) $C_{1-6}$ alkyl groups is preferable, a piperidyl group (preferably, a piperidino group) optionally substituted by 1 or 2 (preferably 1) $C_{1-4}$ alkyl groups (preferably, methyl groups) is more preferable, and methylpiperidino (preferably, 2-methylpiperidino) is still more preferable.

In other embodiments, as the "piperidyl group optionally substituted by $C_{1-6}$ alkyl group(s)", a piperidyl group substituted by $C_{1-6}$ alkyl group(s) is preferable, a piperidyl group substituted by 1 to 3 (preferably 1 or 2, more preferably 1) $C_{1-6}$ alkyl groups is more preferable, and a piperidyl group (preferably, a piperidino group) substituted by 1 or 2 (preferably 1) $C_{1-4}$ alkyl groups (preferably, methyl groups) is more preferable.

The "pyrrolidinyl group" of the "pyrrolidinyl group optionally substituted by $C_{1-6}$ alkyl group(s) optionally substituted by $C_{1-6}$ alkoxy group(s)" for $R^{1'}$ may be substituted by any number of substituents selected from the "$C_{1-6}$ alkyl group(s) optionally substituted by $C_{1-6}$ alkoxy group(s)". Here, the "$C_{1-6}$ alkyl group(s) optionally substituted by $C_{1-6}$ alkoxy group(s)" is the above-mentioned "$C_{1-6}$ alkyl group" optionally substituted by any number (preferably, 1 to 3, more preferably 1 or 2, more preferably 1) of substituents selected from the above-mentioned "$C_{1-6}$ alkoxy group". When two or more "$C_{1-6}$ alkoxy groups" are present, they may be the same or different.

The number of the "$C_{1-6}$ alkyl group(s) optionally substituted by $C_{1-6}$ alkoxy group(s)" that the "pyrrolidinyl group" may have is not limited as long as the substitution is possible, and is preferably 1 to 3 (More preferably 1 or 2, particularly preferably 1). When two or more "$C_{1-6}$ alkyl groups optionally substituted by $C_{1-6}$ alkoxy group(s)" are present, they may be the same or different.

As the "pyrrolidinyl group optionally substituted by $C_{1-6}$ alkyl group(s) optionally substituted by $C_{1-6}$ alkoxy group(s)", a pyrrolidinyl group optionally substituted by 1 to 3 (preferably 1 or 2, more preferably 1) "$C_{1-6}$ alkyl groups optionally substituted by 1-3 (preferably 1 or 2, more preferably 1) $C_{1-6}$ alkoxy groups" is preferable, a pyrrolidinyl group (preferably, a 1-pyrrolidinyl group) optionally substituted by 1 or 2 (preferably 1) "$C_{1-4}$ alkyl groups (preferably, methyl groups) optionally substituted by 1 or 2 (preferably 1) $C_{1-4}$ alkoxy groups (preferably, methoxy groups)" is more preferable, and methylpyrrolidinyl (preferably, 2-methylpyrrolidin-1-yl) and (methoxymethyl)pyrrolidinyl (preferably, 2-(methoxymethyl)pyrrolidin-1-yl) are more preferable.

In other embodiment, as the "pyrrolidinyl group optionally substituted by $C_{1-6}$ alkyl group(s) optionally substituted by $C_{1-6}$ alkoxy group(s)", a pyrrolidinyl group substituted by $C_{1-6}$ alkyl group(s) optionally substituted by $C_{1-6}$ alkoxy group(s) is preferable, a pyrrolidinyl group substituted by 1 to 3 (preferably 1 or 2, more preferably 1) "$C_{1-6}$ alkyl groups optionally substituted by 1-3 (preferably 1 or 2, more preferably 1) $C_{1-6}$ alkoxy groups" is more preferable, and a pyrrolidinyl group (preferably, a 1-pyrrolidinyl group) substituted by 1 or 2 (preferably 1) "$C_{1-4}$ alkyl groups (preferably, methyl groups) optionally substituted by 1 or 2 (preferably 1) $C_{1-4}$ alkoxy groups (preferably, methoxy groups)" is more preferable.

The "pyrrolyl group" of the "pyrrolyl group optionally substituted by $C_{1-6}$ alkyl group(s)" for $R^{1'}$ may be substituted by any number of substituents selected from the above-mentioned "$C_{1-6}$ alkyl group". The number of the "$C_{1-6}$ alkyl group" is not limited as long as the substitution is possible, and is preferably 1 to 3 (More preferably 1 or 2). When two or more "$C_{1-6}$ alkyl groups" are present, they may be the same or different.

As the "pyrrolyl group optionally substituted by $C_{1-6}$ alkyl group(s)", a pyrrolyl group optionally substituted by 1-3 (preferably 1 or 2) $C_{1-6}$ alkyl groups is preferable, a pyrrolyl group (preferably, a 1-pyrrolyl group) optionally substituted by 1 or 2 $C_{1-4}$ alkyl groups (preferably, methyl groups) is more preferable, and dimethylpyrrolyl (preferably, 2,5-dimethylpyrrol-1-yl) is more preferable.

In other embodiments, as the "pyrrolyl group optionally substituted by $C_{1-6}$ alkyl group(s)", a pyrrolyl group substituted by $C_{1-6}$ alkyl group(s) is preferable, a pyrrolyl group substituted by 1 to 3 (preferably 1 or 2) $C_{1-6}$ alkyl groups is more preferable, and a pyrrolyl group (preferably, a 1-pyrrolyl group) substituted by 1 or 2 $C_{1-4}$ alkyl groups (preferably, methyl groups) is still more preferable.

The "imidazolyl group" of the "imidazolyl group optionally substituted by $C_{1-6}$ alkyl group(s)" for $R^{1'}$ may be substituted by any number of substituents selected from the above-mentioned "$C_{1-6}$ alkyl group". The number of the "$C_{1-6}$ alkyl group" is not limited as long as the substitution is possible, and is preferably 1 to 3 (More preferably 1 or 2, particularly preferably 1). When two or more "$C_{1-6}$ alkyl groups" are present, they may be the same or different.

As the "imidazolyl group optionally substituted by $C_{1-6}$ alkyl group(s)", an imidazolyl group optionally substituted by 1-3 (preferably 1 or 2, more preferably 1) $C_{1-6}$ alkyl groups is preferable, an imidazolyl group (preferably, a 1-imidazolyl group) optionally substituted by 1 or 2 (preferably 1) $C_{1-9}$ alkyl groups (preferably, methyl groups) is more preferable, and methylimidazolyl (preferably, 2-methylimidazol-1-yl) is still more preferable.

In other embodiment, as the "imidazolyl group optionally substituted by $C_{1-6}$ alkyl group(s)", an imidazolyl group substituted by $C_{1-6}$ alkyl group(s) is preferable, an imidazolyl group substituted by 1-3 (preferably 1 or 2, more preferably 1) $C_{1-6}$ alkyl groups is more preferable, and an imidazolyl group (preferably, a 1-imidazolyl group) substituted by 1 or 2 (preferably 1) $C_{1-4}$ alkyl groups (preferably, methyl groups) is more preferable.

The "amino group" of the "amino group optionally substituted by 1 or 2 substituents selected from (a) $C_{1-6}$ alkyl group optionally substituted by substituent(s) selected from $C_{3-6}$ cycloalkyl group and phenyl group, and (b) $C_{3-6}$ cycloalkyl group" for $R^{1'}$ may be substituted by 1 or 2 substituents selected from (a) the above-mentioned "$C_{1-6}$ alkyl group" optionally substituted by any number (preferably, 1 to 3, more preferably 1 or 2, more preferably 1) of substituents selected from the above-mentioned "$C_{3-6}$ cycloalkyl group" and a phenyl group, and (b) the above-mentioned "$C_{3-6}$ cycloalkyl group". When two substituents are present, they may be the same or different.

As the "amino group optionally substituted by 1 or 2 substituents selected from (a) a $C_{1-6}$ alkyl group optionally substituted by substituent(s) selected from a $C_{3-6}$ cycloalkyl group and a phenyl group, and (b) a $C_{3-6}$ cycloalkyl group", an amino group optionally substituted by 1 or 2 substituents selected from (a) a $C_{1-6}$ alkyl group optionally substituted by 1 to 3 (preferably 1 or 2, more preferably 1) substituents selected from a $C_{3-6}$ cycloalkyl group and a phenyl group, and (b) a $C_{3-6}$ cycloalkyl group is preferable, an amino group optionally substituted by 1 or 2 substituents selected from (a) a $C_{1-4}$ alkyl group (preferably, a methyl group, an ethyl group, a propyl group, an isopropyl group, a sec-butyl group) optionally substituted by 1 to 3 (preferably 1 or 2, more preferably 1) substituents selected from a $C_{3-6}$ cycloalkyl group (preferably, a cyclopropyl group) and a phenyl group, and (b) a $C_{3-6}$ cycloalkyl group (preferably, a cyclobutyl group) is more preferable, and an amino group, an N-(1-methylethyl)amino group, an N-methyl-N-propylamino group, an N-methyl-N-(1-methylethyl)amino group, an N-methyl-N-(1-methylpropyl)amino group, an N-ethyl-N-(1-methylethyl)amino group, an N-cyclopropylmethyl-N-methylamino group, an N-(1-methylethyl)-N-(phenylmethyl)amino group and an N-cyclobutyl-N-methylamino group are more preferable.

In other embodiment, as the "amino group optionally substituted by 1 or 2 substituents selected from (a) a $C_{1-6}$ alkyl group optionally substituted by substituent(s) selected from a $C_{3-6}$ cycloalkyl group and a phenyl group, and (b) a $C_{3-6}$ cycloalkyl group", the "di($C_{1-6}$ alkyl)amino group" is preferable.

Examples of the "$C_{1-6}$ alkylsulfanyl group" for $R^{1'}$ include a methylsulfanyl group, an ethylsulfanyl group, a propylsulfanyl group, an isopropylsulfanyl group, a butylsulfanyl group, an isobutylsulfanyl group, a sec-butylsulfanyl group, a tert-butylsulfanyl group, a pentylsulfanyl group, an isopentylsulfanyl group, a neopentylsulfanyl group, a 1-ethylpropylsulfanyl group, a hexylsulfanyl group, an isohexylsulfanyl group, an 1,1-dimethylbutylsulfanyl group, a 2,2-dimethylbutylsulfanyl group, a 3,3-dimethylbutylsulfanyl group, a 2-ethylbutylsulfanyl group and the like.

As the "$C_{1-6}$ alkylsulfanyl group", a $C_{1-4}$ alkylsulfanyl group is preferable, and an isopropylsulfanyl group is more preferable.

The "$C_{1-6}$ alkoxy group" of the "$C_{1-6}$ alkoxy group optionally substituted by $C_{3-6}$ cycloalkyl group(s)" for $R^{1'}$ may be substituted by any number of substituents selected from the above-mentioned "$C_{3-6}$ cycloalkyl group". The number of the "$C_{3-6}$ cycloalkyl group" is not limited as long as the substitution is possible, and is preferably 1 to 3 (More preferably 1 or 2, particularly preferably 1). When two or more "$C_{3-6}$ cycloalkyl groups" are present, they may be the same or different.

As the "$C_{1-6}$ alkoxy group optionally substituted by $C_{3-6}$ cycloalkyl group(s)", a $C_{1-6}$ alkoxy group optionally substituted by 1-3 (More preferably 1 or 2, particularly preferably 1) $C_{3-6}$ cycloalkyl groups is preferable, a $C_{1-4}$ alkoxy group (preferably, an ethoxy group, an isopropoxy group) optionally substituted by 1 or 2 (preferably 1) $C_{3-6}$ cycloalkyl groups (preferably, cyclopropyl groups) is more preferable, and a cyclopropylethoxy group (preferably, 1-cyclopropylethoxy group) and an isopropoxy group are more preferable.

As the "$C_{3-6}$ cycloalkyl group" for $R^{1'}$, a cyclopropyl group and a cyclopentyl group are preferable.

Examples of the "$C_{3-6}$ cycloalkenyl group" for $R^{1'}$ include a cyclopropenyl group (e.g., a 1-cyclopropen-1-yl group, a 2-cyclopropen-1-yl group), a cyclobutenyl group (e.g., a 1-cyclobuten-1-yl group, a 2-cyclobuten-1-yl group), a cyclopentenyl group (e.g., a 1-cyclopenten-1-yl group, a 2-cyclopenten-1-yl group, a 3-cyclopenten-1-yl group), a cyclohexenyl group (e.g., a 1-cyclohexen-1-yl group, a 2-cyclohexen-1-yl group, a 3-cyclohexen-1-yl group) and the like.

As the "$C_{3-6}$ cycloalkenyl group", a cyclopentenyl group is preferable, and a 1-cyclopenten-1-yl group is more preferable.

$R^{1'}$ is preferably (1) a morpholinyl group optionally substituted by 1-3 (preferably 1 or 2, more preferably 1) $C_{1-6}$ alkyl groups,
(2) a piperidyl group optionally substituted by 1-3 (preferably 1 or 2, more preferably 1) $C_{1-6}$ alkyl groups,
(3) a pyrrolidinyl group optionally substituted by 1-3 (preferably 1 or 2, more preferably 1) "$C_{1-6}$ alkyl groups optionally substituted by 1-3 (preferably 1 or 2, more preferably 1) $C_{1-6}$ alkoxy groups",
(4) a pyrrolyl group optionally substituted by 1-3 (preferably 1 or 2) $C_{1-6}$ alkyl groups,
(5) an imidazolyl group optionally substituted by 1-3 (preferably 1 or 2, more preferably 1) $C_{1-6}$ alkyl groups,
(6) an amino group optionally substituted by 1 or 2 substituents selected from
  (a) a $C_{1-6}$ alkyl group optionally substituted by 1-3 (preferably 1 or 2, more preferably 1) substituents selected from a $C_{3-6}$ cycloalkyl group and a phenyl group, and
  (b) a $C_{3-6}$ cycloalkyl group,
(7) a $C_{1-6}$ alkylsulfanyl group,
(8) a $C_{1-6}$ alkoxy group optionally substituted by 1-3 (preferably 1 or 2, more preferably 1) $C_{3-6}$ cycloalkyl groups,
(9) a $C_{3-6}$ cycloalkyl group, or
(10) a $C_{3-6}$ cycloalkenyl group, more preferably, (1) a morpholinyl group (preferably, a morpholino group) optionally substituted by 1 or 2 (preferably 1) $C_{1-4}$ alkyl groups (preferably, methyl group, ethyl group),
(2) a piperidyl group (preferably, a piperidino group) optionally substituted by 1 or 2 (preferably 1) $C_{1-4}$ alkyl groups (preferably, a methyl group),
(3) a pyrrolidinyl group (preferably, a 1-pyrrolidinyl group) optionally substituted by 1 or 2 (preferably 1) "$C_{1-4}$ alkyl groups (preferably, a methyl group) optionally substituted by 1 or 2 (preferably 1) $C_{1-4}$ alkoxy groups (preferably, methoxy groups)",
(4) a pyrrolyl group (preferably, a 1-pyrrolyl group) optionally substituted by 1 or 2 $C_{1-4}$ alkyl groups (preferably, methyl groups),
(5) an imidazolyl group (preferably, a 1-imidazolyl group) optionally substituted by 1 or 2 (preferably 1) $C_{1-4}$ alkyl groups (preferably, methyl groups),
(6) an amino group optionally substituted by 1 or 2 substituents selected from
  (a) a $C_{1-4}$ alkyl group (preferably, a methyl group, an ethyl group, a propyl group, an isopropyl group, a sec-butyl group) optionally substituted by 1 or 2 (preferably 1) substituents selected from a $C_{3-6}$ cycloalkyl group (preferably, a cyclopropyl group) and a phenyl group, and
  (b) a $C_{3-6}$ cycloalkyl group (preferably, a cyclobutyl group),
(7) a $C_{1-4}$ alkylsulfanyl group,
(8) a $C_{1-4}$ alkoxy group (preferably, an ethoxy group, an isopropoxy group) optionally substituted by 1 or 2 (preferably 1) $C_{3-6}$ cycloalkyl groups (preferably, cyclopropyl groups),
(9) a $C_{3-6}$ cycloalkyl group, or
(10) a $C_{3-6}$ cycloalkenyl group, more preferably, (1) a morpholino group, a methylmorpholino group (preferably, a 3-methylmorpholino group) or an ethylmorpholino group (preferably, a 3-ethylmorpholino group),
(2) methylpiperidino (preferably, 2-methylpiperidino),
(3) methylpyrrolidinyl (preferably, 2-methylpyrrolidin-1-yl) or (methoxymethyl)pyrrolidinyl (preferably, 2-(methoxymethyl)pyrrolidin-1-yl),
(4) dimethylpyrrolyl (preferably, 2,5-dimethylpyrrol-1-yl),
(5) methylimidazolyl (preferably, 2-methylimidazol-1-yl),
(6) an amino group, an N-(1-methylethyl)amino group, an N-methyl-N-propylamino group, an N-methyl-N-(1-methylethyl)amino group, an N-methyl-N-(1-methylpropyl)amino group, an N-ethyl-N-(1-methylethyl)amino group, an N-cyclopropylmethyl-N-methylamino group, an N-(1-methylethyl)-N-(phenylmethyl)amino group or an N-cyclobutyl-N-methylamino group,
(7) an isopropylsulfanyl group,
(8) a cyclopropylethoxy group (preferably, a 1-cyclopropylethoxy group) or an isopropoxy group,
(9) a cyclopropyl group or a cyclopentyl group, or
(10) a cyclopentenyl group (preferably, a 1-cyclopenten-1-yl group).

In another embodiment, $R^{1'}$ is preferably (1) a morpholinyl group optionally substituted by $C_{1-6}$ alkyl group(s),
(2) a piperidyl group substituted by $C_{1-6}$ alkyl group(s),
(3) a pyrrolidinyl group substituted by $C_{1-6}$ alkyl group(s) optionally substituted by $C_{1-6}$ alkoxy group(s),
(4) a pyrrolyl group substituted by $C_{1-6}$ alkyl group(s),
(5) an imidazolyl group substituted by $C_{1-6}$ alkyl group(s),
(6) an amino group optionally substituted by 1 or 2 substituents selected from
  (a) a $C_{1-6}$ alkyl group optionally substituted by substituent(s) selected from a $C_{3-6}$ cycloalkyl group and a phenyl group, and
  (b) a $C_{3-6}$ cycloalkyl group,
(7) a $C_{1-6}$ alkylsulfanyl group,
(8) a $C_{1-6}$ alkoxy group optionally substituted by $C_{3-6}$ cycloalkyl group(s),
(9) a $C_{3-6}$ cycloalkyl group, or
(10) a $C_{3-6}$ cycloalkenyl group, more preferably, (1) a morpholinyl group optionally substituted by 1-3 (preferably 1 or 2, more preferably 1) $C_{1-6}$ alkyl groups,
(2) a piperidyl group substituted by 1-3 (preferably 1 or 2, more preferably 1) $C_{1-6}$ alkyl groups,
(3) a pyrrolidinyl group substituted by 1-3 (preferably 1 or 2, more preferably 1) "$C_{1-6}$ alkyl groups optionally substituted by 1-3 (preferably 1 or 2, more preferably 1) $C_{1-6}$ alkoxy groups",
(4) a pyrrolyl group substituted by 1-3 (preferably 1 or 2) $C_{1-6}$ alkyl groups, (5) an imidazolyl group substituted by 1-3 (preferably 1 or 2, more preferably 1) $C_{1-6}$ alkyl groups,
(6) an amino group optionally substituted by 1 or 2 substituents selected from
 (a) a $C_{1-6}$ alkyl group optionally substituted by 1-3 (preferably 1 or 2, more preferably 1) substituents selected from a $C_{3-6}$ cycloalkyl group and a phenyl group, and
 (b) a $C_{3-6}$ cycloalkyl group,
(7) a $C_{1-6}$ alkylsulfanyl group,
(8) a $C_{1-6}$ alkoxy group optionally substituted by 1 to 3 (preferably 1 or 2, more preferably 1) $C_{3-6}$ cycloalkyl groups,
(9) a $C_{3-6}$ cycloalkyl group, or
(10) a $C_{3-6}$ cycloalkenyl group,
more preferably,
(1) a morpholinyl group optionally substituted by 1 or 2 (preferably 1) $C_{1-4}$ alkyl groups (preferably, methyl groups, ethyl groups),
(2) a piperidyl group (preferably, a piperidino group) substituted by 1 or 2 (preferably 1) $C_{1-4}$ alkyl groups (preferably, methyl groups),
(3) a pyrrolidinyl group (preferably, a 1-pyrrolidinyl group) substituted by 1 or 2 (preferably 1) "$C_{1-4}$ alkyl groups (preferably, methyl groups) optionally substituted by 1 or 2 (preferably 1) $C_{1-4}$ alkoxy groups (preferably, methoxy groups)",
(4) a pyrrolyl group (preferably, a 1-pyrrolyl group) substituted by 1 or 2 $C_{1-4}$ alkyl groups (preferably, methyl groups),
(5) an imidazolyl group (preferably, a 1-imidazolyl group) substituted by 1 or 2 (preferably 1) $C_{1-4}$ alkyl groups (preferably, methyl groups),
(6) an amino group optionally substituted by 1 or 2 substituents selected from
 (a) a $C_{1-4}$ alkyl group (preferably, a methyl group, an ethyl group, a propyl group, an isopropyl group, a sec-butyl group) optionally substituted by 1 or 2 (preferably 1) substituents selected from a $C_{3-6}$ cycloalkyl group (preferably, a cyclopropyl group) and a phenyl group, and
 (b) a $C_{3-6}$ cycloalkyl group (preferably, a cyclobutyl group),
(7) a $C_{1-4}$ alkylsulfanyl group,
(8) a $C_{1-4}$ alkoxy group (preferably, an ethoxy group, an isopropoxy group) optionally substituted by 1 or 2 (preferably 1) $C_{3-6}$ cycloalkyl groups (preferably, cyclopropyl groups),
(9) a $C_{3-6}$ cycloalkyl group, or
(10) a $C_{3-6}$ cycloalkenyl group.

In addition, in another embodiment, $R^{1'}$ is preferably a morpholino group optionally substituted by $C_{1-6}$ alkyl group(s), a di($C_{1-6}$ alkyl) amino group, a $C_{1-6}$ alkoxy group optionally substituted by $C_{3-6}$ cycloalkyl group(s), a $C_{3-6}$ cycloalkyl group or a $C_{3-6}$ cycloalkenyl group.

The "$C_{1-6}$ alkyl group" of the "$C_{1-6}$ alkyl group optionally substituted by $C_{1-6}$ alkoxy group(s)" for $R^{2'}$ may be substituted by any number of substituents selected from the abovementioned "$C_{1-6}$ alkoxy group". The number of the "$C_{1-6}$ alkoxy group" is not limited as long as the substitution is possible, and is preferably 1 to 3 (More preferably 1 or 2, particularly preferably 1). When two or more "$C_{1-6}$ alkoxy groups" are present, they may be the same or different.

As the "$C_{1-6}$ alkyl group optionally substituted by $C_{1-6}$ alkoxy group(s)", a $C_{1-6}$ alkyl group optionally substituted by 1-3 (preferably 1 or 2, more preferably 1) $C_{1-6}$ alkoxy groups is preferable, a $C_{1-4}$ alkyl group (preferably, a methyl group) optionally substituted by 1 or 2 (preferably 1) $C_{1-4}$ alkoxy groups (preferably, methoxy groups) is more preferable, and a methyl group and a methoxymethyl group are more preferable.

$R^{2'}$ is preferably a hydrogen atom or a $C_{1-6}$ alkyl group optionally substituted by 1 to 3 (preferably 1 or 2, more preferably 1) $C_{1-6}$ alkoxy groups, more preferably, a hydrogen atom or a $C_{1-4}$ alkyl group (preferably, a methyl group) optionally substituted by 1 or 2 (preferably 1) $C_{1-4}$ alkoxy groups (preferably, methoxy groups), and more preferably is a hydrogen atom, a methyl group or a methoxymethyl group.

In another embodiment, $R^{2'}$ is preferably a hydrogen atom or a $C_{1-6}$ alkyl group.

$R^{3'}$ is preferably a hydrogen atom, a halogen atom (preferably, a chlorine atom, a bromine atom) or a $C_{1-4}$ alkyl group (preferably, a methyl group), more preferably a hydrogen atom.

As compound ($I_0$),
a compound wherein $R^{1'}$ is
(1) a morpholinyl group optionally substituted by 1 to 3 (preferably 1 or 2, more preferably 1) $C_{1-6}$ alkyl groups,
(2) a piperidyl group optionally substituted by 1 to 3 (preferably 1 or 2, more preferably 1) $C_{1-6}$ alkyl groups,
(3) a pyrrolidinyl group optionally substituted by 1 to 3 (preferably 1 or 2, more preferably 1) "$C_{1-6}$ alkyl groups optionally substituted by 1-3 (preferably 1 or 2, more preferably 1) $C_{1-6}$ alkoxy groups",
(4) a pyrrolyl group optionally substituted by 1 to 3 (preferably 1 or 2) $C_{1-6}$ alkyl groups,
(5) an imidazolyl group optionally substituted by 1 to 3 (preferably 1 or 2, more preferably 1) $C_{1-6}$ alkyl groups,
(6) an amino group optionally substituted by 1 or 2 substituents selected from
 (a) a $C_{1-6}$ alkyl group optionally substituted by 1 to 3 (preferably 1 or 2, more preferably 1) substituents selected from a $C_{3-6}$ cycloalkyl group and a phenyl group, and
 (b) a $C_{3-6}$ cycloalkyl group,
(7) a $C_{1-6}$ alkylsulfanyl group,
(8) a $C_{1-6}$ alkoxy group optionally substituted by 1 to 3 (preferably 1 or 2, more preferably 1) $C_{3-6}$ cycloalkyl groups,
(9) a $C_{3-6}$ cycloalkyl group, or
(10) a $C_{3-6}$ cycloalkenyl group
{preferably,
(1) a morpholinyl group (preferably, a morpholino group) optionally substituted by 1 or 2 (preferably 1) $C_{1-4}$ alkyl groups (preferably, methyl groups, ethyl groups),
(2) a piperidyl group (preferably, a piperidino group) optionally substituted by 1 or 2 (preferably 1) $C_{1-4}$ alkyl groups (preferably, methyl groups),
(3) a pyrrolidinyl group (preferably, a 1-pyrrolidinyl group) optionally substituted by 1 or 2 (preferably 1) "$C_{1-4}$ alkyl groups (preferably, methyl groups) optionally substituted by 1 or 2 (preferably 1) $C_{1-4}$ alkoxy groups (preferably, methoxy groups)",
(4) a pyrrolyl group (preferably, a 1-pyrrolyl group) optionally substituted by 1 or 2 $C_{1-4}$ alkyl groups (preferably, methyl groups),
(5) an imidazolyl group (preferably, a 1-imidazolyl group) optionally substituted by 1 or 2 (preferably 1) $C_{1-4}$ alkyl groups (preferably, methyl groups),
(6) an amino group optionally substituted by 1 or 2 substituents selected from
 (a) a $C_{1-4}$ alkyl group (preferably, a methyl group, an ethyl group, a propyl group, an isopropyl group, a sec-butyl group) optionally substituted by 1 or 2 (preferably 1) substituents selected from a $C_{3-6}$ cycloalkyl group (preferably, a cyclopropyl group) and a phenyl group, and (b) a $C_{3-6}$ cycloalkyl group (preferably, a cyclobutyl group),
(7) a $C_{1-4}$ alkylsulfanyl group,
(8) a $C_{1-4}$ alkoxy group (preferably, an ethoxy group, an isopropoxy group) optionally substituted by 1 or 2 (preferably 1) $C_{3-6}$ cycloalkyl groups (preferably, cyclopropyl groups),
(9) a $C_{3-6}$ cycloalkyl group, or
(10) a $C_{3-6}$ cycloalkenyl group
[more preferably,
(1) a morpholino group, a methylmorpholino group (preferably, a 3-methylmorpholino group) or an ethylmorpholino group (preferably, a 3-ethylmorpholino group),
(2) methylpiperidino (preferably, 2-methylpiperidino),
(3) methylpyrrolidinyl (preferably, 2-methylpyrrolidin-1-yl) or (methoxymethyl)pyrrolidinyl (preferably, 2-(methoxymethyl)pyrrolidin-1-yl),
(4) dimethylpyrrolyl (preferably, 2,5-dimethylpyrrol-1-yl),
(5) methylimidazolyl (preferably, 2-methylimidazol-1-yl),
(6) an amino group, an N-(1-methylethyl)amino group, an N-methyl-N-propylamino group, an N-methyl-N-(1-methylethyl)amino group, an N-methyl-N-(1-methylpropyl)amino group, an N-ethyl-N-(1-methylethyl)amino group, an N-cyclopropylmethyl-N-methylamino group, an N-(1-methylethyl)-N-(phenylmethyl)amino group or an N-cyclobutyl-N-methylamino group,
(7) an isopropylsulfanyl group,
(8) a cyclopropylethoxy group (preferably, a 1-cyclopropylethoxy group) or an isopropoxy group,
(9) a cyclopropyl group or a cyclopentyl group, or
(10) a cyclopentenyl group (preferably, a 1-cyclopenten-1-yl group)]},
$R^{2'}$ is a hydrogen atom or a $C_{1-6}$ alkyl group optionally substituted by 1 to 3 (preferably 1 or 2, more preferably 1) $C_{1-6}$ alkoxy groups {preferably, a hydrogen atom or a $C_{1-4}$ alkyl group (preferably, a methyl group) optionally substituted by 1 or 2 (preferably 1) $C_{1-4}$ alkoxy groups (preferably, methoxy groups) [more preferably, a hydrogen atom, a methyl group, a methoxymethyl group]}, and
$R^{3'}$ is a hydrogen atom, a halogen atom or a $C_{1-6}$ alkyl group [preferably, a hydrogen atom, a halogen atom (preferably, a chlorine atom, a bromine atom) or a $C_{1-4}$ alkyl group (preferably, a methyl group)], or a salt thereof is preferable.

In another embodiment, as compound ($I_0$),
a compound wherein $R^{1'}$ is
(1) a morpholinyl group optionally substituted by $C_{1-6}$ alkyl group(s),
(2) a piperidyl group substituted by $C_{1-6}$ alkyl group(s),
(3) a pyrrolidinyl group substituted by $C_{1-6}$ alkyl group(s) optionally substituted by $C_{1-6}$ alkoxy(s),
(4) a pyrrolyl group substituted by $C_{1-6}$ alkyl group(s),
(5) an imidazolyl group substituted by $C_{1-6}$ alkyl group(s),
(6) an amino group optionally substituted by 1 or 2 substituents selected from
   (a) a $C_{1-6}$ alkyl group optionally substituted by substituent(s) selected from a $C_{3-6}$ cycloalkyl group and a phenyl group, and
   (b) a $C_{3-6}$ cycloalkyl group,
(7) a $C_{1-6}$ alkylsulfanyl group,
(8) a $C_{1-6}$ alkoxy group optionally substituted by $C_{3-6}$ cycloalkyl group(s),
(9) a $C_{3-6}$ cycloalkyl group, or
(10) a $C_{3-6}$ cycloalkenyl group
{preferably,
(1) a morpholinyl group optionally substituted by 1-3 (preferably 1 or 2, more preferably 1) $C_{1-6}$ alkyl groups,
(2) a piperidyl group substituted by 1-3 (preferably 1 or 2, more preferably 1) $C_{1-6}$ alkyl groups,
(3) a pyrrolidinyl group substituted by 1-3 (preferably 1 or 2, more preferably 1) "$C_{1-6}$ alkyl groups optionally substituted by 1-3 (preferably 1 or 2, more preferably 1) $C_{1-6}$ alkoxy groups",
(4) a pyrrolyl group substituted by 1-3 (preferably 1 or 2) $C_{1-6}$ alkyl groups,
(5) an imidazolyl group substituted by 1-3 (preferably 1 or 2, more preferably 1) $C_{1-6}$ alkyl groups,
(6) an amino group optionally substituted by 1 or 2 substituents selected from
   (a) a $C_{1-6}$ alkyl group optionally substituted by 1-3 (preferably 1 or 2, more preferably 1) substituents selected from a $C_{3-6}$ cycloalkyl group and a phenyl group, and
   (b) a $C_{3-6}$ cycloalkyl group,
(7) a $C_{1-6}$ alkylsulfanyl group,
(8) a $C_{1-6}$ alkoxy group optionally substituted by 1-3 (preferably 1 or 2, more preferably 1) $C_{3-6}$ cycloalkyl groups,
(9) a $C_{3-6}$ cycloalkyl group, or
(10) a $C_{3-6}$ cycloalkenyl group
[more preferably,
(1) a morpholinyl group optionally substituted by 1 or 2 (preferably 1) $C_{1-4}$ alkyl groups (preferably, methyl groups, ethyl groups),
(2) a piperidyl group (preferably, a piperidino group) substituted by 1 or 2 (preferably 1) $C_{1-4}$ alkyl groups (preferably, methyl groups),
(3) a pyrrolidinyl group (preferably, a 1-pyrrolidinyl group) substituted by 1 or 2 (preferably 1) "$C_{1-4}$ alkyl groups (preferably, methyl groups) optionally substituted by 1 or 2 (preferably 1) $C_{1-4}$ alkoxy groups (preferably, methoxy groups)",
(4) a pyrrolyl group (preferably, a 1-pyrrolyl group) substituted by 1 or 2 $C_{1-4}$ alkyl groups (preferably, methyl groups),
(5) an imidazolyl group (preferably, a 1-imidazolyl group) substituted by 1 or 2 (preferably 1) $C_{1-4}$ alkyl groups (preferably, methyl groups),
(6) an amino group optionally substituted by 1 or 2 substituents selected from
   (a) a $C_{1-4}$ alkyl group (preferably, a methyl group, an ethyl group, a propyl group, an isopropyl group, a sec-butyl group) optionally substituted by 1 or 2 (preferably 1) substituents selected from a $C_{3-6}$ cycloalkyl group (preferably, a cyclopropyl group) and a phenyl group, and
   (b) a $C_{3-6}$ cycloalkyl group (preferably, a cyclobutyl group),
(7) a $C_{1-4}$ alkylsulfanyl group,
(8) a $C_{1-4}$ alkoxy group (preferably, an ethoxy group, an isopropoxy group) optionally substituted by 1 or 2 (preferably 1) $C_{3-6}$ cycloalkyl groups (preferably, cyclopropyl groups),
(9) a $C_{3-6}$ cycloalkyl group, or
(10) a $C_{3-6}$ cycloalkenyl group]},
$R^{2'}$ is a hydrogen atom or a $C_{1-6}$ alkyl group optionally substituted by 1-3 (preferably 1 or 2, more preferably 1) $C_{1-6}$ alkoxy groups {preferably, a hydrogen atom or a $C_{1-4}$ alkyl group (preferably, a methyl group) optionally substituted by 1 or 2 (preferably 1) $C_{1-4}$ alkoxy groups (preferably, methoxy groups) [more preferably, a hydrogen atom, a methyl group, a methoxymethyl group]}, and
$R^{3'}$ is a hydrogen atom, a halogen atom or a $C_{1-6}$ alkyl group [preferably, a hydrogen atom, a halogen atom (preferably, a chlorine atom, a bromine atom) or a $C_{1-4}$ alkyl group (preferably, a methyl group)], or a salt thereof is preferable.

As compound (I$_0$), compounds described in the following Examples 1-35 or salts thereof are preferable, and particularly, 3-(1-methylethoxy)-6,7,8,9-tetrahydropyrazino[2,3-f][1,4]oxazepine or a salt thereof (Example 2), 3-(3-methylmorpholin-4-yl)-6,7,8,9-tetrahydropyrazino[2,3-f][1,4]oxazepine (preferably, 3-[(3R)-3-methylmorpholin-4-yl]-6,7,8,9-tetrahydropyrazino[2,3-f][1,4]oxazepine) or a salt thereof (Example 5), 6-methyl-3-(morpholin-4-yl)-6,7,8,9-tetrahydropyrazino[2,3-f][1,4]oxazepine (preferably, (6S)-6-methyl-3-(morpholin-4-yl)-6,7,8,9-tetrahydropyrazino[2,3-f][1,4]oxazepine) or a salt thereof (Example 6), 6-methyl-3-(3-methylmorpholin-4-yl)-6,7,8,9-tetrahydropyrazino[2,3-f][1,4]oxazepine (preferably, (6S)-6-methyl-3-[(3R)-3-methylmorpholin-4-yl]-6,7,8,9-tetrahydropyrazino[2,3-f][1,4]oxazepine) or a salt thereof (Example 7), N-methyl-N-(1-methylethyl)-6,7,8,9-tetrahydropyrazino[2,3-f][1,4]oxazepin-3-amine or a salt thereof (Example 8), 3-(3-ethylmorpholin-4-yl)-6,7,8,9-tetrahydropyrazino[2,3-f][1,4]oxazepine (preferably, 3-[(3R)-3-ethylmorpholin-4-yl]-6,7,8,9-tetrahydropyrazino[2,3-f][1,4]oxazepine) or a salt thereof (Example 9), 3-cyclopropyl-6,7,8,9-tetrahydropyrazino[2,3-f][1,4]oxazepine or a salt thereof (Example 10), 3-(2-methylpiperidin-1-yl)-6,7,8,9-tetrahydropyrazino[2,3-f][1,4]oxazepine or a salt thereof (Example 12), and 3-(2-methylpyrrolidin-1-yl)-6,7,8,9-tetrahydropyrazino[2,3-f][1,4]oxazepine or a salt thereof (Example 13)
are preferable.

In another embodiment, moreover, as compound (I$_0$), compound (I) is preferable.

The definition of each symbol in the formula (I) is explained in detail in the following.

The "morpholino group" of the "morpholino group optionally substituted by C$_{1-6}$ alkyl group(s)" for R$^1$ may be substituted by any number of substituents selected from the above-mentioned "C$_{1-6}$ alkyl group". The number of the "C$_{1-6}$ alkyl group" is not limited as long as the substitution is possible, and is preferably 1 to 3 (More preferably 1 or 2, particularly preferably 1). When two or more "C$_{1-6}$ alkyl groups" are present, they may be the same or different.

As the "morpholino group optionally substituted by C$_{1-6}$ alkyl group(s)", a morpholino group optionally substituted by substituent(s) selected from a methyl group and an ethyl group is preferable, and a morpholino group, a methylmorpholino group (e.g., a 3-methylmorpholino group) and an ethylmorpholino group (e.g., a 3-ethylmorpholino group) are more preferable.

Examples of the "di (C$_{1-6}$ alkyl)amino group" for R$^1$ include an amino group di-substituted by substituents selected from the above-mentioned "C$_{1-6}$ alkyl group". Two "C$_{1-6}$ alkyl groups" may be the same or different.

As the "di (C$_{1-6}$ alkylamino group", an amino group di-substituted by the same or different C$_{1-3}$ alkyl groups (e.g., a methyl group, an ethyl group, a propyl group, an isopropyl group) is preferable, and an N-methyl-N-(1-methylethyl)amino group is more preferable.

As the "C$_{1-6}$ alkoxy group" of the "C$_{1-6}$ alkoxy group optionally substituted by C$_{3-6}$ cycloalkyl group(s)" for preferred is an ethoxy group, an isopropoxy group and the like.

The "C$_{1-6}$ alkoxy group" may be substituted by any number of substituents selected from the above-mentioned "C$_{3-6}$ cycloalkyl group". The number of the "C$_{3-6}$ cycloalkyl group" is not limited as long as the substitution is possible, preferably 1 to 3 (More preferably 1 or 2, particularly preferably 1). When two or more "C$_{3-6}$ cycloalkyl groups" are present, they may be the same or different.

As the "C$_{1-6}$ alkoxy group optionally substituted by C$_{3-6}$ cycloalkyl group(s)" for R$^1$, an ethoxy group and an isopropoxy group, which may be respectively substituted by cyclopropyl group(s), are preferable, and a 1-cyclopropylethoxy group and an isopropoxy group are more preferable.

As the "C$_{3-6}$ cycloalkyl group" for R$^1$, a cyclopropyl group and a cyclopentyl group are preferable.

Examples of the "C$_{3-6}$ cycloalkenyl group" for R$^1$ include a cyclopropenyl group (e.g., a 1-cyclopropen-1-yl group, a 2-cyclopropen-1-yl group), a cyclobutenyl group (e.g., a 1-cyclobuten-1-yl group, a 2-cyclobuten-1-yl group), a cyclopentenyl group (e.g., a 1-cyclopenten-1-yl group, a 2-cyclopenten-1-yl group, a 3-cyclopenten-1-yl group), a cyclohexenyl group (e.g., a 1-cyclohexen-1-yl group, a 2-cyclohexen-1-yl group, a 3-cyclohexen-1-yl group) and the like. A cyclopentenyl group is preferable, and a 1-cyclopenten-1-yl group is more preferable.

R$^1$ is preferably a morpholino group optionally substituted by substituent(s) selected from a methyl group and an ethyl group; an amino group di-substituted by substituents selected from a C$_{1-3}$ alkyl group (e.g., a methyl group, an ethyl group, a propyl group, an isopropyl group); an ethoxy group or an isopropoxy group, each of which is optionally substituted by cyclopropyl group(s); a cyclopropyl group; a cyclopentyl group; or a cyclopentenyl group.

R$^1$ is more preferably a morpholino group, a methylmorpholino group (preferably, a 3-methylmorpholino group), an ethylmorpholino group (preferably, a 3-ethylmorpholino group), an N-methyl-N-(1-methylethyl)amino group, a 1-cyclopropylethoxy group, an isopropoxy group, a cyclopropyl group, a cyclopentyl group or a cyclopentenyl group (preferably, a 1-cyclopenten-1-yl group).

In another embodiment, R$^1$ is preferably a morpholino group optionally substituted by C$_{1-6}$ alkyl group(s), a di (C$_{1-6}$ alkyl) amino group, a C$_{1-6}$ alkoxy group or a C$_{3-6}$ cycloalkyl group.

R$^1$ is more preferably a morpholino group optionally substituted by substituent(s) selected from a methyl group and an ethyl group, an N-methyl-N-(1-methylethyl)amino group, an isopropoxy group or a cyclopropyl group.

As the "C$_{1-6}$ alkyl group" for R$^2$, a methyl group is preferable.

R$^2$ is preferably a hydrogen atom or a methyl group.

As compound (I), a compound wherein
R$^1$ is a morpholino group optionally substituted by substituent(s) selected from a methyl group and an ethyl group; an amino group di-substituted by substituents selected from a C$_{1-3}$ alkyl group (e.g., a methyl group, an ethyl group, a propyl group, an isopropyl group); an ethoxy group or an isopropoxy group, each of which is optionally substituted by cyclopropyl group(s); a cyclopropyl group; a cyclopentyl group; a cyclopentenyl group [preferably, a morpholino group, a methylmorpholino group (preferably, a 3-methylmorpholino group), an ethylmorpholino group (preferably, a 3-ethylmorpholino group), an N-methyl-N-(1-methylethyl)amino group, a 1-cyclopropylethoxy group, an isopropoxy group, a cyclopropyl group, a cyclopentyl group, a cyclopentenyl group (preferably, a 1-cyclopenten-1-yl)]; and
R$^2$ is a hydrogen atom or a methyl group, or a salt thereof is preferable.

In another embodiment, as compound (I), a compound wherein
R$^1$ is a morpholino group optionally substituted by C$_{1-6}$ alkyl group(s), a di(C$_{1-6}$ alkyl) amino group, a C$_{1-6}$ alkoxy group or a $C_{3-6}$ cycloalkyl group [preferably, a morpholino group optionally substituted by substituent(s) selected from a methyl group and an ethyl group, an N-methyl-N-(1-methylethyl)amino group, an isopropoxy group or a cyclopropyl group]; and $R^2$ is a hydrogen atom or a methyl group, or a salt thereof is preferable.

As compound (I), compounds of the following Examples 1-11 or salts thereof are preferable, particularly, 3-(1-methylethoxy)-6,7,8,9-tetrahydropyrazino[2,3-f][1,4] oxazepine or a salt thereof (Example 2), 3-(3-methylmorpholin-4-yl)-6,7,8,9-tetrahydropyrazino[2,3-f][1,4]oxazepine (preferably, 3-[(3R)-3-methylmorpholin-4-yl]-6,7,8,9-tetrahydropyrazino[2,3-f][1,4]oxazepine) or a salt thereof (Example 5), 6-methyl-3-(morpholin-4-yl)-6,7,8,9-tetrahydropyrazino[2,3-f][1,4]oxazepine (preferably, (6S)-6-methyl-3-(morpholin-4-yl)-6,7,8,9-tetrahydropyrazino[2,3-f][1,4]oxazepine) or a salt thereof (Example 6), 6-methyl-3-(3-methylmorpholin-4-yl)-6,7,8,9-tetrahydropyrazino[2,3-f][1,4]oxazepine (preferably, (6S)-6-methyl-3-[(3R)-3-methylmorpholin-4-yl]-6,7,8,9-tetrahydropyrazino[2,3-f][1,4]oxazepine) or a salt thereof (Example 7), N-methyl-N-(1-methylethyl)-6,7,8,9-tetrahydropyrazino[2,3-f][1,4]oxazepin-3-amine or a salt thereof (Example 8), 3-(3-ethylmorpholin-4-yl)-6,7,8,9-tetrahydropyrazino[2,3-f][1,4]oxazepine (preferably, 3-[(3R)-3-ethylmorpholin-4-yl]-6,7,8,9-tetrahydropyrazino[2,3-f][1,4]oxazepine) or a salt thereof (Example 9), and 3-cyclopropyl-6,7,8,9-tetrahydropyrazino[2,3-f][1,4]oxazepine or a salt thereof (Example 10)

are preferable.

When compound ($I_0$) or (I) is a salt, examples of the salt include salt with inorganic base, ammonium salt, salt with organic base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Of these salts, pharmaceutically acceptable salts are preferable.

Compound ($I_0$) or (I) may be any of hydrate, non-hydrate, solvate and non-solvate.

A compound labeled with an isotope (e.g., $^2H$, $^3H$, $^{14}C$, $^{35}S$, $^{125}I$ etc.) and the like are also encompassed in compounds ($I_0$) and (I).

In addition, a deuterium exchange compound of compound ($I_0$) or (I) wherein $^1H$ is converted to $^2H(D)$ is also encompassed in compound ($I_0$) or (I).

The production methods of compounds ($I_0$) and (I) of the present invention are explained in the following.

In each of the following production methods, the starting material compounds and production intermediates may be used in the form of salts. Examples of such salt include those similar to the salts of the aforementioned compounds ($I_0$) and (I) and the like.

In addition, a production intermediate obtained in each of the production methods can also be used directly as a reaction mixture or as a crude product. However, it may be isolated or purified before use according to a known method such as phase transfer, concentration, solvent extraction, fractionation, liquid conversion, crystallization, recrystallization, chromatography and the like.

Moreover, when the compound of each formula is commercially available, such product can be used as is.

Compound (I) of the present invention can be produced, for example, according to the following method A, method B, method C, method D, or a method analogous thereto.

In compounds (I), a compound represented by the formula (Ia) wherein $R^1$ is a $C_{3-6}$ cycloalkyl group or a $C_{3-6}$ cycloalkenyl group, or a salt thereof (hereinafter to be sometimes referred to as compound (Ia) and the same applies to other formulas) can be produced, for example, according to method A shown below, or a method analogous thereto.

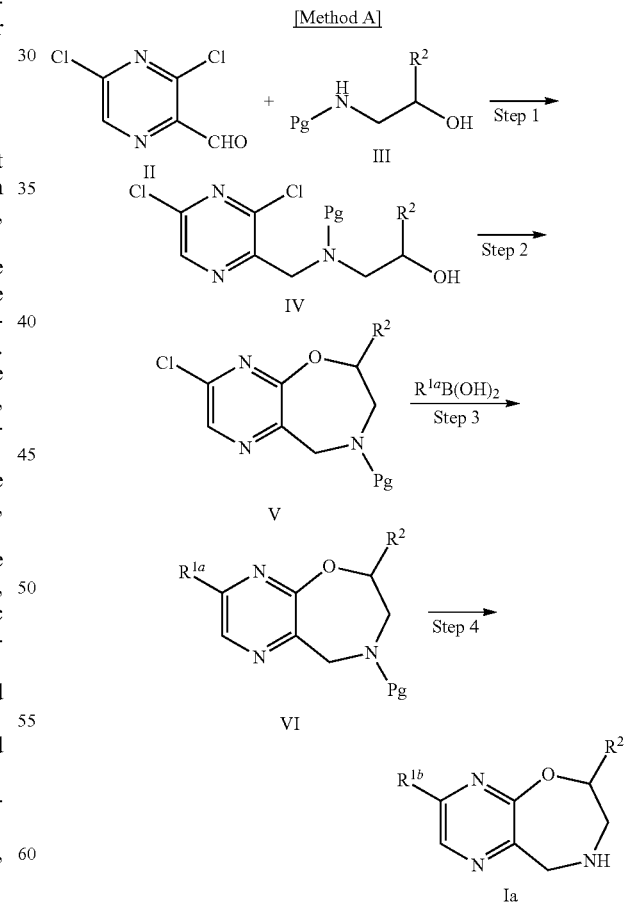

wherein Pg is a protecting group; $R^{1a}$ is a $C_{3-6}$ cycloalkyl group or a $C_{3-6}$ cycloalkenyl group; $R^{1b}$ is a $C_{3-6}$ cycloalkyl group or a $C_{3-6}$ cycloalkenyl group; and $R^2$ is as defined above.

The "protecting group" for Pg is an amino-protecting group generally used for the peptide synthesis and the like, which does not adversely influence the progress of the reaction in each step explained below (e.g., a benzyl group, a p-methoxybenzyl group) and the like, and is preferably a benzyl group.

Step 1

In this step, compound (IV) is produced by subjecting compound (II) and compound (III) to a reductive amination reaction.

While this reaction can be performed according to a method known per se [e.g., the method described in 4th ed., Jikken Kagaku Koza, vol. 14, page 370 etc.], it is generally performed in the presence of a reducing agent in, where necessary, a solvent that does not adversely influence the reaction. Compound (II) can be produced according to a method known per se [the method described in Journal, of Organometallic Chemistry, 1991, vol. 412, (No. 3), page 301] or a method analogous thereto. Compound (III) can be produced according to a method known per se [the method described in Synthetic Communications, 1994, vol. 24, (No. 10), page 1415] or a method analogous thereto.

While the amount of compound (III) to be used varies depending on the kind of solvent and other reaction conditions, it is generally about 1 mol-about 10 mol, preferably about 1 mol-about 5 mol, per 1 mol of compound (II).

Examples of the reducing agent include aluminum reagents (e.g., lithium aluminum hydride ($LiAlH_4$), diisobutylaluminum hydride (DIBAL-H), sodium bis(2-methoxyethoxy)aluminum hydride (Red-Al), alane ($AlH_3$) etc.), boron reagents (e.g., borane ($BH_3$), 9-borabicyclo[3.3.1]nonane (9-BBN), sodium borohydride ($NaBH_4$), sodium cyanoborohydride ($NaBH_3CN$), sodium triacetoxyborohydride ($NaBH(OAc)_3$) etc.) and the like. Of these, sodium borohydride, sodium cyanoborohydride and sodium triacetoxyborohydride are preferable.

While the amount of the reducing agent to be used varies depending on the kind of solvent and other reaction conditions, it is generally about 1 mol-about 10 mol, preferably about 1 mol-about 5 mol, per 1 mol of compound (II).

Examples of the solvent that does not adversely influence the reaction include alcohols (e.g., methanol, ethanol, propanol, 2-propanol, butanol, isobutanol, tert-butanol etc.), hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), carboxylic acids (e.g., acetic acid, trifluoroacetic acid etc.) and the like. These solvents may be used in a mixture at an appropriate ratio.

The reaction temperature is generally about −80° C. to about 200° C., preferably about −80° C. to about 100° C.

The reaction time is generally about 0.1 hr-about 100 hr, preferably about 0.5 hr-about 24 hr.

The thus-obtained compound (IV) can be isolated and purified by a known separation and purification means, for example, concentration, concentration under reduced pressure, solvent extraction, crystallization, recrystallization, phase transfer, chromatography and the like. Alternatively, compound (IV) may be used, without isolation, for the next reaction.

Step 2

In this step, compound (V) is produced by subjecting compound (IV) to an intramolecular ring-closing reaction. While this reaction can be performed according to a method known per se, it is generally performed in the presence of a base in, where necessary, a solvent that does not adversely influence the reaction.

Examples of the base include metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate and the like; alkali metal alkoxides such as sodium methoxide, sodium ethoxide, sodium tert-butoxide, potassium tert-butoxide etc. and the like), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.), alkali metal disilazides (e.g., lithium hexamethyl disilazide, sodium hexamethyl disilazide, potassium hexamethyl disilazide etc.) and the like. Of these, metal hydrides such as potassium hydride, sodium hydride and the like; alkali metal alkoxides such as sodium tert-butoxide, potassium tert-butoxide etc.; and the like are preferable.

While the amount of the base to be used varies depending on the kind of solvent and other reaction conditions, it is generally about 0.1 mol-about 10 mol, preferably about 0.1 mol-about 5 mol, per 1 mol of compound (IV).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.) and the like. These solvents may be used in a mixture at an appropriate ratio.

The reaction temperature is generally about −50° C. to about 200° C., preferably about −20° C. to about 100° C.

The reaction time varies depending on the kind of compound (IV), reaction temperature and the like, and is generally about 0.1 hr-about 100 hr, preferably about 0.5 hr-about 24 hr.

The thus-obtained compound (V) can be isolated and purified by a known separation and purification means, for example, concentration, concentration under reduced pressure, solvent extraction, crystallization, recrystallization, phase transfer, chromatography and the like.

Step 3

In this step, compound (VI) is produced by subjecting compound (V) and a compound represented by the formula: $R^{1a}$—$B(OH)_2$ wherein $R^{1a}$ is as defined above, or a salt thereof (hereinafter sometimes to be abbreviated as $R^{1a}$—B$(OH)_2$) to a coupling reaction.

This reaction can be performed according to a method known per se [e.g., the method described in Chemical Reviews, 1995, vol. 95, page 2457 etc.] and can be performed, for example, in the presence of a transition metal catalyst and a base, in a solvent that does not adversely influence the reaction.

The amount of $R^{1a}$—$B(OH)_2$ to be used is generally about 1 mol-about 10 mol, preferably about 1 mol-about 5 mol, per 1 mol of compound (V).

As the transition metal catalyst, palladium catalysts (e.g., palladium acetate, palladium chloride, tetrakis(triphenylphosphine)palladium etc.), nickel catalysts (e.g., nickel chloride etc.) and the like can be used. Where necessary, a ligand (e.g., triphenylphosphine, tri-tert-butylphosphine, tricyclopropylphosphine etc.) may be added, and metal oxide (e.g., copper oxide, silver oxide etc.) and the like may be used as a cocatalyst.

While the amount of the transition metal catalyst to be used varies depending on the kind of catalyst, it is generally about 0.0001 mol-about 1 mol, preferably about 0.01 mol-about 0.5 mol, per 1 mol of compound (V). The amount of the ligand to be used is generally about 0.0001 mol-about 4 mol, preferably about 0.01 mol-about 2 mol, per 1 mol of compound (V). The amount of the cocatalyst to be used is generally about 0.0001 mol-about 4 mol, preferably about 0.01 mol-about 2 mol, per 1 mol of compound (V).

Examples of the base include organic amines (e.g., trimethylamine, triethylamine, diisopropylethylamine, N-methylmorpholine, 1,8-diazabicyclo[5,4,0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), alkali metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium hexamethyl disilazide, sodium hexamethyl disilazide, potassium hexamethyl disilazide etc.) and the like. Of these, alkali metal salts such as sodium carbonate, potassium carbonate, cesium carbonate, sodium phosphate, potassium phosphate and the like; alkali metal alkoxides such as sodium tert-butoxide, potassium tert-butoxide and the like; organic amines such as triethylamine, diisopropylethylamine etc.; and the like are preferable.

The amount of the base to be used is generally about 0.1 mol-about 10 mol, preferably about 1 mol-about 5 mol, per 1 mol of compound (V).

Examples of the solvent that does not adversely influence the reaction include hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran etc.), alcohols (e.g., methanol, ethanol etc.), aprotic polar solvents (e.g., dimethylformamide, dimethyl sulfoxide, hexamethylphosphoramide etc.), water and the like. These solvents may be used in a mixture at an appropriate ratio.

The reaction temperature is generally about −10° C. to about 200° C., preferably about 0° C. to about 150° C.

The reaction time is generally about 0.5 hr-about 48 hr, preferably about 0.5 hr-about 16 hr.

The thus-obtained compound (VI) can be isolated and purified by a known separation and purification means, for example, concentration, concentration under reduced pressure, solvent extraction, crystallization, recrystallization, phase transfer, chromatography and the like. Alternatively, compound (VI) may be used, without isolation, for the next reaction.

Step 4

In this step, compound (Ia) is obtained by removing the protecting group from compound (VI).

The protecting group can be removed by a reaction known per se as a protecting group removal method or a method analogous thereto.

For example, when Pg is a benzyl group, the protecting group can be removed by a catalytic hydrogenation reaction. The catalytic hydrogenation reaction can be generally performed in a hydrogen atmosphere in the presence of a catalyst in a solvent that does not adversely influence the reaction. When $R^{1a}$ is a $C_{3-6}$ cycloalkenyl group, it is reduced to a $C_{3-6}$ cycloalkyl group by the catalytic hydrogenation reaction.

Examples of the catalyst include palladiums (e.g., palladium carbon, palladium hydroxide-carbon, palladium oxide etc.), nickels (e.g., developed nickel catalyst etc.), platinums (e.g., platinum oxide, platinum carbon etc.), rhodiums (e.g., rhodium carbon etc.) and the like.

The amount of the catalyst to be used is generally about 0.001-about 1 mol, preferably about 0.01-about 0.5 mol, per 1 mol of compound (VI).

Examples of the solvent that does not adversely influence the reaction include alcohols (e.g., methanol, ethanol, propanol, butanol etc.), hydrocarbons (e.g., benzene, toluene, xylene etc.), halogenated hydrocarbons (e.g., dichloromethane, chloroform etc.), ethers (e.g., diethyl ether, dioxane, tetrahydrofuran etc.), esters (e.g., ethyl acetate etc.), amides (e.g., N,N-dimethylformamide etc.), carboxylic acids (e.g., acetic acid etc.), water and the like. These solvents may be used in a mixture at an appropriate ratio.

The hydrogen pressure at which the reaction is carried out is generally about 1 atm-about 50 atm, preferably about 1 atm-about 10 atm.

The reaction temperature is generally about 0° C. to about 150° C., preferably about 20° C. to about 100° C.

The reaction time is generally about 5 min-about 72 hr, preferably about 0.5 hr-about 40 hr.

The thus-obtained compound (Ia) can be isolated and purified by a known separation and purification means, for example, concentration, concentration under reduced pressure, solvent extraction, crystallization, recrystallization, phase transfer, chromatography and the like.

In compounds (I), compound (Ib) wherein $R^1$ is a $C_{1-6}$ alkoxy group optionally substituted by $C_{3-6}$ cycloalkyl group(s) can be produced, for example, according to method B shown below, or a method analogous thereto.

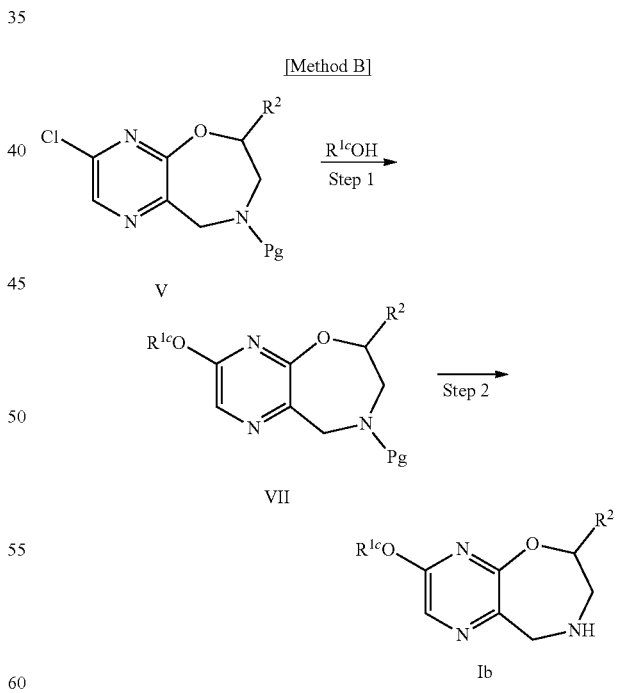

wherein $R^{1c}$ is a $C_{1-6}$ alkyl group optionally substituted by $C_{3-6}$ cycloalkyl group(s).

Step 1

In this step, compound (V) obtained in the aforementioned method A, steps 1 and 2 is converted to compound (VII) by subjecting to a substitution reaction using a compound represented by the formula: R$^{1c}$OH wherein R$^{1c}$ is as defined above (hereinafter sometimes to be abbreviated as R$^{1c}$OH).

This step can be performed according to a method known per se [e.g., the method described in J. Am. Soc. Chem., 1997, vol. 119, page 3395 etc.] and can be performed, for example, in the presence of a transition metal catalyst and a base, in a solvent that does not adversely influence the reaction.

The amount of R$^{1c}$OH to be used is generally about 1 mol-about 10 mol, preferably about 1 mol-about 5 mol, per 1 mol of compound (V).

As the transition metal catalyst, for example, palladium catalysts (e.g., palladium acetate(II), tris(dibenzylideneacetone)dipalladium(0), palladium chloride(II), tetrakis(triphenylphosphine)palladium(0) etc.) and the like can be used. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1-r-biphenyl, triphenylphosphine, tri-tert-butylphosphine and the like) may be added.

While the amount of the transition metal catalyst to be used varies depending on the kind of catalyst, it is generally about 0.0001-about 1 mol, preferably about 0.01-about 0.5 mol, per 1 mol of compound (V). The amount of the ligand to be used is generally about 0.0001-about 4 mol, preferably about 0.01-about 0.2 mol, per 1 mol of compound (V).

Examples of the base include organic amines (e.g., trimethylamine, triethylamine, diisopropylethylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithiumhexamethyl disilazide, sodium hexamethyl disilazide, potassium hexamethyl disilazide etc.) and the like. Of these, metal hydrides such as potassium hydride, sodium hydride and the like; alkali metal alkoxides such as sodium tert-butoxide, potassium tert-butoxide etc.; and the like are preferable.

The amount of the base to be used is generally about 0.1-about 10 mol, preferably about 1-about 5 mol, per 1 mol of compound (V).

Examples of the solvent that does not adversely influence the reaction include hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran etc.), aprotic polar solvents (e.g., N,N-dimethylformamide, dimethyl sulfoxide, hexamethylphosphoramide etc.) and the like. These solvents may be used in a mixture at an appropriate ratio.

The reaction temperature is generally about −10° C. to about 200° C., preferably about 0° C. to about 150° C.

The reaction time is generally about 0.5-about 48 hr, preferably about 0.5-about 16 hr.

The thus-obtained compound (VII) can be isolated and purified by a known separation and purification means, for example, concentration, concentration under reduced pressure, solvent extraction, crystallization, recrystallization, phase transfer, chromatography and the like. Alternatively, compound (VII) may be used, without isolation, for the next reaction.

Step 2

In this step, compound (Ib) is obtained by removing the protecting group from compound (VII). This step can be performed in the same manner as in the aforementioned method A, step 4.

The thus-obtained compound (Ib) can be isolated and purified by a known separation and purification means, for example, concentration, concentration under reduced pressure, solvent extraction, crystallization, recrystallization, phase transfer, chromatography and the like.

In compound (O), compound (Ic) wherein R$^1$ is a morpholino group optionally substituted by C$_{1-6}$ alkyl group(s), or compound (Ic) wherein R$^1$ is a di(C$_{1-6}$ alkyl)amino group can be produced, for example, according to method C shown below, or a method analogous thereto.

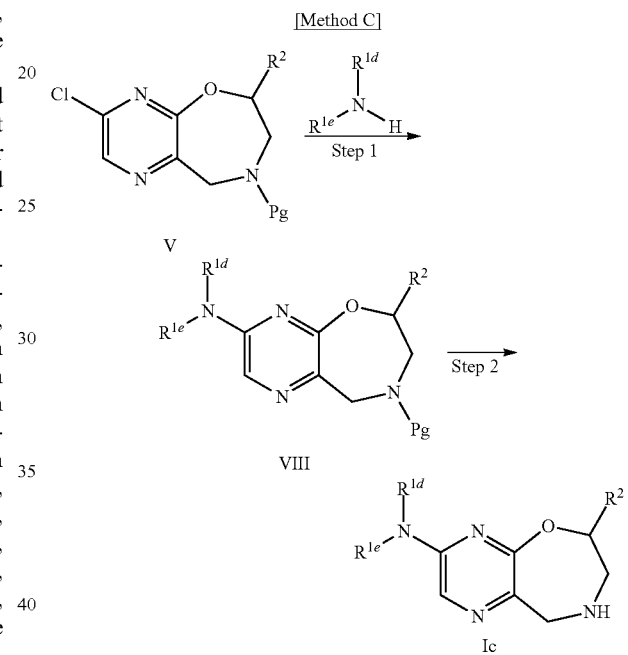

wherein R$^{1d}$ and R$^{1e}$ are the same or different and each is a C$_{1-6}$ alkyl group, or R$^{1d}$ and R$^{1e}$ may form, together with the nitrogen atom bonded thereto, a morpholino group optionally substituted by C$_{1-6}$ alkyl group(s); and other symbols are as defined above.

Step 1

In this step, compound (VIII) is produced by reacting compound (V) obtained in the aforementioned method A, steps 1 and 2, with a compound represented by the formula: R$^{1d}$R$^{1e}$NH wherein each symbol is as defined above, or a salt thereof (hereinafter sometimes to be abbreviated as R$^{1d}$R$^{1e}$NH). This reaction can be performed according to a method known per se [e.g., the method described in J. Am. Chem. Soc., 2003, vol. 125, page 6653 or J. Org. Chem., 2000, vol. 65, page 1174 etc.], and can be performed, for example, in the presence of a transition metal catalyst and a base, in a solvent that does not adversely influence the reaction.

The amount of R$^{1d}$R$^{1e}$NH to be used is generally about 1 mol-about 100 mol, preferably about 1 mol-about 3 mol, per 1 mol of compound (V).

Examples of the transition metal catalyst include palladium catalysts (e.g., palladium acetate(II), tris(dibenzylideneacetone)dipalladium(0), palladium chloride(II), tetrakis (triphenylphosphine)palladium(0) etc.), nickel catalysts (e.g., nickel chloride etc.) and the like. Where necessary, a ligand (e.g., 2-dicyclohexylphosphino-2',4',6'-triisopropyl-1,1'-biphenyl, triphenylphosphine, (R)-(-)-1-[(S)-2-(dicyclohexylphosphino)ferrocenyl]ethyldi-tert-butylphosphine, tri-tert-butylphosphine etc.) may be added.

While the amount of the transition metal catalyst to be used varies depending on the kind thereof, it is generally about 0.0001 mol-about 1 mol, preferably about 0.01 mol-about 0.5 mol, per 1 mol of compound (V). The amount of the ligand to be used is generally about 0.0001 mol-about 4 mol, preferably about 0.01 mol-about 0.2 mol, per 1 mol of compound (V).

Examples of the base include organic amines (e.g., trimethylamine, triethylamine, diisopropylethylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), alkali metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium hexamethyl disilazide, sodium hexamethyl disilazide, potassium hexamethyl disilazide etc.) and the like. Of these, alkali metal salts such as potassium carbonate, cesium carbonate, sodium phosphate, potassium phosphate and the like; alkali metal alkoxides such as sodium tert-butoxide, potassium tert-butoxide and the like; organic amines such as triethylamine, diisopropylethylamine etc.; and the like are preferable.

The amount of the base to be used is generally about 0.1 mol-about 10 mol, preferably about 1 mol-about 5 mol, per 1 mol of compound (V).

Examples of the solvent that does not adversely influence the reaction include hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran etc.), aprotic polar solvents (e.g., N,N-dimethylformamide, dimethyl sulfoxide, hexamethylphosphoramide etc.) and the like. These solvents may be used in a mixture at an appropriate ratio.

The reaction temperature is generally about −10° C. to about 200° C., preferably about 0° C. to about 150° C.

The reaction time is generally about 0.5 hr-about 48 hr, preferably about 0.5 hr-about 16 hr.

The thus-obtained compound (VIII) can be isolated and purified by a known separation and purification means, for example, concentration, concentration under reduced pressure, solvent extraction, crystallization, recrystallization, phase transfer, chromatography and the like. Alternatively, compound (VIII) may be used, without isolation, for the next reaction.

Step 2

In this step, compound (Ic) is obtained by removing the protecting group from compound (VIII). This step can be performed in the same manner as in the aforementioned method A, step 4.

The thus-obtained compound (Ic) can be isolated and purified by a known separation and purification means, for example, concentration, concentration under reduced pressure, solvent extraction, crystallization, recrystallization, phase transfer, chromatography and the like.

Compound (I) can be produced, for example, according to method D shown below, or a method analogous thereto.

[Method D]

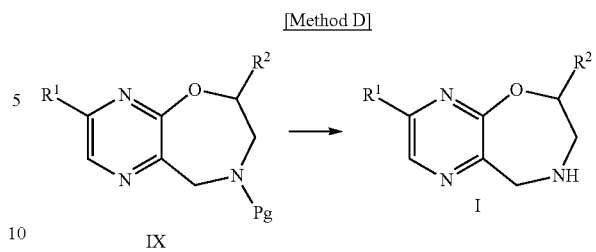

wherein each symbol is as defined above.

In this method, compound (I) is obtained by removing the protecting group from compound (IX).

The removal of the protecting group in the method can be performed according to a reaction known per se as a protecting group removal method or a method analogous thereto.

When Pg is a benzyl group, examples of the protecting group removal method include a treatment method with acid halide and the like. As the acid halide, 1-chloroethyl chloroformate, 2,2,2-trichloro-1,1-dimethylethyl chloroformate, β-trimethylsilylethyl chloroformate and the like can be used. Of these, 1-chloroethyl chloroformate is preferably used. When $R^1$ is a $C_{3-6}$ cycloalkenyl group, deprotection can be performed without reduction of cycloalkenyl by this method.

When 1-chloroethyl chloroformate is used, the amount thereof to be used is generally about 1-about 10 mol, preferably about 1-about 2 mol, per 1 mol of compound (IX). The reaction can be generally performed in a solvent that does not adversely influence the reaction.

Examples of the solvent that does not adversely influence the reaction include hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide and the like), nitriles (e.g., acetonitrile and the like) and the like. These solvents may be used in a mixture at an appropriate ratio.

The reaction temperature is generally about −80° C. to about 150° C., preferably about 0° C. to about 100° C.

The reaction time is generally about 5 min-about 72 hr, preferably about 0.5 hr-about 20 hr.

When 1-chloroethyl chloroformate is used, compound (IX) is reacted with 1-chloroethyl chloroformate and the resulting compound is treated with alcohols (e.g., methanol, ethanol and the like), an aqueous solution (e.g., aqueous sodium hydroxide solution and the like) or water, whereby compound (I) can be obtained.

The reaction temperature is generally about 0° C. to about 150° C., preferably about 5° C. to about 100° C.

The reaction time is generally about 5 min-about 24 hr, preferably about 0.5 hr-about 5 hr.

The thus-obtained compound (I) can be isolated and purified by a known separation and purification means, for example, concentration, concentration under reduced pressure, solvent extraction, crystallization, recrystallization, phase transfer, chromatography and the like.

Compound (VIII) in method C can also be produced using the following method E or a method analogous thereto.

[Method E]

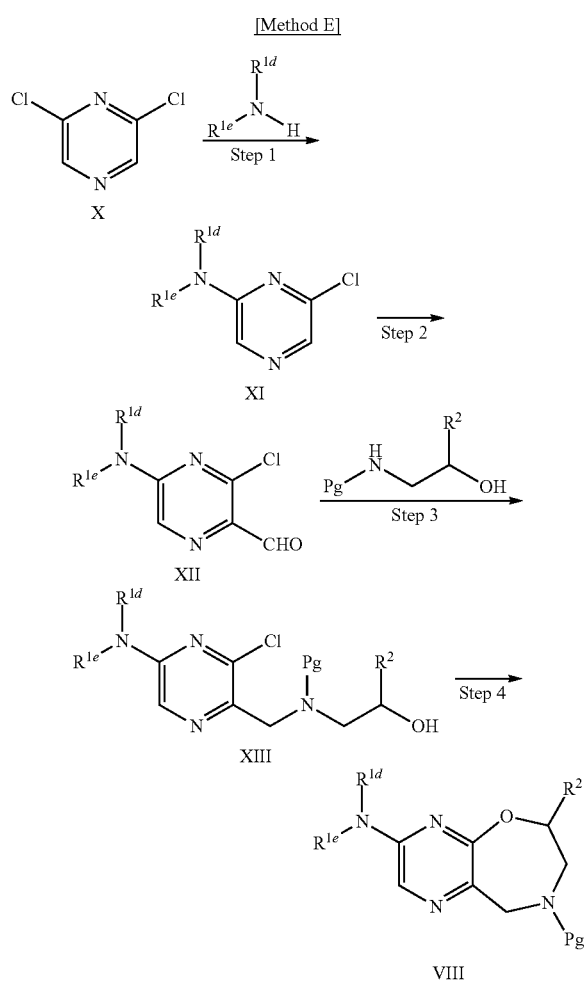

wherein each symbol is as defined above.
Step 1

In this step, compound (XI) is produced by reacting compound (X) with $R^{1d}R^{1e}NH$. This reaction is generally performed in the presence of a base and, where necessary, in a solvent that does not adversely influence the reaction.

The amount of $R^{1d}R^{1e}NH$ to be used is generally about 1 mol-about 100 mol, preferably about 1 mol-about 3 mol, per 1 mol of compound (X).

Examples of the base include alkali metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate, cesium carbonate and the like; alkali metal alkoxide such as sodium methoxide, sodium ethoxide etc. and the like), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.) and the like. Of these, alkali metal carbonates such as sodium carbonate, potassium carbonate, cesium carbonate and the like are preferable.

While the amount of the base to be used varies depending on the kind of solvent and other reaction conditions, it is generally about 0.1 mol-about 10 mol, preferably about 0.1 mol-about 5 mol, per 1 mol of compound (X).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.) and the like. These solvents may be used in a mixture at an appropriate ratio.

The reaction temperature is generally about −50° C. to about 300° C., preferably about 0° C. to about 200° C.

The reaction time varies depending on the kind of compound (X), reaction temperature and the like, and is generally about 0.1 hr-about 100 hr, preferably about 0.5 hr-about 36 hr.

The thus-obtained compound (XI) can be isolated and purified by a known separation and purification means, for example, concentration, concentration under reduced pressure, solvent extraction, crystallization, recrystallization, phase transfer, chromatography and the like. Alternatively, compound (XI) may be used, without isolation, for the next reaction.

Step 2

In this step, compound (XII) is produced by subjecting compound (XI) to a formylation reaction.

This reaction can be performed according to a method known per se [e.g., the method described in 4th ed., Jikken Kagaku Koza, vol. 21, page 110 etc.], and is generally performed using a Vilsmeier complex that can be prepared from formamide (e.g., N,N-dimethylformamide, N-methylformanilide etc.), and a halogenated reagent (e.g., phosphoryl chloride, phosgene, oxalyl chloride, thionyl chloride, triphenylphosphine bromine complex etc.) and the like and, where necessary, in a solvent that does not adversely influence the reaction.

While the amount of formamide to be used varies depending on the kind of solvent and other reaction conditions, it is generally about 1 mol-about 100 mol, preferably about 1 mol-about 10 mol, per 1 mol of compound (XI). Alternatively, formamide may be used as a solvent.

While the amount of the halogenated reagent to be used varies depending on the kind of solvent and other reaction conditions, it is generally about 1 mol-about 10 mol, preferably about 1 mol-about 5 mol, per 1 mol of compound (XI).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), formamides (e.g., N,N-dimethylformamide, N-methylformanilide etc.) and the like.

For preparation of a Vilsmeier complex, the reaction temperature employed is generally about −50° C. to about 50° C., preferably about −20° C. to about 10° C.

The reaction time is generally about 0.1 hr-about 10 hr, preferably about 0.2 hr-about 1 hr.

In the reaction with a Vilsmeier complex and compound (XI), the reaction temperature is generally about −50° C. to about 300° C., preferably about 0° C. to about 200° C.

The reaction time varies depending on the kind of compound (XI), reaction temperature and the like, and is generally about 0.1 hr-about 100 hr, preferably about 0.5 hr-about 36 hr.

The thus-obtained compound (XII) can be isolated and purified by a known separation and purification means, for example, concentration, concentration under reduced pressure, solvent extraction, crystallization, recrystallization, phase transfer, chromatography and the like. Alternatively, compound (XII) may be used, without isolation, for the next reaction.

Step 3

In this step, compound (XIII) is produced from compound (XII). This reaction can be performed according to the aforementioned method A, step 1, or a method analogous thereto.

The thus-obtained compound (XIII) can be isolated and purified by a known separation and purification means, for example, concentration, concentration under reduced pressure, solvent extraction, crystallization, recrystallization, phase transfer, chromatography and the like. Alternatively, compound (XIII) may be used, without isolation, for the next reaction.

Step 4

In this step, compound (VIII) is produced from compound (XIII). This reaction can be performed according to the aforementioned method A, step 2, or a method analogous thereto.

The thus-obtained compound (VIII) can be isolated and purified by a known separation and purification means, for example, concentration, concentration under reduced pressure, solvent extraction, crystallization, recrystallization, phase transfer, chromatography and the like. Alternatively, compound (VIII) may be used, without isolation, for the next reaction.

In the following, production methods of compound ($I_0$) of the present invention are explained.

Compound ($I_0$) of the present invention can be produced, for example, according to the following method F, method G, method H, method I, method J, method K, method L, method M or method N, or a method analogous thereto. Compounds ($I_0$a), ($I_0$b), ($I_0$c), ($I_0$d), ($I_0$e), ($I_0$f), ($I_0$g), ($I_0$h), ($I_0$i), ($I_0$j) and ($I_0$k) obtained by respective production methods are encompassed in compound ($I_0$).

[Method F]

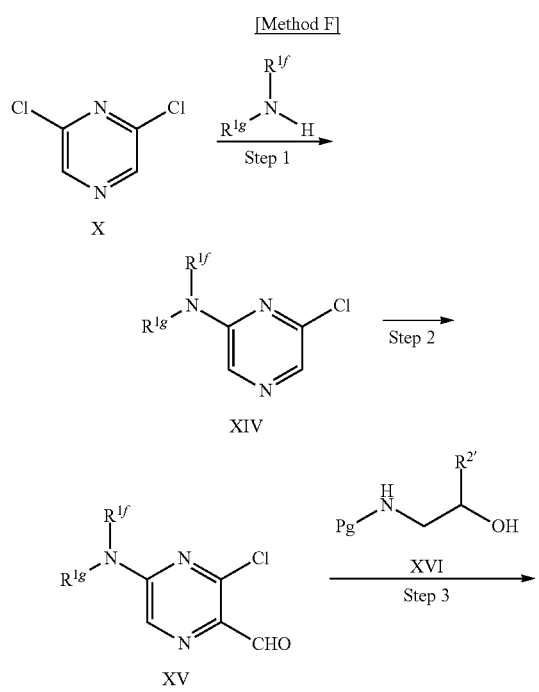

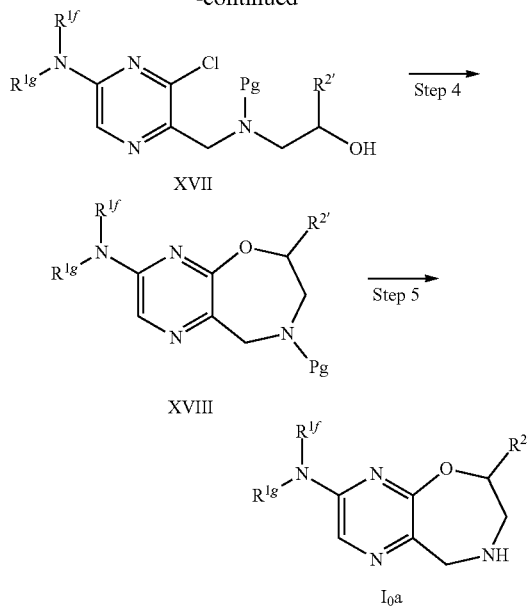

wherein $R^{1f}$ and $R^{1g}$ are the same or different and each is (a) a $C_{1-6}$ alkyl group optionally substituted by substituent(s) selected from a $C_{3-6}$ cycloalkyl group and a phenyl group, or (b) a $C_{3-6}$ cycloalkyl group, or $R^{1f}$ and $R^{1g}$ form, together with the nitrogen atom bonded thereto, a morpholinyl group optionally substituted by $C_{1-6}$ alkyl group(s), a piperidyl group optionally substituted by $C_{1-6}$ alkyl group(s), or a pyrrolidinyl group optionally substituted by $C_{1-6}$ alkyl group(s) optionally substituted by $C_{1-6}$ alkoxy group(s); and other symbols are as defined above.

Step 1

In this step, compound (XIV) is produced by reacting compound (X) with a compound represented by the formula: $R^{1f}R^{1g}$NH or a salt thereof (hereinafter sometimes to be abbreviated as $R^{1f}R^{1g}$NH). This reaction is generally performed in the presence of a base and, where necessary, in a solvent that does not adversely influence the reaction.

$R^{1f}R^{1g}$NH may be a commercially available product, or can be produced from the corresponding starting compounds by applying a means known per se.

The amount of $R^{1f}R^{1g}$NH to be used is generally about 0.5 mol-about 100 mol, preferably about 1 mol-about 10 mol, per 1 mol of compound (X).

Examples of the base include alkali metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate, cesium carbonate and the like; alkali metal alkoxides such as sodium methoxide, sodium ethoxide etc. and the like), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.) and the like. Of these, alkali metal carbonates such as sodium carbonate, potassium carbonate, cesium carbonate and the like are preferable.

While the amount of the base to be used varies depending on the kind of solvent and other reaction conditions, it is generally about 0.1 mol-about 10 mol, preferably about 0.1 mol-about 5 mol, per 1 mol of compound (X).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.) and the like. These solvents may be used in a mixture at an appropriate ratio.

The reaction temperature is generally about −50° C. to about 300° C., preferably about 0° C. to about 200° C.

The reaction time varies depending on the kind of $R^{1f}R^{1g}NH$, reaction temperature and the like, and is generally about 0.1 hr-about 100 hr, preferably about 0.5 hr-about 36 hr.

The thus-obtained compound (XIV) can be isolated and purified by a known separation and purification means, for example, concentration, concentration under reduced pressure, solvent extraction, crystallization, recrystallization, phase transfer, chromatography and the like. Alternatively, compound (XIV) may be used, without isolation, for the next reaction.

Step 2

In this step, compound (XV) is produced by subjecting compound (XIV) to a formylation reaction.

This reaction can be performed according to a method known per se [e.g., the method described in 4th ed., Jikken Kagaku Koza, vol. 21, page 110 etc.], and is generally performed using a Vilsmeier complex that can be prepared from formamide (e.g., N,N-dimethylformamide, N-methylformanilide etc.), and a halogenated reagent (e.g., phosphoryl chloride, phosgene, oxalyl chloride, thionyl chloride, triphenylphosphine bromine complex etc.) and the like and, where necessary, in a solvent that does not adversely influence the reaction.

While the amount of formamide to be used varies depending on the kind of solvent and other reaction conditions, it is generally about 0.5 mol-about 100 mol, preferably about 1 mol-about 10 mol, per 1 mol of compound (XIV). Alternatively, formamide may be used as a solvent.

While the amount of the halogenated reagent to be used varies depending on the kind of solvent and other reaction conditions, it is generally about 0.5 mol-about 10 mol, preferably about 1 mol-about 5 mol, per 1 mol of compound (XIV).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), formamides (e.g., N,N-dimethylformamide, N-methylformanilide etc.) and the like.

For preparation of a Vilsmeier complex, the reaction temperature employed is generally about −50° C. to about 50° C., preferably about −20° C. to about 10° C.

The reaction time is generally about 0.1 hr-about 10 hr, preferably about 0.2 hr-about 1 hr.

In the reaction with a Vilsmeier complex and compound (XIV), the reaction temperature is generally about −50° C. to about 300° C., preferably about 0° C. to about 200° C.

The reaction time varies depending on the kind of compound (XIV), reaction temperature and the like, and is generally about 0.1 hr-about 100 hr, preferably about 0.5 hr-about 36 hr.

The thus-obtained compound (XV) can be isolated and purified by a known separation and purification means, for example, concentration, concentration under reduced pressure, solvent extraction, crystallization, recrystallization, phase transfer, chromatography and the like. Alternatively, compound (XV) may be used, without isolation, for the next reaction.

Step 3

In this step, compound (XVII) is produced from compound (XV) and compound (XVI). This reaction can be performed according to the aforementioned method A, step 1, or a method analogous thereto.

The thus-obtained compound (XVII) can be isolated and purified by a known separation and purification means, for example, concentration, concentration under reduced pressure, solvent extraction, crystallization, recrystallization, phase transfer, chromatography and the like. Alternatively, compound (XVII) may be used, without isolation, for the next reaction.

Step 4

In this step, compound (XVIII) is produced from compound (XVII). This reaction can be performed according to the aforementioned method A, step 2, or a method analogous thereto.

The thus-obtained compound (XVIII) can be isolated and purified by a known separation and purification means, for example, concentration, concentration under reduced pressure, solvent extraction, crystallization, recrystallization, phase transfer, chromatography and the like. Alternatively, compound (XVIII) may be used, without isolation, for the next reaction.

Step 5

In this step, compound ($I_0a$) is obtained by removing the protecting group from compound (XVIII). This step can be performed in the same manner as in the aforementioned A, step 4.

The thus-obtained compound ($I_0a$) can be isolated and purified by a known separation and purification means, for example, concentration, concentration under reduced pressure, solvent extraction, crystallization, recrystallization, phase transfer, chromatography and the like.

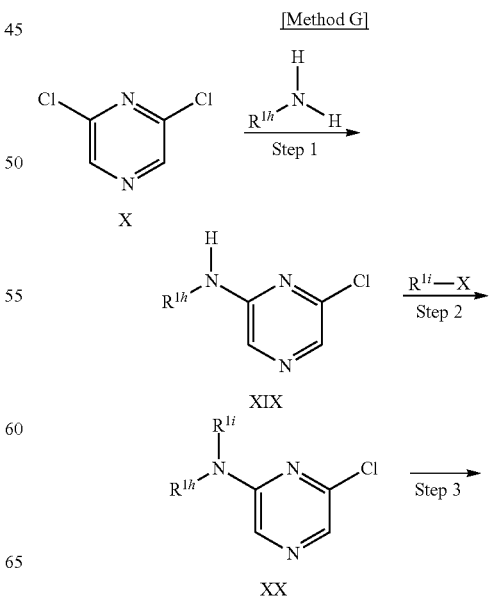

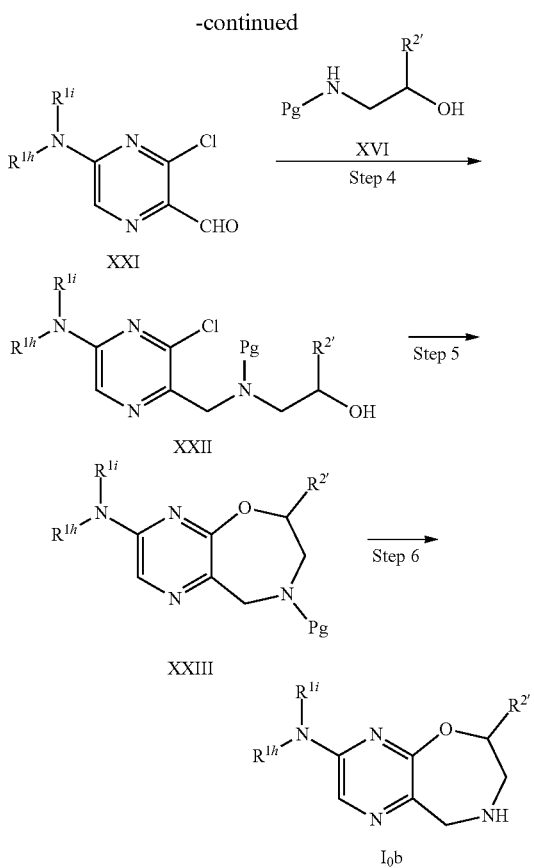

wherein $R^{1h}$ is (a) a $C_{1-6}$ alkyl group optionally substituted by substituent(s) selected from a $C_{3-6}$ cycloalkyl group and a phenyl group, or (b) a $C_{3-6}$ cycloalkyl group; $R^{1i}$ is a $C_{1-6}$ alkyl group; X is halogen atoms such as a chlorine atom, a bromine atom, an iodine atom and the like; and other symbols are as defined above.

Step 1

In this step, compound (XIX) is produced by reacting compound (X) with a compound represented by the formula: $R^{1h}NH_2$ or a salt thereof. This step can be performed according to the aforementioned method F, step 1, or a method analogous thereto.

The thus-obtained compound (XIX) can be isolated and purified by a known separation and purification means, for example, concentration, concentration under reduced pressure, solvent extraction, crystallization, recrystallization, phase transfer, chromatography and the like. Alternatively, compound (XIX) may be used, without isolation, for the next reaction.

Step 2

In this step, compound (XX) is produced by subjecting compound (XIX) to an alkylation reaction. The alkylation reaction can be performed according to a conventional method in the presence of a base and alkylhalide represented by the formula: $R^{1i}$—X (hereinafter to be abbreviated as $R^{1i}$—X), in a solvent that does not adversely influence the reaction.

Examples of the base include alkali metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate, cesium carbonate and the like; alkali metal alkoxides such as sodium methoxide, sodium ethoxide etc. and the like), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.), organic lithium reagents (e.g., n-butyl lithium, tert-butyl lithium, methyl lithium etc.), alkali metal disilazides (e.g., lithium hexamethyl disilazide, sodium hexamethyl disilazide, potassium hexamethyl disilazide etc.) and the like.

$R^{1i}$—X may be a commercially available product, or can be produced from the corresponding starting compounds by applying a means known per se.

The amount of each of the base and $R^{1i}$—X to be used is about 0.5-about 20 mol, preferably about 1-about 5 mol, per 1 mol of compound (XIX).

Examples of the solvent that does not adversely influence the reaction include ethers such as tetrahydrofuran and the like; halogenated hydrocarbons such as chloroform and the like; aromatic hydrocarbons such as toluene and the like; amides such as N,N-dimethylformamide and the like; sulfoxides such as dimethyl sulfoxide and the like, hexane etc.; and the like. These solvents may be used in a mixture at an appropriate ratio.

The reaction temperature is generally about −78° C. to about 250° C., preferably −78° C.-120° C. The reaction time is generally about 0.5-about 24 hr.

The thus-obtained compound (XX) can be isolated and purified by a known separation and purification means, for example, concentration, concentration under reduced pressure, solvent extraction, crystallization, recrystallization, phase transfer, chromatography and the like. Alternatively, compound (XX) may be used, without isolation, for the next reaction.

Step 3

In this step, compound (XXI) is produced by subjecting compound (XX) to formylation. This step can be performed according to the aforementioned method F, step 2, or a method analogous thereto. The thus-obtained compound (XXI) can be isolated and purified by a known separation and purification means, for example, concentration, concentration under reduced pressure, solvent extraction, crystallization, recrystallization, phase transfer, chromatography and the like. Alternatively, compound (XXI) may be used, without isolation, for the next reaction.

Step 4

In this step, compound (XXII) is produced by subjecting compound (XXI) and compound (XVI) to a reductive amination reaction. This step can be performed according to the aforementioned method A, step 1, or a method analogous thereto. The thus-obtained compound (XXII) can be isolated and purified by a known separation and purification means, for example, concentration, concentration under reduced pressure, solvent extraction, crystallization, recrystallization, phase transfer, chromatography and the like. Alternatively, compound (XXII) may be used, without isolation, for the next reaction.

Step 5

In this step, compound (XXIII) is produced from compound (XXII). This step can be performed according to the aforementioned method A, step 2, or a method analogous thereto. The thus-obtained compound (XXIII) can be isolated and purified by a known separation and purification means, for example, concentration, concentration under reduced pressure, solvent extraction, crystallization, recrystallization, phase transfer, chromatography and the like. Alternatively, compound (XXIII) may be used, without isolation, for the next reaction.

Step 6

In this step, compound ($I_0$b) is obtained by removing the protecting group from compound (XXIII). This step can be performed according to the aforementioned method A, step 4.

The thus-obtained compound ($I_0$b) can be isolated and purified by a known separation and purification means, for example, concentration, concentration under reduced pressure, solvent extraction, crystallization, recrystallization, phase transfer, chromatography and the like.

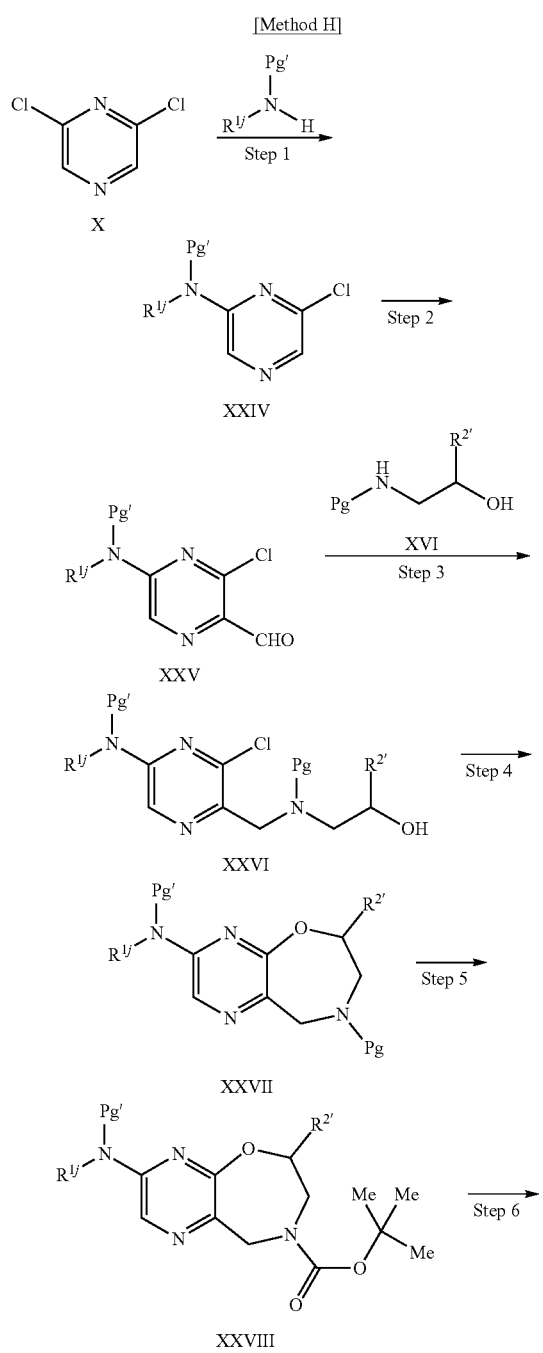

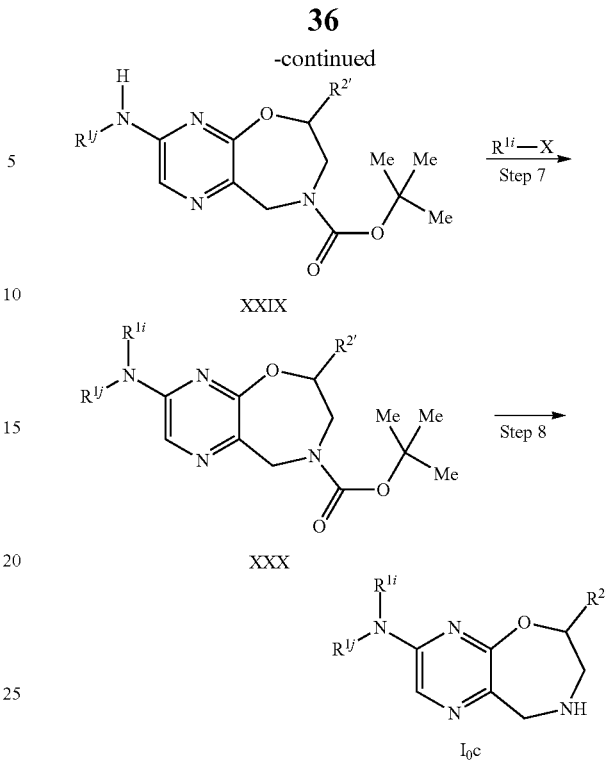

wherein is a $C_{1-6}$ alkyl group; Pg' is a protecting group; and other symbols are as defined above.

Examples of the "protecting group" for Pg' include an amino-protecting group generally used for peptide synthesis and the like, which does not adversely influence the progress of the reaction in each step explained below (e.g., a benzyl group, a p-methoxybenzyl group) and the like, with preference given to a benzyl group.

Step 1

In this step, compound (XXIV) is produced by reacting compound (X) with a compound represented by the formula: $R^{1j}$PgNH or a salt thereof. This step can be performed in the same manner as in the aforementioned method F, step 1.

The thus-obtained compound (XXIV) can be isolated and purified by a known separation and purification means, for example, concentration, concentration under reduced pressure, solvent extraction, crystallization, recrystallization, phase transfer, chromatography and the like.

Step 2

In this step, compound (XXV) is produced by subjecting compound (XXIV) to a formylation reaction. This step can be performed in the same manner as in the aforementioned method F, step 2.

The thus-obtained compound (XXV) can be isolated and purified by a known separation and purification means, for example, concentration, concentration under reduced pressure, solvent extraction, crystallization, recrystallization, phase transfer, chromatography and the like.

Step 3

In this step, compound (XXVI) is produced from compound (XXV) and compound (XVI). This reaction can be performed according to the aforementioned method A, step 1, or a method analogous thereto.

The thus-obtained compound (XXVI) can be isolated and purified by a known separation and purification means, for example, concentration, concentration under reduced pressure, solvent extraction, crystallization, recrystallization, phase transfer, chromatography and the like.

Step 4

In this step, compound (XXVII) is produced from compound (XXVI). This reaction can be performed according to the aforementioned method A, step 2, or a method analogous thereto.

The thus-obtained compound (XXVII) can be isolated and purified by a known separation and purification means, for example, concentration, concentration under reduced pressure, solvent extraction, crystallization, recrystallization, phase transfer, chromatography and the like.

Step 5

In this step, the protecting group (Pg) is removed from compound (XXVII), and a tert-butoxycarbonyl group is introduced thereinto, whereby compound (XXVIII) is obtained. In this step, the protecting group (Pg) is removed in the same manner as in the aforementioned method A, step 4, and a tert-butoxycarbonyl group can be introduced according to a known method.

The tert-butoxycarbonylation reaction is performed according to a conventional method and using di-tert-butyl dicarbonate in the presence of a base, in a solvent that does not adversely influence the reaction.

Examples of the base include triethylamine, tributylamine, diisopropylethylamine, potassium carbonate, sodium carbonate, sodium hydride, potassium hydride, sodium hydroxide, potassium hydroxide and the like. The amount of the base to be used is about 0.5 mol-about 20 mol, preferably, about 1 mol-about 5 mol, per 1 mol of compound (XXVII).

Examples of the solvent that does not adversely influence the reaction include ethers such as tetrahydrofuran and the like; halogenated hydrocarbons such as chloroform and the like; aromatic hydrocarbons such as toluene and the like; amides such as N,N-dimethylformamide and the like; sulfoxides such as dimethylsulfoxide etc.; and the like. These solvents may be used in a mixture at an appropriate ratio.

The reaction temperature is generally about −50° C. to about 250° C., preferably 0° C.-120° C. The reaction time is generally about 0.5-about 24 hr.

The thus-obtained compound (XXVIII) can be isolated and purified by a known separation and purification means, for example, concentration, concentration under reduced pressure, solvent extraction, crystallization, recrystallization, phase transfer, chromatography and the like.

Step 6

In this step, compound (XXIX) is obtained by removing the protecting group (Pg') from compound (XXVIII). This step can be performed in the same manner as in the aforementioned method A, step 4.

The thus-obtained compound (XXIX) can be isolated and purified by a known separation and purification means, for example, concentration, concentration under reduced pressure, solvent extraction, crystallization, recrystallization, phase transfer, chromatography and the like.

Step 7

In this step, compound (XXIX) is subjected to an alkylation reaction and converted to compound (XXX). This step can be performed in the same manner as in the aforementioned method G, step 2.

The thus-obtained compound (XXX) can be isolated and purified by a known separation and purification means, for example, concentration, concentration under reduced pressure, solvent extraction, crystallization, recrystallization, phase transfer, chromatography and the like.

Step 8

In this step, compound ($I_0c$) is produced by removing the tert-butoxycarbonyl group from compound (XXX). While this reaction can be performed according to a method known per se, it is generally performed by reaction with an acid in a solvent that does not adversely influence the reaction.

Examples of the acid include hydrochloric acid, hydrobromic acid, sulfuric acid, trifluoroacetic acid, trifluoromethanesulfonic acid, hydrogen chloride and the like. The amount of the acid to be used is about 0.5-about 200 mol, preferably about 1-about 100 mol, per 1 mol of compound (XXX).

Examples of the solvent that does not adversely influence the reaction include alcohols (e.g., methanol etc.), ethers (e.g., tetrahydrofuran etc.), halogenated hydrocarbons (e.g., chloroform etc.), aromatic hydrocarbons (e.g., toluene etc.), amides (e.g., N,N-dimethylformamide etc.), sulfoxides (e.g., dimethyl sulfoxide etc.), esters (e.g., ethyl acetate etc.) and the like. These solvents may be used in a mixture at an appropriate ratio.

The reaction temperature is generally about −50° C. to about 250° C., preferably about 0° C. to about 120° C. The reaction time is generally about 0.5-about 24 hr.

The thus-obtained compound ($I_0c$) can be isolated and purified by a known separation and purification means, for example, concentration, concentration under reduced pressure, solvent extraction, crystallization, recrystallization, phase transfer, chromatography and the like.

[Method I]

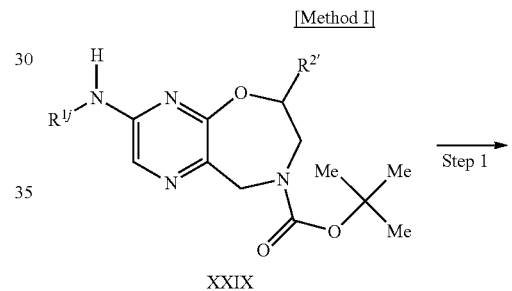

XXIX

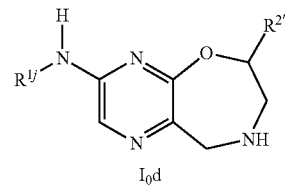

$I_0d$ wherein each symbol is as defined above.

Step 1

In this step, compound ($I_0d$) is obtained by removing the tert-butoxycarbonyl group from compound (XXIX). This step can be performed in the same manner as in the aforementioned method H, step 8.

The thus-obtained compound ($I_0d$) can be isolated and purified by a known separation and purification means, for example, concentration, concentration under reduced pressure, solvent extraction, crystallization, recrystallization, phase transfer, chromatography and the like.

[Method J]

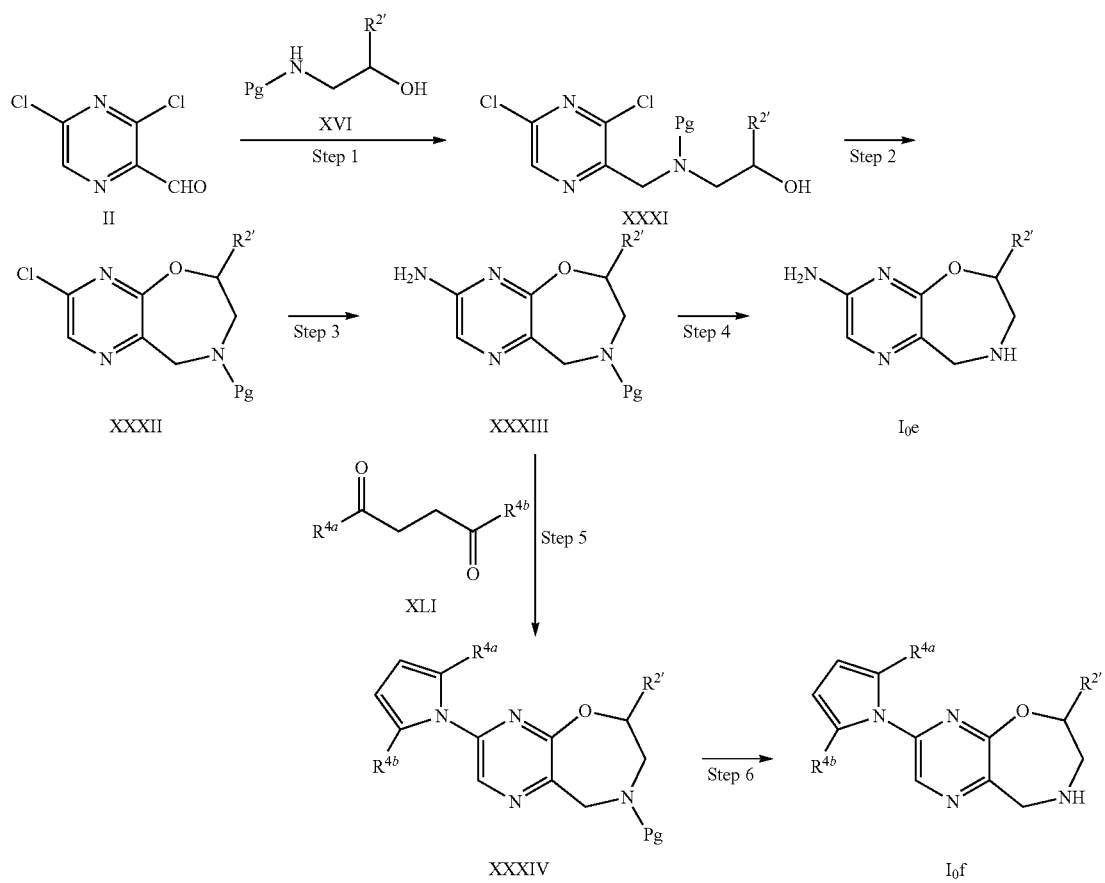

wherein $R^{4a}$ and $R^{4b}$ are each independently a $C_{1-6}$ alkyl group; and other symbols are as defined above.

Step 1

In this step, compound (XXXI) is produced from compound (II) and compound (XVI). This reaction can be performed according to the aforementioned method A, step 1, or a method analogous thereto.

The thus-obtained compound (XXXI) can be isolated and purified by a known separation and purification means, for example, concentration, concentration under reduced pressure, solvent extraction, crystallization, recrystallization, phase transfer, chromatography and the like.

Step 2

In this step, compound (XXXII) is produced from compound (XXXI). This reaction can be performed according to the aforementioned method A, step 2, or a method analogous thereto.

The thus-obtained compound (XXXII) can be isolated and purified by a known separation and purification means, for example, concentration, concentration under reduced pressure, solvent extraction, crystallization, recrystallization, phase transfer, chromatography and the like.

Step 3

In this step, compound (XXXIII) is produced by reacting compound (XXXII) with an ammonia equivalent, followed by reaction with an acid or fluorine reagent.

This reaction can be performed according to a method known per se [e.g., the method described in Organic Letters, 2001, vol. 3, page 3417 etc.] and can be performed, for example, by reacting compound (XXXII) with an ammonia equivalent in the presence of a transition metal catalyst and a base, in a solvent that does not adversely influence the reaction, followed by reaction with an acid or fluorine reagent.

Examples of the ammonia equivalent include benzophenone imine, aminotriphenylsilane, alkali metal disilazides (e.g., lithium hexamethyl disilazide, sodium hexamethyl disilazide, potassium hexamethyl disilazide etc.) and the like.

The amount of the ammonia equivalent to be used is generally about 0.5-about 20 mol, preferably, about 1-about 5 mol, per 1 mol of compound (XXXII).

Examples of the transition metal catalyst include palladium catalysts (e.g., palladium acetate(II), tris(dibenzylideneacetone)dipalladium(0), palladium chloride(II), tetrakis(triphenylphosphine)palladium(0) etc.), nickel catalysts (e.g., nickel chloride etc.) and the like. Where necessary, a ligand (e.g., 2-dicyclohexylphosphino-2',4',6'-triphenylphosphine, 2-(dicyclohexylphosphino)biphenyl, tri(tert-butyl)phosphine etc.) may be added.

While the amount of the transition metal catalyst to be used varies depending on the kind of solvent and other reaction conditions, it is generally about 0.0001 mol-about 1 mol, preferably about 0.01 mol-about 0.5 mol, per 1 mol of compound (XXXII). The amount of the ligand to be used is generally about 0.0001 mol-about 4 mol, preferably about 0.01 mol-about 0.2 mol, per 1 mol of compound (XXXII).

Examples of the base include organic amines (e.g., trimethylamine, triethylamine, diisopropylethylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), alkali metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium hexamethyl disilazide, sodium hexamethyl disilazide, potassium hexamethyl disilazide etc.) and the like. Of these, alkali metal salts such as potassium carbonate, cesium carbonate, sodium phosphate, potassium phosphate and the like; alkali metal alkoxides such as sodium tert-butoxide, potassium tert-butoxide and the like; organic amines such as triethylamine, diisopropylethylamine etc.; and the like are preferable.

The amount of the base to be used is generally about 0.1 mol-about 10 mol, preferably about 1 mol-about 5 mol, per 1 mol of compound (XXXII).

Examples of the solvent that does not adversely influence the reaction include hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran etc.), aprotic polar solvents (e.g., N,N-dimethylformamide, dimethyl sulfoxide, hexamethylphosphoramide etc.) and the like. These solvents may be used in a mixture at an appropriate ratio.

The reaction temperature is generally about −10° C. to about 200° C., preferably about 0° C. to about 150° C.

The reaction time is generally about 0.5 hr-about 48 hr, preferably about 0.5 hr-about 16 hr.

After reaction with an ammonia equivalent, the reaction mixture is reacted with an acid or fluorine reagent, whereby compound (XXXIII) can be obtained.

Examples of the acid include mineral acids such as hydrochloric acid, phosphoric acid, sulfuric acid and the like, organic acids such as toluenesulfonic acid, methanesulfonic acid, acetic acid and the like. Of these, hydrochloric acid is preferable.

The amount of the acid to be used is about 0.1 mol-about 100 mol, preferably about 1 mol-about 50 mol, per 1 mol of compound (XXXII).

When alkali metal disilazide (e.g., lithium hexamethyl disilazide, sodium hexamethyl disilazide, potassium hexamethyl disilazide etc.) is used as an ammonia equivalent, a fluorine reagent (e.g., tetrabutylammonium fluoride, pyridine-hydrogen fluoride complex, lithium tetrafluoroborate) may be used. Of these, tetrabutylammonium fluoride is preferable.

The amount of the fluorine reagent to be used is about 0.5 mol-about 100 mol, preferably about 1-about 10 mol, per 1 mol of compound (XXXII).

The reaction temperature is generally about −10° C. to about 200° C., preferably about 0° C. to about 150° C.

The reaction time is generally about 0.5 hr-about 48 hr, preferably about 0.5 hr-about 16 hr.

The thus-obtained compound (XXXIII) can be isolated and purified by a known separation and purification means, for example, concentration, concentration under reduced pressure, solvent extraction, crystallization, recrystallization, phase transfer, chromatography and the like. Alternatively, compound (XXXIII) may be used, without isolation, for the next reaction.

Step 4

In this step, compound ($I_0e$) is obtained by removing a protecting group from compound (XXXIII). This step can be performed in the same manner as in the aforementioned method A, step 4.

The thus-obtained compound ($I_0e$) can be isolated and purified by a known separation and purification means, for example, concentration, concentration under reduced pressure, solvent extraction, crystallization, recrystallization, phase transfer, chromatography and the like.

Step 5

In this step, compound (XXXIV) is produced by reacting compound (XXXIII) with diketone form (XLI). Where necessary, acid (e.g., mineral acids such as hydrochloric acid, phosphoric acid, sulfuric acid and the like, organic acids such as toluenesulfonic acid, methanesulfonic acid, acetic acid and the like) may be added in an amount of about 0.1 mol-about 10 mol, preferably about 0.5 mol-about 10 mol, per 1 mol of compound (XXXIII).

The amount of the diketone form (XLI) to be used is about 0.5 mol-about 20 mol, preferably about 1 mol-about 10 mol, per 1 mol of compound (XXXIII).

This reaction is advantageously performed without a solvent or in a solvent inert to the reaction. While such solvent is not particularly limited as long as the reaction proceeds, for example, alcohols such as methanol, ethanol, 1-propanol, 2-propanol, tert-butyl alcohol and the like; halogenated hydrocarbons such as dichloromethane, chloroform, 1,2-dichloroethane and the like; ethers such as diethyl ether, diisopropyl ether, diphenylether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propanoic acid, trifluoroacetic acid, methanesulfonic acid etc. and the like, or a mixed solvent thereof and the like are preferable.

While the reaction time varies depending on the reagent and solvent to be used, it is generally about 10 min-about 100 hr, preferably about 30 min-about 50 hr.

The reaction temperature is generally about −20° C. to about 150° C., preferably about 0° C. to about 100° C.

The thus-obtained compound (XXXIV) can be isolated and purified by a known separation and purification means, for example, concentration, concentration under reduced pressure, solvent extraction, crystallization, recrystallization, phase transfer, chromatography and the like.

Step 6

In this step, compound ($I_0f$) is obtained by removing the protecting group from compound (XXXIV). This step can be performed in the same manner as in the aforementioned method A, step 4.

The thus-obtained compound ($I_0f$) can be isolated and purified by a known separation and purification means, for example, concentration, concentration under reduced pressure, solvent extraction, crystallization, recrystallization, phase transfer, chromatography and the like.

[Method K]

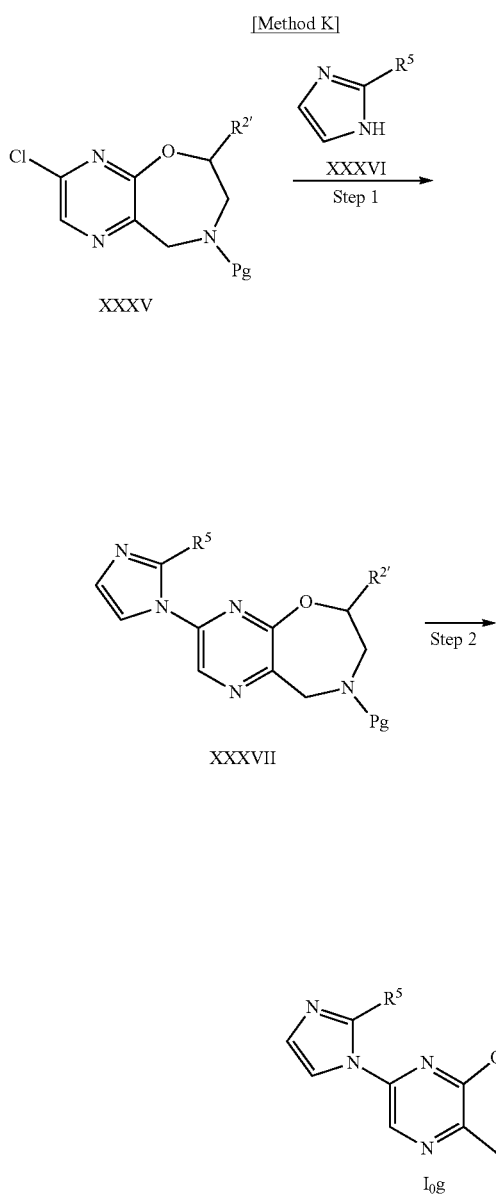

wherein $R^5$ is a $C_{1-6}$ alkyl group; and other symbols are as defined above.

Step 1

In this step, compound (XXXVII) is produced by reacting compound (XXXV) with compound (XXXVI).

This reaction can be performed in the presence of a base and, where necessary, in the presence of a copper salt, in a solvent that does not adversely influence the reaction.

While the amount of compound (XXXVI) to be used varies depending on the kind of solvent and other reaction conditions, it is generally about 0.5 mol-about 50 mol, preferably about 1 mol-about 10 mol, per 1 mol of compound (XXXV).

Examples of the base include metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate, cesium carbonate and the like; alkali metal alkoxides such as sodium methoxide, sodium ethoxide, sodium tert-butoxide, potassium tert-butoxide etc. and the like), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.), alkali metal disilazides (e.g., lithium hexamethyl disilazide, sodium hexamethyl disilazide, potassium hexamethyl disilazide etc.) and the like. Of these, alkali metal carbonates such as sodium carbonate, potassium carbonate, cesium carbonate etc.; and the like are preferable.

While the amount of the base to be used varies depending on the kind of solvent and other reaction conditions, it is generally about 0.1 mol-about 10 mol, preferably about 0.1 mol-about 5 mol, per 1 mol of compound (XXXV).

Examples of the copper salt include copper halides (e.g., copper chloride, copper bromide, copper iodide etc.), copper oxide, copper sulfate, copper acetate, copper trifluoromethanesulfonate and the like. Of these, copper halides such as copper chloride, copper bromide, copper iodide and the like are preferable.

While the amount of the copper salt to be used varies depending on the kind of solvent and other reaction conditions, it is generally about 0.01 mol-about 50 mol, preferably about 0.1 mol-about 10 mol, per 1 mol of compound (XXXV).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide, N-methylpyrrolidone etc.), sulfoxides (e.g., dimethyl sulfoxide etc.) and the like. These solvents may be used in a mixture at an appropriate ratio.

The reaction temperature is generally about −50° C. to about 300° C., preferably about −20° C. to about 150° C.

The reaction time varies depending on the kind of compound (XXXV), reaction temperature and the like, and is generally about 0.1 hr-about 100 hr, preferably about 0.5 hr-about 24 hr.

The thus-obtained compound (XXXVII) can be isolated and purified by a known separation and purification means, for example, concentration, concentration under reduced pressure, solvent extraction, crystallization, recrystallization, phase transfer, chromatography and the like.

Step 2

In this step, compound ($I_0g$) is obtained by removing the protecting group from compound (XXXVII). This step can be performed in the same manner as in the aforementioned method A, step 4.

The thus-obtained compound ($I_0g$) can be isolated and purified by a known separation and purification means, for example, concentration, concentration under reduced pressure, solvent extraction, crystallization, recrystallization, phase transfer, chromatography and the like.

[Method L]

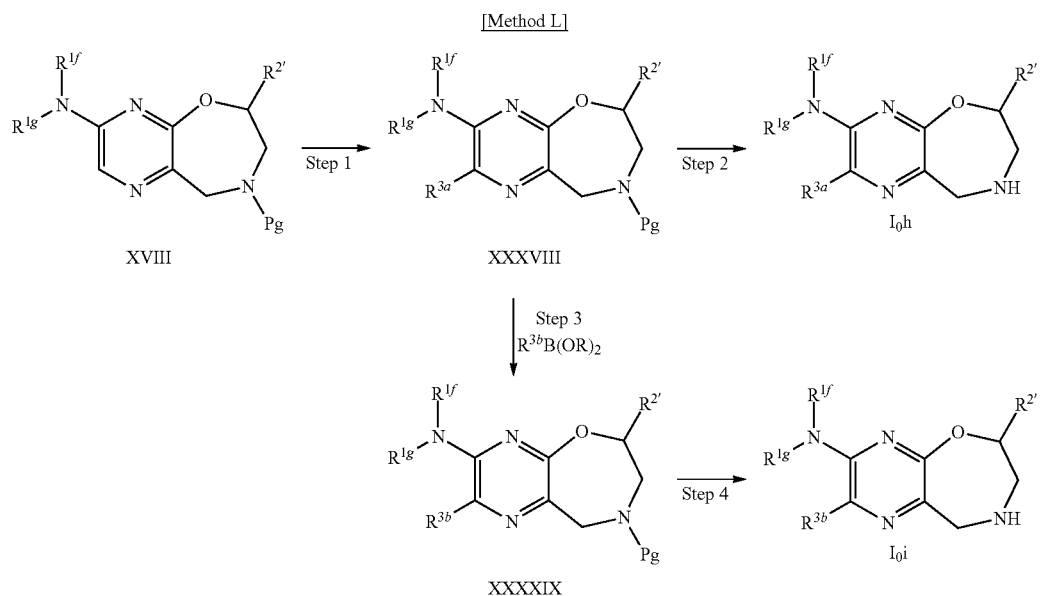

wherein $R^{3a}$ is a halogen atom; $R^{3b}$ is a $C_{1-6}$ alkyl group; and other symbols are as defined above.

Step 1

In this step, compound (XXXVIII) is obtained by halogenating compound (XVIII).

This reaction can be performed using a halogen reagent (for example, chlorine, bromine, iodine), N-halogenated succinimide (e.g., N-chlorosuccinimide, N-bromosuccinimide, N-iodosuccinimide) in a solvent that does not adversely influence the reaction.

The amount of the halogen reagent or halogenated succinimide to be used is generally about 0.5 mol-10 mol, preferably about 1 mol-about 3 mol, per 1 mol of compound (XVIII).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), organic acids (e.g., formic acid, acetic acid, propionic acid) and the like. These solvents may be used in a mixture at an appropriate ratio.

The reaction temperature is generally within the range of about −50° C. to about 300° C., preferably about 0° C. to about 200° C. The reaction time varies depending on the kind of compound (XVIII), reaction temperature and the like, and is generally about 0.1 hr-about 100 hr, preferably about 0.5 hr-about 36 hr.

The thus-obtained compound (XXXVIII) can be isolated and purified by a known separation and purification means, for example, concentration, concentration under reduced pressure, solvent extraction, crystallization, recrystallization, phase transfer, chromatography and the like.

Step 2

In this step, compound ($I_0h$) is obtained by removing the protecting group from compound (XXXVIII). This step can be performed in the same manner as in the aforementioned method D.

The thus-obtained compound ($I_0h$) can be isolated and purified by a known separation and purification means, for example, concentration, concentration under reduced pressure, solvent extraction, crystallization, recrystallization, phase transfer, chromatography and the like.

Step 3

In this step, compound (XXXIX) is produced by subjecting compound (XXXVIII) and a compound represented by the formula: $R^{3b}$—$B(OR)_2$ (hereinafter to be abbreviated as $R^{3b}$—$B(OR)_2$) to a coupling reaction.

This reaction can be performed according to a method known per se [e.g., the method described in Chemical Reviews, 1995, vol. 95, page 2457 etc.] and can be performed, for example, in the presence of a transition metal catalyst and a base, in a solvent that does not adversely influence the reaction.

The amount of $R^{3b}$—$B(OR)_2$ to be used is generally about 0.5 mol-about 10 mol, preferably about 1 mol-about 5 mol, per 1 mol of compound (XXXVIII).

As the transition metal catalyst, palladium catalysts (e.g., palladium acetate(II), palladium chloride(II), tetrakis(triphenylphosphine)palladium(0) etc.), nickel catalysts (e.g., nickel chloride etc.) and the like can be used. Where necessary, a ligand (e.g., triphenylphosphine, tri(tert-butyl)phosphine, tri(cyclopropyl)phosphine etc.) may be added, and metal oxide (e.g., copper oxide, silver oxide etc.) and the like may be used as a cocatalyst.

While the amount of the transition metal catalyst to be used varies depending on the kind of catalyst, it is generally about 0.0001 mol-about 1 mol, preferably about 0.01 mol-about 0.5 mol, per 1 mol of compound (XXXVIII). The amount of the ligand to be used is generally about 0.0001 mol-about 4 mol, preferably about 0.01 mol-about 2 mol, per 1 mol of compound (XXXVIII). The amount of the cocatalyst to be used is generally about 0.0001 mol-about 4 mol, preferably about 0.01 mol-about 2 mol, per 1 mol of compound (XXXVIII).

Examples of the base include organic amines (e.g., trimethylamine, triethylamine, diisopropylethylamine, N-methylmorpholine, 1,8-diazabicyclo[5,4,0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), alkali metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium hexamethyl disilazide, sodium hexamethyl disilazide, potassium hexamethyl disilazide etc.) and the like. Of these, alkali metal salts such as sodium carbonate, potassium carbonate, cesium carbonate, sodium phosphate, potassium phosphate and the like; alkali metal alkoxides such as sodium tert-butoxide, potassium tert-butoxide and the like; organic amines such as triethylamine, diisopropylethylamine etc.; and the like are preferable.

The amount of the base to be used is generally about 0.1 mol-about 10 mol, preferably about 1 mol-about 5 mol, per 1 mol of compound (XXXVIII).

Examples of the solvent that does not adversely influence the reaction include hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran etc.), alcohols (e.g., methanol, ethanol etc.), aprotic polar solvents (e.g., dimethylformamide, dimethyl sulfoxide, hexamethylphosphoramide etc.), water and the like. These solvents may be used in a mixture at an appropriate ratio.

The reaction temperature is generally about −10° C. to about 200° C., preferably about 0° C. to about 150° C.

The reaction time is generally about 0.5 hr-about 48 hr, preferably about 0.5 hr-about 16 hr.

The thus-obtained compound (XXXIX) can be isolated and purified by a known separation and purification means, for example, concentration, concentration under reduced pressure, solvent extraction, crystallization, recrystallization, phase transfer, chromatography and the like.

Step 4

In this step, compound ($I_0i$) is obtained by removing the protecting group from compound (XXXIX). This step can be performed in the same manner as in the aforementioned method H, step 8.

The thus-obtained compound ($I_0i$) can be isolated and purified by a known separation and purification means, for example, concentration, concentration under reduced pressure, solvent extraction, crystallization, recrystallization, phase transfer, chromatography and the like.

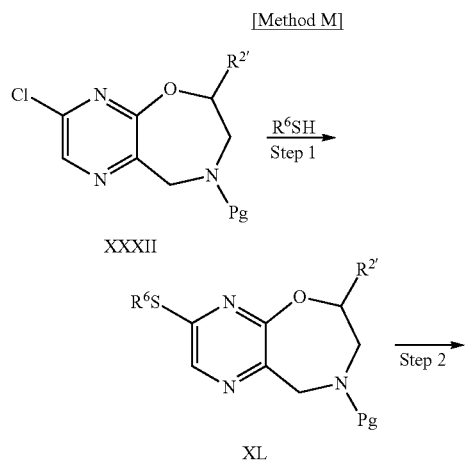

XXXII

XL

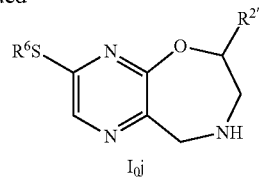

$I_0j$ wherein $R^6$ is a $C_{1-6}$ alkyl group; and other symbols are as defined above.

Step 1

In this step, compound (XL) is produced by reacting compound (XXXII) with a compound represented by $R^6$—SH (hereinafter to be abbreviated as $R^6$—SH) to be subjected to a sulfanylation reaction. While this reaction can be performed according to a method known per se, it is generally performed in the presence of a base and, where necessary, in a solvent that does not adversely influence the reaction.

The amount o $R^6$—SH to be used is generally about 0.5 mol-about 100 mol, preferably about 1 mol-about 3 mol, per 1 mol of compound (XXXII).

Examples of the base include metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate and the like; alkoxides such as sodium methoxide, sodium ethoxide etc. and the like), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridine, pyridazine, 4-dimethylaminopyridine etc.) and the like. Of these, metal hydrides such as sodium hydride and the like are preferable. While the amount of the base to be used varies depending on the kind of solvent and other reaction conditions, it is generally about 0.1 mol-about 10 mol, preferably about 1 mol-about 5 mol, per 1 mol of compound (XXXII).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.) and the like. These solvents may be used in a mixture at an appropriate ratio.

The reaction temperature is generally about −50° C. to about 300° C., preferably about 0° C. to about 200° C.

The reaction time varies depending on the kind of $R^6$—SH, reaction temperature and the like, and is generally about 0.1 hr-about 100 hr, preferably about 0.5 hr-about 36 hr.

The thus-obtained compound (XL) can be isolated and purified by a known separation and purification means such as concentration, concentration under reduced pressure, solvent extraction, crystallization, recrystallization, phase transfer, chromatography and the like.

Step 2

In this step, compound ($I_0j$) is obtained by removing the protecting group from compound (XL). This step can be performed in the same manner as in the aforementioned method D.

The thus-obtained compound ($I_0j$) can be isolated and purified by a known separation and purification means, for example, concentration, concentration under reduced pressure, solvent extraction, crystallization, recrystallization, phase transfer, chromatography and the like.

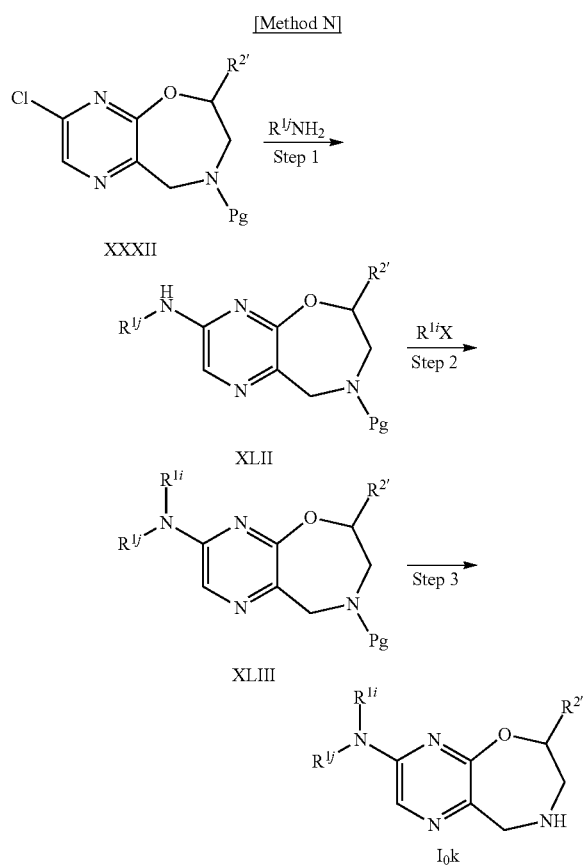

[Method N]

wherein each symbol is as defined above.
Step 1
In this step, compound (XLII) is produced by reacting compound (XXXII) with a compound represented by formula: $R^{1j}NH_2$ or a salt thereof. This step can be performed in the same manner as in the aforementioned method C, step 1, or a method analogous thereto.

The thus-obtained compound (XLII) can be isolated and purified by a known separation and purification means such as concentration, concentration under reduced pressure, solvent extraction, crystallization, recrystallization, phase transfer, chromatography and the like.
Step 2
In this step, compound (XLIII) is produced by reacting compound (XLII) with a compound represented by formula: This step can be performed in the same manner as in the aforementioned method G, step 2, or a method analogous thereto.

The thus-obtained compound (XLIII) can be isolated and purified by a known separation and purification means, for example, concentration, concentration under reduced pressure, solvent extraction, crystallization, recrystallization, phase transfer, chromatography and the like.
Step 3
In this step, compound ($I_0k$) is obtained by removing the protecting group from compound (XLIII). This step can be performed in the same manner as in the aforementioned method A, step 4.

The thus-obtained compound ($I_0k$) can be isolated and purified by a known separation and purification means, for example, concentration, concentration under reduced pressure, solvent extraction, crystallization, recrystallization, phase transfer, chromatography and the like.

Compound ($I_0$) and compound (I) can be isolated and purified by a known means, for example, phase transfer, concentration, solvent extraction, fractionation, liquid conversion, crystallization, recrystallization, chromatography and the like. When compound ($I_0$) or compound (I) is obtained as a free compound, it can be converted to an object salt according to a method known per se or a method analogous thereto. On the contrary, when it is obtained as a salt, it can be converted to a free form or other object salt according to a method known per se or a method analogous thereto.

When compound ($I_0$) or (I) contains isomers such as an optical isomer, a stereoisomer, a regioisomer and a rotamer, such isomers and a mixture thereof are also encompassed in compound ($I_0$) or (I). In addition, an isomer may be formed by conformation, and such isomers and a mixture thereof are also encompassed in compound ($I_0$) or compound (I). These isomers can be obtained as single products by a synthesis method or separation method known per se (e.g., concentration, solvent extraction, column chromatography, recrystallization, etc.). For example, when compound ($I_0$) or (I) has optical isomers, an optical isomer resolved from this compound is also encompassed in compound ($I_0$) or (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.
1) Fractional Recrystallization Method
A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.
2) Chiral Column Method
A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.
3) Diastereomer Method
A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound ($I_0$)

or (I) contains a hydroxyl group, or a primary or secondary amino group in a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers in the ester form or in the amide form, respectively. When compound ($I_0$) or (I) has a carboxyl group, this compound and an optically active amine or an optically active alcohol group are subjected to condensation reaction to give diastereomers in the amide form or in the ester form, respectively. The separated diastereomer is converted to an optical isomer of the original compound by acid hydrolysis or base hydrolysis.

Compound ($I_0$) and compound (I) may be crystals, and they are encompassed in compound ($I_0$) and compound (I) whether the crystal form is singular or a mixture of the crystal forms. The crystals of the compound ($I_0$) or (I) can be produced by crystallization of compound ($I_0$) or (I) according to crystallization methods known per se.

Examples of the crystallization method include a method of crystallization from a solution, a method of crystallization from vapor, a method of crystallization from the melts and the like.

The "method of crystallization from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two or more at a suitable ratio (e.g., 1:1 to 1:100 (a volume ratio)). Where necessary, a seed crystal can be used.

The "method of crystallization from vapor" is, for example, a vaporization method (a sealed tube method, a gas stream method), a gas phase reaction method, a chemical transportation method and the like.

The "method of crystallization from the melts" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound ($I_0$) or compound (I) in a suitable solvent (e.g., alcohols such as methanol, ethanol and the like, ethers such as diethyl ether, diisopropyl ether, tetrahydrofuran, dioxane etc., etc.) at 20° C. to 120° C., and cooling the obtained solution to a temperature (e.g., 0-50° C., preferably 0-20° C.) not higher than the dissolution temperature, and the like. In this case, a nitrogen gas and the like may be flown to evaporate the solvent.

The thus obtained crystals of compound ($I_0$) or (I) of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound ($I_0$) or (I) obtained by the above-mentioned production method (hereinafter to be abbreviated as "the crystal of the present invention") has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a pharmaceutical composition.

In the present specification, the melting point means a melting point measured using, for example, a micro melting point determination apparatus (YANACO, MP-500D), a DSC (differential scanning calorimetry) apparatus (SEIKO, EXSTAR6000) or the like.

The compound ($I_0$) and compound (I) may be pharmaceutically acceptable cocrystals or cocrystal salts. Here, the cocrystals and cocrystal salts mean crystalline substances consisting of two or more kinds of particular solids at room temperature, each having different physical properties (e.g., structure, melting point, heat of melting, hygroscopicity, solubility, stability etc.). The cocrystals and cocrystal salts can be produced by a cocrystallization method known per se.

Compound ($I_0$) and compound (I) may be used as prodrugs. A prodrug of the compound ($I_0$) or (I) means a compound which is converted to the compound ($I_0$) or (I) with a reaction due to an enzyme, an gastric acid, etc. under the physiological condition in the living body, that is, a compound which is converted to the compound ($I_0$) or (I) with oxidation, reduction, hydrolysis, etc. according to an enzyme; or a compound which is converted to the compound ($I_0$) or (I) by hydrolysis etc. due to gastric acid, etc.

A prodrug of compound ($I_0$) or (I) may be a compound obtained by subjecting an amino group in compound ($I_0$) or (I) to an acylation, alkylation or phosphorylation (e.g., a compound obtained by subjecting an amino group in compound ($I_0$) or (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxy group in compound ($I_0$) or (I) to an acylation, alkylation, phosphorylation or boration (e.g., a compound obtained by subjecting a hydroxy group in compound ($I_0$) or (I) to an acetylation, palmitoylation, propanoylation, pivaloylation, fumarylation, alanylation, dimethylaminomethylcarbonylation, etc.); a compound obtained by subjecting a carboxyl group in compound ($I_0$) or (I) to an esterification or amidation (e.g., a compound obtained by subjecting a carboxyl group in compound ($I_0$) or (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, methylamidation, etc.) and the like. Any of these compounds can be produced from compound ($I_0$) or (I) by a method known per se.

A prodrug of compound ($I_0$) or (I) may also be one which is converted to compound ($I_0$) or (I) under a physiological condition, such as those described in IYAKUHIN no KAIHATSU (Development of Pharmaceuticals), Vol. 7, Design of Molecules, p. 163-198, Published by HIROKAWA SHOTEN (1990).

Compound (I₀) or (I) or a prodrug thereof (hereinafter sometimes to be abbreviated as "the compound of the present invention" in the present specification) has a superior serotonin 5-HT$_{2C}$ receptor activating action.

Furthermore, the compound of the present invention is useful as medicament, since it has superior oral absorbability and is low toxic and safe.

Accordingly, the compound of the present invention is useful as a improving, prophylactic or therapeutic drug for all serotonin 5-HT$_{2C}$ associated diseases in mammals (e.g., human, monkey, bovine, horse, swine, mouse, rat, hamster, rabbit, cat, dog, sheep, goat and the like), for example, diseases described in (1)-(19) below:

(1) lower urinary tract diseases [for example, overactive bladder, benign prostatic hyperplasia, interstitial cystitis, chronic prostatitis, urine collection symptom (e.g., day time urinary frequency, nocturia, urinary urgency, urinary incontinence, stress urinary incontinence, urge urinary incontinence, mixed urinary incontinence, enuresis, nocturnal enuresis, overflow urinary incontinence, other urinary incontinence, enhanced, decreased or missing bladder sensation etc.), voiding symptom (e.g., weak urinary stream, split urinary stream, spraying stream, intermittent urinary stream, voiding postponement, straining at urination, terminal dribbling etc.), post-micturition symptom (e.g., sense of residual urine, post-micturition dribble etc.), symptom due to sexual intercourse (e.g., coital pain, vaginal dryness, urinary incontinence etc.), symptom due to pelvic organ prolapse (e.g., foreign body sensation, lumbago etc.), genital organ pain or lower urinary tract pain (e.g., bladder pain, urethral pain, pudendalgia, vaginodynia, scrotal pain, perineal pain, pelvic pain etc.), genital organ or urinary tract pain syndrome (e.g., bladder pain syndrome, urethral pain syndrome, pudendalgia syndrome, vaginal syndrome, scrotal pain syndrome, perineal pain syndrome, pelvic pain syndrome etc.), symptom syndrome suggesting lower urinary tract dysfunction (e.g., overactive bladder syndrome, a lower urinary tract symptom suggesting bladder outlet obstruction etc.), polyuria, urolithiasis (e.g., ureteral calculus, urethral calculus)];

(2) metabolic diseases [for example, diabetes (e.g., insulin dependent diabetes, diabetic complications, diabetic retinopathy, diabetic microangiopathy, diabetic neuropathy etc.), impaired glucose tolerance, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), benign prostatic hyperplasia, sexual dysfunction];

(3) central nervous system diseases [for example, neurodegenerative diseases (e.g., Alzheimer's disease, Down's disease, Parkinson's disease, Creutzfeldt-Jakob disease, amyotrophic lateral sclerosis (ALS), Huntington chorea, diabetic neuropathy, multiple sclerosis etc.), mental diseases (e.g., schizophrenia, depression, mania, anxiety neurosis, obsessive-compulsive neurosis, panic disorder, epilepsy, alcohol dependence, drug dependence, anxiety, anxious mental state, emotional abnormality, cyclothymia, nervous erethism, autism, faint, addiction, low sex drive etc.), central nervous system and peripheral nerve disorders (e.g., head trauma, spinal damage, brain edema, disorders of sensory function, abnormality of sensory function, disorders of autonomic nervous function, abnormality of autonomic nervous function, whiplash injury etc.), memory disorders (e.g., senile dementia, amnesia, cerebrovascular dementia etc.), cerebrovascular disorders (e.g., cerebral hemorrhage, cerebral infarction and the like and sequelae or complication thereof, asymptomatic cerebrovascular accident, transient cerebral ischemic attack, hypertensive encephalopathia, blood-brain barrier disorder, etc.), recurrence and sequelae of cerebrovascular disorders (e.g., neural symptoms, mental symptoms, subjective symptoms, disorders of daily living activities etc.), central nervous system hypofunction after brain blood vessel occlusion, disorder or abnormality of autoregulation ability of brain circulation or renal circulation, sleep disorder];

(4) sexual dysfunction diseases [for example, male erectile dysfunction, dysspermia, female sexual dysfunction];

(5) digestive organ diseases [for example, an irritable bowel syndrome, inflammatory intestine disease, ulcerative colitis, Crohn's disease, diseases caused by a spiral urease-positive gram-negative bacterium (e.g., *Helicobacter pylori*, etc.) (e.g., gastritis, gastric ulcer, etc.), gastric cancer, postgastrostomy disorder, indigestion, esophageal ulcer, pancreatitis, polyp of the colon, cholelithiasis, hemorrhoids, peptic ulcer, situational ileitis, gluttony, constipation, diarrhea, borborygmus, etc.];

(6) inflammatory or allergic diseases [for example, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitidis, inflammatory ocular disease];

(7) osteoarthropathy diseases [for example, rheumatoid arthritis (e.g., rheumatoid arthritis), arthritis deformans, rheumatoid myelitis, osteoporosis, abnormal growth of cells, bone fracture, bone refracture, osteomalacia, osteopenia, Paget's disease of bone, rigid myelitis, articular tissue destruction by gonarthrosis deformans or similar diseases thereto];

(8) respiratory diseases [for example, cold syndrome, pneumonia, asthma, pulmonary hypertension, pulmonary thrombi/pulmonary obliteration, pulmonary sarcoidosis, pulmonary tuberculosis, interstitial pneumonia, silicosis, adult respiratory distress syndrome, chronic obstructive pulmonary disease, cough];

(9) infectious diseases [for example, HIV infectious diseases, virus infectious diseases due to cytomegalo virus, influenza virus, herpes virus and the like, *rickettsia* infectious diseases, bacterial infectious diseases, sexually-transmitted diseases, carinii pneumonia, *Helicobacter pylori* infectious disease, systemic fungal infectious diseases, tuberculosis, invasive staphylococcal infectious diseases, acute viral encephalitis, acute bacterial meningitidis, AIDS encephalitis, septicemia, sepsis, sepsis gravis, septic shock, endotoxin shock, toxic shock syndromes];

(10) cancers [for example, primary, metastatic or recurrent breast cancer, prostatic cancer, pancreatic cancer, gastric cancer, lung cancer, colorectal cancers (e.g., colon cancer, rectal cancer, anal cancer), esophagus cancer, duodenal cancer, head and neck cancers (e.g., cancer of the tongue, pharynx cancer, laryngeal cancer), brain tumor, schwannoma, non-small cell lung cancer, small cell lung cancer, liver cancer, kidney cancer, cancer of the bile duct, uterine cancers (e.g., uterine body cancer, cervical cancer), ovary cancer, urinary bladder cancer, skin cancer, hemangioma, malignant lymphoma, malignant melanoma, thyroid cancer, bone tumor, vascular fibroma, retinosarcoma, penile cancer, solid cancer in childhood, Kaposi's sarcoma, Kaposi's sarcoma caused by AIDS, maxillary tumor, fibrous histiocytoma, leiomyosarcoma, rhabdomyosarcoma, liposarcoma, fibroid tumors of the uterus, osteoblastoma, osteosarcoma, chondrosarcoma, cancerous mesothelioma, tumors such as leukemia and the like, Hodgkin's disease];
(11) circulatory diseases [for example, acute coronary artery syndromes (e.g., acute myocardial infarction, unstable angina, etc.), peripheral arterial occlusion, Raynaud's disease, Buerger's disease, restenosis after coronary-artery intervention (e.g., percutaneous transluminal coronary angioplasty (PTCA), directional coronary atherectomy (DCA), stenting, etc.), restenosis after coronary-artery bypass operation, restenosis after intervention (e.g., angioplasty, atherectomy, stenting, etc.) or bypass operation in other peripheral artery, ischemic cardiac diseases (e.g., myocardial infarction, angina, etc.), myocarditis, intermittent claudication, lacunar infarction, arteriosclerosis (e.g., atherosclerosis, etc.), cardiac failure (e.g., acute cardiac failure, chronic cardiac failure including congestive cardiac failure), arrhythmia, progress of atherosclerotic plaque, thrombosis, hypertension, hypertensive tinnitus, hypotension];
(12) pains [e.g., headache, migraine, neuralgia, pelvic organ pain (including bladder pain)];
(13) autoimmune diseases [for example, collagen disease, systemic lupus erythematosus, scleroderma, polyarteritis, myasthenia gravis, multiple sclerosis, Sjogren's syndrome, Behcet's disease];
(14) hepatic diseases [for example, hepatitis (including chronic hepatitis), cirrhosis, interstitial hepatic disease];
(15) pancreatic diseases [for example, pancreatitis (including chronic pancreatitis)];
(16) renal diseases [for example, nephritis, glomerulonephritis, glomerulosclerosis, renal failure, thrombotic microangiopathy, dialysis complications, organ disorders including nephropathia by radiation, diabetic nephropathy];
(17) endocrine diseases [for example, Addison's disease, Cushing's syndrome, melanocytoma, primary aldosteronism];
(18) gynecologic diseases [for example, organ prolapse (e.g., pelvic organ prolapse, genital prolapse, bladder prolapse, rectal prolapse, urethral prolapse, urethral hypermobility, enteroceles, rectoceles, cystoceles, laceration of perineal body, pelvic floor hernia etc.), climacteric disorder, gestational toxicosis, endometriosis, hysteromyoma, ovarian disease, mammary disease, premenstrual syndrome and the like]; and
(19) other diseases [for example,
(a) transplant rejection (e.g., posttransplantational rejection, posttransplantational polycythemia, hypertension, organ disorder, vascular hypertrophy or graft-versus-host disease),
(b) abnormality in characteristic of blood and/or blood components (e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy),
(c) dermatic diseases (e.g., keloid, hemangioma, psoriasis, pruritus),
(d) ophthalmic diseases (e.g., glaucoma, ocular hypertension disease),
(e) otolaryngological diseases (e.g., Menuel syndrome, tinnitus, gustation disorder, dizziness, disequilibrium, dysphagia),
(f) diseases due to environmental and/or occupational factors (e.g., radiation disorder, disorders by ultraviolet ray/infrared ray/laser ray, altitude sickness),
(g) ataxia, stiffness, tremor, motion impairment, akinesia,
(h) chronic fatigue syndrome,
(i) sudden infant death syndrome,
(j) hiccup, and
(k) diseases causing palpitation, vertigo, heartburn or the like.

The compound of the present invention is particularly useful as a serotonin 5-$HT_{2C}$ receptor activator, a drug for the improvement, prophylaxis or treatment of lower urinary tract symptoms, a drug for the prophylaxis or treatment of obesity, and a drug for the prophylaxis or treatment of organ prolapse. When the lower urinary tract symptom is a target disease, the compound of the present invention is particularly useful as a drug for the improvement, prophylaxis or treatment of stress urinary incontinence.

A medicament containing the compound of the present invention (hereinafter to be abbreviated as "the medicament of the present invention") may be a preparation with any form such as tablet (including sugar-coated tablet, film-coated tablet, sublingual tablet, orally disintegrating tablet, buccal tablet, and the like), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, films (e.g., orally disintegrable films, mouth cavity mucous membrane patch film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like.

The medicament of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the preparation of the present invention may be formed into a sustained-release preparation containing an active ingredient and a biodegradable polymer compound. The sustained-release preparation can be produced according to the method described in JP-A-9-263545.

In the medicament of the present invention, while the content of the compound of the present invention varies depending on the form of the preparation, it is generally 0.01-100 wt %, preferably 0.1-50 wt %, more preferably about 0.5-20 wt %, relative to the whole preparation.

The compound of the present invention may be used alone as the medicament of the present invention, or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by ordinary methods. It can be safely administered orally or parenterally (e.g., intravenous, intramuscular, subcutaneous, intraorgan, intranasal, intradermal, instillation, intracerebral, intrarectal, vaginal, intraperitoneal and intratumor administrations, administration to the vicinity of tumor etc., and direct administration to the lesion). The medicament of the present invention can also be formed as a preparation for topical administration and directly administered to the affected part of an articular disease. In this case, an injection is preferable.

For formulation into an injection, for example, the compound of the present invention is formulated into an aqueous suspension with a dispersing agent (e.g., surfactants such as Tween 80, HCO60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound of the present invention together with vegetable oil such as sesame oil, corn oil and the like or a mixture thereof with a phospholipid such as lecithin and the like, or medium-chain triglyceride (e.g., miglyol 812 etc.) to give an injection to be actually used.

The compound of the present invention can be used along with other medicament.

As a drug that can be blended or combined with the compound of the present invention (hereinafter to be abbreviated as concomitant drug), the following drugs and the like can be used.

(1) Other Drugs for Treating Stress Urinary Incontinence

Adrenaline α1 receptor agonists (e.g., ephedrine hydrochloride, midodrine hydrochloride), adrenaline β2 receptor agonists (e.g., Clenbuterol), noradrenaline reuptake inhibitors, noradrenaline and serotonin reuptake inhibitors (e.g., duloxetine), tricyclic antidepressants (e.g., imipramine hydrochloride), anticholinergic agents or smooth muscle stimulants (e.g., oxybutynin hydrochloride, propiverine hydrochloride, celimeverine hydrochloride), female hormone drugs (e.g., conjugated estrogen (premarin), estriol) and the like.

(2) Agents for Treating Diabetes

Insulin preparations [e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1, etc.) and the like], insulin sensitizers (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., vildagliptin, sitagliptin, saxagliptin, alogliptin, NVP-DPP-728, PT-100, P32/98, etc.), 03 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.) and the like.

(3) Agents for Treating Diabetic Complications

Aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapride, etc.) and the like.

(4) Antihyperlipidemic Agents

Statin compounds inhibiting cholesterol synthesis (e.g., pravastatin, simvastatin, lovastatin, atorvastatin, fluvastatin, cerivastatin or their salt (e.g., sodium salt, etc.), etc.), squalene synthase inhibitors, fibrate compounds having triglyceride lowering action (e.g., bezafibrate, clofibrate, simfibrate, clinofibrate, etc.) and the like.

(5) Hypotensive Agents

Angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine, and the like.

(6) Antiobesity Agents

Antiobesity drugs acting on the central nervous system (e.g. dexfenfluramine, fenfluramine, phentermine, sibutramine, anfepramone, dexamphetamine, mazindol, phenylpropanolamine, clobenzorex, etc.), pancreatic lipase inhibitors (e.g. orlistat, etc.), β3 agonists (e.g. CL-316243, SR-58611-A, UL-TG-307, AJ-9677, AZ40140, etc.), anorectic peptides (e.g. leptin, CNTF (Ciliary Neurotrophic Factor), etc.), cholecystokinin agonists (e.g. lintitript, FPL-15849, etc.) and the like.

(7) Diuretic Agents

Xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide, etc.

(8) Chemotherapeutic Agents

Alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as Furtulon and Neo-Furtulon are preferred.

(9) Immunotherapeutic Agents

Microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating factors (e.g., granulocyte colony stimulating factor, erythropoietin, etc.) and the like. Among these, IL-1, IL-2 and IL-12 are preferred.

(10) Therapeutic Agents Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above references are applied to both), fat metabolism ameliorating drugs (e.g., eicosapentaenoic acid etc.) [British Journal of Cancer, vol. 68, pp. 314-318, 1993], growth hormones, IGF-1, antibodies to the cachexia-inducing factors such as TNF-α, LIF, IL-6 and oncostatin M, and the like.

(11) Antiinflammatory Agents

Steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.) and the like.

In addition, in another embodiment, $R^{1'}$ is preferably a morpholino group optionally substituted by $C_{1-6}$ alkyl group(s), a di($C_{1-6}$ alkyl)amino group, a $C_{1-6}$ alkoxy group optionally substituted by $C_{3-6}$ cycloalkyl group(s), a $C_{3-6}$ cycloalkyl group or a $C_{3-6}$ cycloalkenyl group.

(12) Miscellaneous

Glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatriptan), serotonin receptor antagonists (e.g., cyproheptadine hydrochloride, ondansetron), serotonin uptake inhibitors (e.g., fluvoxamine maleate, fluoxetine, paroxetine), hypnotics (e.g., triazolam, zolpidem), anticholinergic agents, $\alpha_1$ receptor blocking agents (e.g., tamsulosin, silodosin, naftopidil), muscle relaxants (e.g., baclofen), potassium channel openers (e.g., nicorandil), calcium channel blocking agents (e.g., nifedipine), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists (e.g., piperidine derivatives (GR159897, GR149861, SR48968(saredutant), SR144190, YM35375, YM38336, ZD7944, L-743986, MDL105212A, ZD6021, MDL105172A, SCH205528, SCH62373, R-113281 etc.), perhydroisoindole derivatives (e.g., RPR-106145 etc.), quinoline derivatives (e.g., SB-414240 etc.), pyrrolopyrimidine derivatives (e.g., ZM-253270 etc.), pseudopeptide derivatives (e.g., MEN11420(nepadutant), SCH217048, L-659877, PD -147714(CAM-2291), MEN10376, S16474 etc.), the others (GR100679, DNK333, GR94800, UK-224671, MEN10376, MEN10627), or a salt thereof etc.), agents of treating HIV infection (e.g., saquinavir, zidovudine, lamivudine, nevirapine), agents of treating chronic obstructive pulmonary diseases (e.g., salmeterol, thiotropium bromide, cilomilast), etc.

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin hydrochloride, tolterodine tartrate, etc.) and the like, preferably, oxybutynin, propiverine, darifenacin, tolterodine, temiverine, trospium chloride or a salt thereof (e.g., oxybutynin hydrochloride, tolterodine tartrate, etc.). In addition, acetylcholinesterase inhibitors (e.g., distigmine, etc.) and the like can be used.

As the noradrenaline reuptake inhibitor, for example, Betanidine, Tesofensine, Trodusquemine, PSN-602 and the like can be used. As the noradrenaline and serotonin reuptake inhibitor, for example, duloxetine, venlafaxine and the like can be used.

In a combination of the compound of the present invention and the concomitant drug, the administration time of the compound of the present invention and the concomitant drug is not restricted, and the compound of the present invention or a pharmaceutical composition thereof and the concomitant drug or a pharmaceutical composition thereof can be administered to the administration subject simultaneously, or may be administered at different times. The dosage of the concomitant drug may be determined according to the dose clinically used, and can be appropriately selected depending on the administration subject, administration route, disease, combination and the like.

The concomitant administration mode is not particularly restricted, and it is sufficient that the compound of the present invention and the concomitant drug are combined in administration. Examples of such administration mode include the following methods:

(1) The compound of the present invention and the concomitant drug are simultaneously produced to give a single preparation which is administered.

(2) The compound of the present invention and the concomitant drug are separately produced to give two kinds of preparations which are administered simultaneously by the same administration route.

(3) The compound of the present invention and the concomitant drug are separately produced to give two kinds of preparations which are administered by the same administration route at different times.

(4) The compound of the present invention and the concomitant drug are separately produced to give two kinds of preparations which are administered simultaneously by different administration routes.

(5) The compound of the present invention and the concomitant drug are separately produced to give two kinds of preparations which are administered by different administration routes at different times (e.g., the compound of the present invention; the concomitant drug are administered in this order, or in the reverse order).

In a medicament using the compound of the present invention and a concomitant drug in combination (hereinafter to be abbreviated as "the combination agent of the present invention"), the mixing ratio of the compound of the present invention and the concomitant drug can be appropriately determined according to the subject of administration, administration route, disease and the like.

For example, while the content of the compound of the present invention in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the concomitant drug in the combination agent of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the additive such as a carrier and the like in the combination agent of the present invention varies depending on the form of the preparation, it is generally about 1 to about 99.99 wt %, preferably about 10 to about 90 wt %, relative to the whole preparation.

Similar contents can be employed when the compound of the present invention and the concomitant drug are independently formulated.

While the dose varies depending on the kind of the compound of the present invention or a pharmaceutically acceptable salt thereof, administration route, symptom, age of patients and the like, for example, for oral administration to an adult patient with stress urinary incontinence, obesity and/or pelvic organ prolapse, it is about 0.005 to 50 mg, preferably about 0.05 to 10 mg, more preferably about 0.2 to 4 mg/kg body weight/day, which can be administered in 1 to about 3 portions.

When the combination agent of the present invention is a sustained-release preparation, the dose varies depending on the kind and content of the compound of the present invention, dosage form, period of sustained drug release, subject animal of administration (e.g., mammals such as human, rat, mouse, cat, dog, rabbit, bovine, swine and the like) and administration object. For parenteral administration, for example, about 0.1 to about 100 mg of the compound of the present invention only needs to be released in one week from the administered preparation.

The dose of the concomitant drug may be set within the range such that it causes no problems of side effects. The daily dose as the concomitant drug varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of drugs is usually in the order of about 0.001 to 2000 mg, preferably about 0.01 to 500 mg, and more preferably about 0.1 to 100 mg, per 1 kg body weight of mammals, which may be administered once a day or in two to four divided portions a day.

When administering the combination agent of the present invention, the compound of the present invention and the concomitant drug may be simultaneously administered, or administered in a staggered manner. In case of staggered administration, the time interval varies depending on the active ingredients to be administered, a formulation and an administration route. For example, when the concomitant drug is administered first, the compound of the present invention may be administered 1 minute to 3 days, preferably 10 minutes to 1 day, more preferably 15 minutes to 1 hour, after administration of the concomitant drug. When the compound of the present invention is administered first, the concomitant drug may be administered 1 minute to 1 day, preferably 10 minutes to 6 hours, more preferably 15 minutes to 1 hour, after administration of the compound of the present invention.

The medicament of the present invention is low toxic and can be used safely. Particularly, the following Example compounds are superior in the absorbability by oral administration, and can be advantageously used for an oral preparation.

EXAMPLES

The present invention is further described in detail with Reference Examples, Examples, Formulation Examples and Experimental Examples which are not intended to restrict the invention and may be modified without departing from the scope of the invention.

In Reference Examples and Examples, column chromatography was performed using Purif-8 or Purif-α2 manufactured by MORITEX and under observation by a UV detector. The silica gel used for column chromatography was Purif-Pack manufactured by MORITEX. The room temperature generally means a temperature of from about 10° C. to 30° C.

The abbreviations in Examples and Reference Examples mean the following.

LC: liquid chromatography
MS: mass spectrometry spectrum
ESI: electrospray method
m/z: molecular ion peak
NMR: nuclear magnetic resonance spectrum
Hz: hertz
J: coupling constant
m: multiplet
q: quartet
t: triplet
d: doublet
dd: double doublet
s: singlet
br: broad
dt: double triplet
dq: double quartet
td: triple doublet
brs: broad singlet
Ac: acetyl group
$^t$Bu: tert-butyl group
Boc: tert-butyloxycarbonyl group
Et: ethyl group
Ph: phenyl group
N: normal concentration
$CDC1_3$: deuterated chloroform
DMF: N,N-dimethylformamide
THF: tetrahydrofuran
DMSO: dimethyl sulfoxide
DMA: N,N-dimethylacetamide
DME: dimethoxyethane
TFA: trifluoroacetic acid
$Boc_2O$: di-tert-butyl dicarbonate
XPhos: dicyclohexyl(2',4',6'-triisopropylbiphenyl-2-yl)phosphine
$Pd_2(dba)_3$: tris(dibenzylideneacetone)dipalladium(0)
10% Pd/C: 10% palladium/carbon
20% $Pd(OH)_2$/C: 20% palladium hydroxide/carbon
BINAP : 2,2'-bis(di-phenylphosphino)-1,1'-binaphthyl LC-MS in Examples and Reference Examples was measured under the following conditions.
Analysis by LC-MS
  measurement device: Waters LC-MS system
  HPLC: Agilent HP1100
  MS: Micromass ZQ
HPLC conditions
  column: CAPCELL PAK C18UG120, S-3 μm, 1.5×35 mm (Shiseido Co., Ltd.)
  solvent: SOLUTION A; 0.05% trifluoroacetic acid-containing water, SOLUTION B; 0.05% trifluoroacetic acid-containing acetonitrile
  gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.60 min (SOLUTION A/SOLUTION B=90/10)

injection volume: 2 μL, flow rate: 0.5 mL/min, detection method: UV220 nm
MS conditions
ionization method: ESI
Purification by preparative HPLC in Examples and Reference Examples was performed under the following conditions.
device: Gilson Inc. High-Throughput Purification System
column: CombiPrep ODS-A S-5 μm, 50×20 mm (YMC)
solvent: SOLUTION A; 0.1% trifluoroacetic acid-containing water, SOLUTION B; 0.1% trifluoroacetic acid-containing acetonitrile
gradient cycle: 0.00 min (SOLUTION A/SOLUTION B=95/5), 1.00 min (SOLUTION A/SOLUTION B=95/5), 5.20 min (SOLUTION A/SOLUTION B=5/95), 6.40 min (SOLUTION A/SOLUTION B=5/95), 6.50 min (SOLUTION A/SOLUTION B=95/5), 6.60 min (SOLUTION A/SOLUTION B=95/5)
flow rate: 25 mL/min, detection method: UV220 nm
Purification by high-resolution preparative HPLC in the following Examples were carried out under the following conditions.
instrument: Gilson high-throughput purification system
column: Combiprep Hydrosphere C18, 50×20 mm (YMC)
solvent: SOLUTION A; water containing 0.1% trifluoroacetic acid, SOLUTION B; acetonitrile containing 0.1% trifluoroacetic acid
gradient cycle: 0.00 min (SOLUTION A/SOLUTION B=98/2), 1.00 min (SOLUTION A/SOLUTION B=98/2), 5.20 min (SOLUTION A/SOLUTION B=60/40), 5.40 min (SOLUTION A/SOLUTION B=5/95), 6.40 min (SOLUTION A/SOLUTION B=5/95), 6.50 min (SOLUTION A/SOLUTION B=98/2), 6.60 min (SOLUTION A/SOLUTION B=98/2)
flow rate: 20 mL/min, detection method: UV 220 nm
Powder X ray crystal diffraction in Examples was performed under the following conditions.
measurement device: Rigaku corporation, RINT Ultima$^+$ 2100
radiation source: Cu—$K_\alpha$, radiation ($\lambda$=1.5418 Å)
tube voltage: 40 kV
tube current: 50 mA
scan speed: 6°/min
diffraction angle (2θ): 2-35°

Reference Example 1

2-{benzyl[(3,5-dichloropyrazin-2-yl)methyl]amino}ethanol

To a solution of 3,5-dichloropyrazine-2-carbaldehyde (1.194 g), N-benzylethanolamine (1.02 g) and acetic acid (2.0 mL) in THF (50 mL) was added sodium triacetoxyborohydride (2.87 g), and the mixture was stirred at room temperature overnight. The reaction solution was diluted with ethyl acetate, and basified with saturated aqueous sodium hydrogen carbonate. The organic layer was separated, washed with water and saturated brine, dried over anhydrous magnesium sulfate, and concentrated under reduced pressure. The obtained residue was purified by basic silica gel column chromatography (solvent gradient: 5→25% ethyl acetate/hexane) to give the title compound (1.47 g, 70%) as a colorless oil.

$^1$H-NMR (CDCl$_3$): δ2.77-2.89 (M, 2H), 3.42 (brs, 1H), 3.63 (t, J=4.90 Hz, 2H), 3.80 (s, 2H), 3.95 (s, 2H), 7.17-7.36 (M, 5H), 8.46 (s, 1H)
ESI-MS: 312 (M+H)$^+$.

Reference Example 2

8-benzyl-3-chloro-6,7,8,9-tetrahydropyrazino[2,3-f][1,4]oxazepine

To a solution of 2-{benzyl[(3,5-dichloropyrazin-2-yl)methyl]amino}ethanol (3.425 g) in THF (100 mL) was added potassium tert-butoxide (1.48 g) under ice-cooling, and the mixture was stirred for 1 hr under ice-cooling. Water was added, and the mixture was extracted with ethyl acetate. The organic layer was washed with water and saturated brine, dried over anhydrous magnesium sulfate, and concentrated under reduced pressure. The obtained residue was purified by basic silica gel column chromatography (solvent gradient: 5→25% ethyl acetate/hexane) to give the title compound (2.59 g, 86%) as a pale-yellow oil.

$^1$H-NMR (CDCl$_3$): δ3.00-3.17 (M, 2H), 3.75 (s, 2H), 4.01 (s, 2H), 4.25-4.35 (M, 2H), 7.27-7.39 (M, 5H), 8.23 (s, 1H)
ESI-MS: m/z 276 (M+H)$^+$.

Reference Example 3

(2S)-1-{benzyl[(3,5-dichloropyrazin-2-yl)methyl]amino}propan-2-ol

To a solution of 3,5-dichloropyrazine-2-carbaldehyde (3.0 g), (2S)-1-(benzylamino)propan-2-ol (3.36 g) and acetic acid (4.9 mL) in THF (50 mL) was added sodium triacetoxyborohydride (7.18 g), and the mixture was stirred at room temperature overnight. The reaction solution was diluted with ethyl acetate, and basified with saturated aqueous sodium hydrogen carbonate. The organic layer was separated, washed with water and saturated brine, dried over anhydrous magnesium sulfate, and concentrated under reduced pressure. The obtained residue was purified by basic silica gel column chromatography (solvent gradient: 5→25% ethyl acetate/hexane) to give the title compound (3.48 g, 63%) as a pale-yellow oil.

ESI-MS: m/z 326 (M+H)$^+$.

Reference Example 4

(6S)-8-benzyl-3-chloro-6-methyl-6,7,8,9-tetrahydropyrazino[2,3-f][1,4]oxazepine

To a solution of (2S)-1-{benzyl[(3,5-dichloropyrazin-2-yl)methyl]amino}propan-2-ol (3.48 g) in THF (50 mL) was added sodium hydride (513 mg) under ice-cooling, and the mixture was stirred for 2 hr under ice-cooling. Water was added, and the mixture was extracted with ethyl acetate. The organic layer was washed with water and saturated brine, dried over anhydrous magnesium sulfate, and concentrated under reduced pressure. The obtained residue was purified by basic silica gel column chromatography (solvent gradient: 5→20% ethyl acetate/hexane) to give the title compound (1.60 g, 52%) as a pale-yellow oil.

$^1$H-NMR (CDCl$_3$): δ1.40 (d, J=6.44 Hz, 3H), 2.86-3.03 (M, 2H), 3.74 (s, 2H), 3.84-3.95 (M, 1H), 4.04-4.13 (M, 1H), 4.28-4.52 (m, 1H), 7.03-7.46 (M, 5H), 8.21 (s, 1H)
ESI-MS: m/z 290 (M+H)$^+$.

Reference Example 5

8-benzyl-3-cyclopropyl-6,7,8,9-tetrahydropyrazino[2,3-f][1,4]oxazepine

A suspension of 8-benzyl-3-chloro-6,7,8,9-tetrahydropyrazino[2,3-f][1,4]oxazepine (493 mg), cyclopropylboronic acid (280 mg), palladium acetate (20 mg), tricyclopropylphosphine (51 mg) and potassium tert-butoxide (663 mg) in toluene (8 mL) was stirred under an argon atmosphere with heating at 100° C. for 2 hr. Water was added to the reaction mixture, the aqueous layer was extracted with ethyl acetate, and the organic layer was washed with saturated brine, dried over anhydrous magnesium sulfate, and concentrated under reduced pressure. The obtained residue was purified by silica gel column chromatography (solvent gradient: 5→25% ethyl acetate/hexane) to give the title compound (79.9 mg, 16%) as a colorless oil.

ESI-MS: m/z 282 (M+H)$^+$.

Reference Example 6

8-benzyl-3-(cyclopent-1-en-1-yl)-6,7,8,9-tetrahydropyrazino[2,3-f][1,4]oxazepine A solution of 8-benzyl-3-chloro-6,7,8,9-tetrahydropyrazino[2,3-f][1,4]oxazepine (559 mg), cyclopent-1-en-1-ylboronic acid (273 mg), tetrakis(triphenylphosphine)palladium(0) (118 mg) and aqueous sodium carbonate solution (2M, 2 mL) in DME (10 mL) was stirred under an argon atmosphere with heating at 100° C. for 2 hr. Water was added to the reaction mixture, the aqueous layer was extracted with ethyl acetate, and the organic layer was washed with saturated brine, dried over anhydrous magnesium sulfate, and concentrated under reduced pressure. The obtained residue was purified by basic silica gel column chromatography (solvent gradient: 5→50% ethyl acetate/hexane) to give the title compound (424 mg, 68%) as a colorless oil.

$^1$H-NMR (CDCl$_3$): δ2.05 (quintet, 2H), 2.50-2.69 (M, 2H), 2.70-2.88 (M, 2H), 3.00-3.15 (M, 2H), 3.74 (s, 2H), 4.02 (s, 2H), 4.20-4.39 (M, 2H), 6.61-6.78 (M, 1H), 7.12-7.47 (M, 5H), 8.28 (s, 1H)

ESI-MS: m/z 308 (M+H)$^+$.

Reference Example 7

8-benzyl-3-(1-methylethoxy)-6,7,8,9-tetrahydropyrazino[2,3-f][1,4]oxazepine

To a solution of isopropanol (83 μL) in toluene (2 mL) was added sodium hydride (87 mg) at room temperature, and the mixture was stirred for 15 min. A solution of 8-benzyl-3-chloro-6,7,8,9-tetrahydropyrazino[2,3-f][1,4]oxazepine (297 mg) and BINAP (30 mg) in toluene (2 mL) was added to the reaction mixture. After substitution with an argon gas, Pd$_2$(dba)$_3$ (20 mg) was added, and the mixture was stirred under an argon atmosphere at 100° C. for 1 hr. Water was added to the reaction solution, and the mixture was extracted with ethyl acetate. The organic layer was washed with water and saturated brine and dried, and the solvent was evaporated under reduced pressure. The residue was purified by basic silica gel column chromatography (solvent gradient; 5→50% ethyl acetate/hexane) to give the title compound (137 mg, 42%) as a colorless oil.

$^1$H-NMR (CDCl$_3$): δ1.35 (d, J=6.06 Hz, 6H), 2.91-3.11 (M, 2H), 3.73 (s, 2H), 3.96 (s, 2H), 4.19-4.35 (M, 2H), 5.26 (septet, J=6.18 Hz, 1H), 7.12-7.45 (M, 5H), 7.82 (s, 1H)

ESI-MS: m/z 300 (M+H)$^+$.

Reference Example 8

8-benzyl-3-[(1R)-1-cyclopropylethoxy]-6,7,8,9-tetrahydropyrazino[2,3-f][1,4]oxazepine To a solution of (1R)-1-cyclopropylethanol (130 mg) in toluene (3 mL) was added sodium hydride (120 mg), and the mixture was stirred under a nitrogen atmosphere at room temperature for 15 min. A mixture of 8-benzyl-3-chloro-6,7,8,9-tetrahydropyrazino[2,3-f][1,4]oxazepine (415 mg), BINAP (41 mg), Pd$_2$(dba)$_3$ (28 mg) and toluene (3 mL) was added, and the mixture was stirred under an argon atmosphere at 100° C. for 3 hr. Water was added to the reaction solution, and the resultant product was extracted with ethyl acetate. The organic layer was washed with water and saturated brine and dried, and the solvent was evaporated under reduced pressure. The residue was purified by basic silica gel column chromatography (solvent gradient; 5→50% ethyl acetate/hexane) to give the title compound (329 mg, 67%) as a yellow oil.

$^1$H-NMR (CDCl$_3$): δ0.25-0.35 (M, 1H), 0.36-0.48 (M, 1H), 0.48-0.60 (m, 1H), 1.02-1.20 (M, 1H), 1.39 (d, J=6.06 Hz, 3H), 2.91-3.13 (m, 2H), 3.73 (s, 2H), 3.96 (s, 2H), 4.19-4.30 (M, 2H), 4.59 (dq, J=8.52, 6.25 Hz, 1H), 7.09-7.43 (M, 5H), 7.86 (s, 1H)

ESI-MS: m/z 326 (M+H)$^+$.

Reference Example 9

8-benzyl-3-(morpholin-4-yl)-6,7,8,9-tetrahydropyrazino[2,3-f][1,4]oxazepine

A suspension of 8-benzyl-3-chloro-6,7,8,9-tetrahydropyrazino[2,3-f][1,4]oxazepine (322 mg), morpholine (0.13 mL), Pd$_2$(dba)$_3$ (22 mg), XPhos (45 mg) and sodium tert-butoxide (282 mg) in toluene (10 mL) was stirred under an argon atmosphere at 100° C. for 3 hr. Water was added to the reaction mixture, the aqueous layer was extracted with ethyl acetate, and the organic layer was washed with saturated brine, dried over anhydrous magnesium sulfate, and concentrated under reduced pressure. The obtained residue was purified by silica gel column chromatography (solvent gradient: 16→100% ethyl acetate/hexane) to give the title compound (259 mg, 68%) as a colorless oil.

$^1$H-NMR (CDCl$_3$): δ2.97-3.08 (M, 2H), 3.47-3.58 (M, 4H), 3.72 (s, 2H), 3.77-3.87 (M, 4H), 3.93 (s, 2H), 4.17-4.32 (M, 2H), 7.17-7.41 (M, 5H), 7.74 (s, 1H)

ESI-MS: m/z 327 (M+H)$^+$.

Reference Example 10

8-benzyl-3-[(3R)-3-methylmorpholin-4-yl]-6,7,8,9-tetrahydropyrazino[2,3-f][1,4]oxazepine A suspension of 8-benzyl-3-chloro-6,7,8,9-tetrahydropyrazino[2,3-f][1,4]oxazepine (208 mg), (3R)-3-methylmorpholine (115 mg), Pd$_2$(dba)$_3$ (21 mg), XPhos (44 mg) and sodium tert-butoxide (145 mg) in toluene (5 mL) was stirred under an argon atmosphere with heating at 100° C. for 3 hr. Water was added to the reaction mixture, the aqueous layer was extracted with ethyl acetate, and the organic layer was washed with saturated brine, dried over anhydrous magnesium sulfate, and concentrated under reduced pressure. The obtained residue was purified by basic silica gel column chromatography (solvent gradient: 9→50% ethyl acetate/hexane) to give the title compound (126 mg, 60%) as a pale-yellow oil.
$^1$H-NMR (CDCl$_3$): δ1.28 (d, J=6.82 Hz, 3H), 2.97-3.05 (M, 2H), 3.25 (td, J=12.49, 3.79 Hz, 1H), 3.60 (td, J=11.74, 3.03 Hz, 1H), 3.73 (s, 2H), 3.74-3.86 (m, 3H), 3.92 (s, 2H), 4.00 (dd, J=11.36, 3.79 Hz, 1H), 4.20-4.34 (M, 3H), 7.27-7.37 (M, 5H), 7.69 (s, 1H)
ESI-MS: m/z 341 (M+H)$^+$.

Reference Example 11

(6S)-8-benzyl-6-methyl-3-(morpholin-4-yl)-6,7,8,9-tetrahydropyrazino[2,3-f][1,4]oxazepine A suspension of (6S)-8-benzyl-3-chloro-6-methyl-6,7,8,9-tetrahydropyrazino[2,3-f][1,4]oxazepine (301 mg), morpholine (0.11 mL), Pd$_2$(dba)$_3$ (19 mg), XPhos (40 mg) and sodium tert-butoxide (250 mg) in toluene (5 mL) was stirred under an argon atmosphere with heating at 100° C. for 2 hr. Water was added to the reaction mixture, the aqueous layer was extracted with ethyl acetate, and the organic layer was washed with saturated brine, dried over anhydrous magnesium sulfate, and concentrated under reduced pressure. The obtained residue was purified by basic silica gel column chromatography (solvent gradient: 9→50% ethyl acetate/hexane) to give the title compound (70 mg, 20%) as a colorless oil.
$^1$H-NMR (CDCl$_3$): δ1.37 (d, J=6.06 Hz, 3H), 2.77-3.00 (M, 2H), 3.48-3.58 (M, 4H), 3.71 (s, 2H), 3.78-3.89 (M, 5H), 3.96-4.05 (m, 1H), 4.27-4.42 (M, 1H), 7.27-7.36 (M, 5H), 7.72 (s, 1H)
ESI-MS: m/z 341 (M+H)$^+$.

Reference Example 12

(6S)-8-benzyl-6-methyl-3-[(3R)-3-methylmorpholin-4-yl]-6,7,8,9-tetrahydropyrazino[2,3-f][1,4]oxazepine A suspension of (6S)-8-benzyl-3-chloro-6-methyl-6,7,8,9-tetrahydropyrazino[2,3-f][1,4]oxazepine (313 mg), (3R)-3-methylmorpholine (164 mg), Pd$_2$(dba)$_3$ (30 mg), XPhos (62 mg) and sodium tert-butoxide (208 mg) in toluene (5 mL) was stirred under an argon atmosphere with heating at 100° C. for 3 hr. Water was added to the reaction mixture, the aqueous layer was extracted with ethyl acetate, and the organic layer was washed with saturated brine, dried over anhydrous magnesium sulfate, and concentrated under reduced pressure. The obtained residue was purified by basic silica gel column chromatography (solvent gradient: 9→50% ethyl acetate/hexane) to give the title compound (233 mg, 61%) as a pale-yellow oil.
$^1$H-NMR (CDCl$_3$): δ1.27 (d, J=6.78 Hz, 3H), 1.37 (d, J=6.78 Hz, 3H), 2.78-2.98 (M, 2H), 3.25 (td, J=12.43, 3.77 Hz, 1H), 3.59 (td, J=11.68, 3.01 Hz, 1H), 3.69-3.79 (M, 4H), 3.83 (d, J=14.69 Hz, 2H), 3.93-4.04 (M, 2H), 4.21-4.40 (M, 2H), 7.28-7.35 (M, 5H), 7.66 (s, 1H)
ESI-MS: m/z 355 (M+H)$^+$.

Reference Example 13

8-benzyl-N-methyl-N-(1-methylethyl)-6,7,8,9-tetrahydropyrazino[2,3-f][1,4]oxazepin-3-amine A suspension of 8-benzyl-3-chloro-6,7,8,9-tetrahydropyrazino[2,3-f][1,4]oxazepine (498 mg), N-methylpropan-2-amine (0.29 mL), Pd$_2$(dba)$_3$ (50 mg), XPhos (104 mg) and sodium tert-butoxide (348 mg) in toluene (5 mL) was stirred under an argon atmosphere with heating at 100° C. for 3 hr. Water was added to the reaction mixture, the aqueous layer was extracted with ethyl acetate, and the organic layer was washed with saturated brine, dried over anhydrous magnesium sulfate, and concentrated under reduced pressure. The obtained residue was purified by basic silica gel column chromatography (solvent gradient: 9→50% ethyl acetate/hexane), and further by preparative HPLC to give the title compound (79 mg, 14%) as a pale-yellow oil.
$^1$H-NMR (CDCl$_3$): δ1.18 (d, J=6.78 Hz, 6H), 2.87 (s, 3H), 2.95-3.12 (M, 2H), 3.72 (s, 2H), 3.91 (s, 2H), 4.18-4.30 (M, 2H), 4.76 (quintet, J=6.78 Hz, 1H), 7.15-7.42 (M, 5H), 7.63 (s, 1H)
ESI-MS: m/z 313 (M+H)$^+$.

Reference Example 14

8-benzyl-3-[(3R)-3-ethylmorpholin-4-yl]-6,7,8,9-tetrahydropyrazino[2,3-f][1,4]oxazepine A suspension of 8-benzyl-3-chloro-6,7,8,9-tetrahydropyrazino[2,3-f][1,4]oxazepine (308 mg), (3R)-3-ethylmorpholine (193 mg), Pd$_2$(dba)$_3$ (31 mg), XPhos (64 mg) and sodium tert-butoxide (216 mg) in toluene (6 mL) was stirred under an argon atmosphere with heating at 100° C. for 2 hr. Water was added to the reaction mixture, the aqueous layer was extracted with ethyl acetate, and the organic layer was washed with saturated brine, dried over anhydrous magnesium sulfate, and concentrated under reduced pressure. The obtained residue was purified by basic silica gel column chromatography (solvent gradient: 5→33% ethyl acetate/hexane) to give the title compound (132 mg, 33%) as a pale-yellow oil.
$^1$H-NMR (CDCl$_3$): δ0.93 (t, J=7.54 Hz, 3H), 1.56-1.77 (M, 1H), 1.80-2.00 (M, 1H), 3.01 (dt, J=4.52, 2.26 Hz, 2H), 3.24 (td, J=12.72, 3.96 Hz, 1H), 3.51-3.69 (M, 2H), 3.72 (s, 2H), 3.87-4.02 (M, 6H), 4.23 (dd, J=4.90, 3.01 Hz, 2H), 7.21-7.36 (M, 5H), 7.67 (s, 1H)
ESI-MS: m/z 355 (M+H)$^+$.

Reference Example 15

3-chloro-5-[methyl(1-methylethyl)amino]pyrazine-2-carbaldehyde (Step 1)
A mixture of 2,6-dichloropyrazine (10 g), N-methylpropan-2-amine (10.5 mL), potassium carbonate (13.9 g) and DMA (40 mL) was stirred at 80° C. for 5 hr. Water (80 mL) was added, and the mixture was extracted with ethyl acetate. The aqueous layer was extracted again with ethyl acetate. The combined organic layer was washed with water and saturated brine, dried over magnesium sulfate, and concentrated. This was used without purification for the next reaction.
(Step 2)
Phosphoryl chloride (12.3 mL) was added dropwise to DMF (40 mL) at 0° C. The mixture was stirred for 15 min, and a solution of the residue obtained in step 1 in DMF (10 mL) was added dropwise thereto. The mixture was stirred at 80° C. for 5 hr, water (100 mL) was added at 0° C., and the mixture was stirred at room temperature for 1 hr and extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→30% ethyl acetate/hexane) to give the title compound (11.9 g, 2 steps 83%) as a pale-yellow powder.

$^1$H-NMR (CDCl$_3$): δ1.27 (d, J=6.59 Hz, 6H), 3.06 (s, 3H), 4.96 (brs, 1H), 8.05 (s, 1H), 10.15 (s, 1H)

ESI-MS: m/z 214 (M+H)$^+$.

Reference Example 16

2-[benzyl({3-chloro-5-[methyl(1-methylethyl)amino]pyrazin-2-yl}methyl)amino]ethanol Sodium triacetoxyborohydride (12.8 g) was added to a solution of 3-chloro-5-[methyl(1-methylethyl)amino]pyrazine-2-carbaldehyde (8.6 g), N-benzylethanolamine (7.3 g) and acetic acid (6.9 mL) in acetonitrile (86 mL), and the mixture was stirred at room temperature for 5 hr. To the reaction mixture were added ethyl acetate and 2M aqueous potassium carbonate solution (86 mL), and the aqueous layer was extracted with ethyl acetate. The combined organic layer was washed with water and saturated brine, dried over magnesium sulfate, and concentrated. The residue was purified by basic silica gel column chromatography (solvent gradient: 10→30% ethyl acetate/hexane) to give the title compound (15.1 g, quantitative) as a pale-yellow oil.

$^1$H-NMR (CDCl$_3$): δ1.19 (d, J=6.59 Hz, 6H), 2.69-2.79 (M, 2H), 2.88 (s, 3H), 3.52-3.64 (M, 2H), 3.66-3.74 (M, 1H), 3.75 (s, 2H), 3.81 (s, 2H), 4.59-4.78 (M, 1H), 7.14-7.38 (M, 5H), 7.85 (s, 1H)

ESI-MS: m/z 349 (M+H)$^+$.

Reference Example 17

8-benzyl-N-methyl-N-(1-methylethyl)-6,7,8,9-tetrahydropyrazino[2,3-f][1,4]oxazepin-3-amine To a solution of potassium tert-butoxide (5.8 g) in DMF (45 mL) was added dropwise a solution of 2-[benzyl({3-chloro-5-[methyl(1-methylethyl)amino]pyrazin-2-yl}methyl)amino]ethanol (15.1 g) in DMF (30 mL) at 0° C., and the mixture was stirred for 1.5 hr. Water (150 ml) was added, and the mixture was extracted with ethyl acetate. The aqueous layer was extracted again with ethyl acetate. The combined organic layer was washed with water and saturated brine, dried over magnesium sulfate, and concentrated. The residue was purified by basic silica gel column chromatography (eluent: 10% ethyl acetate/hexane) to give the title compound (11 g, 87%) as a pale-yellow oil.

$^1$H-NMR(CDCl$_3$): δ1.17 (d, J=6.59 Hz, 6H), 2.87 (s, 3H), 2.99-3.02 (m, 2H), 3.72 (s, 2H), 3.91(s, 2H), 4.18-4.30 (m, 2H), 4.70-4.80 (m, 1H), 7.15-7.42 (m, 5H), 7.63 (s, 1H)

ESI-MS: m/z 313(M+H)$^+$.

Reference Example 18

3-chloro-5-[(3R)-3-methylmorpholin-4-yl]pyrazine-2-carbaldehyde (Step 1)

A mixture of 2,6-dichloropyrazine (40 g), (3R)-3-methylmorpholine p-tosylate (91 g), potassium carbonate (112 g) and DMSO (300 mL) was stirred at 80° C. overnight. The reaction mixture was diluted with ethyl acetate, and the organic layer was washed with water and saturated brine, dried over magnesium sulfate, and concentrated. This was used without purification for the next reaction.

(Step 2)

Phosphoryl chloride (64 mL) was added dropwise to DMF (200 mL) at −10° C. to 0° C. The mixture was stirred for 10 min, and a solution of the residue obtained in step 1 in DMF (100 mL) was added dropwise thereto. The mixture was stirred at 60° C. overnight, water (300 mL) was added at 0° C., and the mixture was stirred at room temperature for 3 hr. The mixture was extracted with ethyl acetate. The combined organic layer was washed with water and saturated brine, dried over magnesium sulfate, and concentrated. The residue was purified by recrystallization (ethyl acetate/hexane) to give the title compound (26.7 g, 2 steps 41%) as a pale-yellow powder.

$^1$H-NMR (CDCl$_3$): δ1.41 (d, J=6.40 Hz, 3H), 3.31-3.52 (M, 1H), 3.61 (td, J=11.96, 2.83 Hz, 1H), 3.71-3.80 (M, 1H), 3.79-3.90 (m, 1H), 4.07 (dd, J=11.68, 3.77 Hz, 1H), 4.15 (d, J=12.06 Hz, 1H), 4.38-4.55 (M, 1H), 8.09 (s, 1H), 10.15 (s, 1H).

Reference Example 19

2-[benzyl({3-chloro-5-[(3R)-3-methylmorpholin-4-yl]pyrazin-2-yl}methyl)amino]ethanol Sodium triacetoxyborohydride (1.37 g) was added to a solution of 3-chloro-5-[(3R)-3-methylmorpholin-4-yl]pyrazine-2-carbaldehyde (1.04 g), N-benzylethanolamine (0.78 g) and acetic acid (0.74 mL) in acetonitrile (20 mL), and the mixture was stirred at room temperature overnight. The reaction mixture was basified with saturated aqueous sodium hydrogen carbonate, and extracted with ethyl acetate. The organic layer was washed with water and saturated brine, dried over magnesium sulfate, and concentrated. The residue was purified by basic silica gel column chromatography (solvent gradient: 5→40% ethyl acetate/hexane) to give the title compound (1.65 g, quantitative) as a colorless oil.

$^1$H-NMR (CDCl$_3$): δ1.27 (d, J=7.2 Hz, 3H), 2.69-2.81 (M, 2H), 3.26 (td, J=12.7, 3.8 Hz, 1H), 3.50-3.66 (M, 3H), 3.68-3.92 (M, 7H), 4.01 (dd, J=11.5, 4.0 Hz, 1H), 4.17-4.27 (M, 1H), 7.16-7.36 (M, 5H), 7.90 (s, 1H).

ESI-MS: m/z 377 (M+H)$^+$.

Reference Example 20

8-benzyl-3-[(3R)-3-methylmorpholin-4-yl]-6,7,8,9-tetrahydropyrazino[2,3-f][1,4]oxazepine Potassium tert-butoxide (0.59 g) was added to a solution of 2-[benzyl({3-chloro-5-[(3R)-3-methylmorpholin-4-yl]pyrazin-2-yl}methyl)amino]ethanol (1.65 g) in DMF (50 mL) at 0° C., and the mixture was stirred for 1 hr. Water was added, and the mixture was extracted with ethyl acetate. The organic layer was washed with water and saturated brine, dried over magnesium sulfate, and concentrated. The residue was purified by basic silica gel column chromatography (solvent gradient: 5→50% ethyl acetate/hexane) to give the title compound (1.32 g, 89%) as a pale-yellow solid.

$^1$H-NMR (CDCl$_3$): δ1.28 (d, J=6.8 Hz, 3H), 2.98-3.06 (M, 2H), 3.25 (td, J=12.5, 4.0 Hz, 1H), 3.60 (td, J=11.7, 3.0 Hz, 1H), 3.68-3.86 (M, 5H), 3.92 (s, 2H), 4.00 (dd, J=11.3, 3.4 Hz, 1H), 4.18-4.34 (M, 3H), 7.16-7.42 (M, 5H), 7.69 (s, 1H).

ESI-MS: m/z 341 (M+H)$^+$.

Reference Example 21

2-chloro-6-(2-methylpiperidin-1-yl)pyrazine

A mixture of 2,6-dichloropyrazine (1.49 g), 2-methylpiperidine (1.76 mL), potassium carbonate (2.07 g) and DMA (10 mL) was stirred at 80° C. for 22 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 5→20% ethyl acetate/hexane) to give the title compound (1.85 g, 87%) as a pale-yellow oil.

$^1$H-NMR (CDCl$_3$): δ1.20 (d, J=6.8 Hz, 3H), 1.45-1.58 (M, 1H), 1.61-1.87 (M, 5H), 2.98 (td, J=12.9, 3.0 Hz, 1H), 4.06-4.25 (M, 1H), 4.51-4.67 (M, 1H), 7.72 (s, 1H), 7.92 (s, 1H).

ESI-MS: m/z 213 (M+H)$^+$.

Reference Example 22

3-chloro-5-(2-methylpiperidin-1-yl)pyrazine-2-carbaldehyde

Phosphoryl chloride (1.62 mL) was added dropwise to DMF (5 mL) at 0° C. The mixture was stirred for 15 min, and a solution of 2-chloro-6-(2-methylpiperidin-1-yl)pyrazine (1.85 g) in DMF (1 mL) was added dropwise thereto. The mixture was stirred at 80° C. for 16 hr, water (5 mL) was added at 0° C., and the mixture was stirred at room temperature for 1.5 hr. The mixture was extracted with ethyl acetate. The aqueous layer was extracted again with ethyl acetate. The combined organic layer was washed with water and saturated brine, dried over magnesium sulfate, and concentrated. The residue was purified by recrystallization (ethyl acetate-hexane) to give the title compound (1.18 g, 57%) as a colorless powder.

$^1$H-NMR (CDCl$_3$): δ1.30 (d, J=6.8 Hz, 3H), 1.46-1.65 (M, 1H), 1.65-1.92 (M, 5H), 3.13 (td, J=13.3, 3.2 Hz, 1H), 4.40 (d, J=13.2 Hz, 1H), 4.80 (brs, 1H), 8.10 (s, 1H), 10.13 (s, 1H).

ESI-MS: m/z 240 (M+H)$^+$.

Reference Example 23

2-(benzyl{[3-chloro-5-(2-methylpiperidin-1-yl)pyrazin-2-yl]methyl}amino)ethanol

Sodium triacetoxyborohydride (1.56 g) was added to a solution of 3-chloro-5-(2-methylpiperidin-1-yl)pyrazine-2-carbaldehyde (1.18 g), N-benzylethanolamine (0.83 g) and acetic acid (0.84 mL) in acetonitrile (8 mL), and the mixture was stirred at room temperature for 21 hr. The reaction mixture was basified with saturated aqueous sodium hydrogen carbonate solution, and extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→50% ethyl acetate/hexane) to give the title compound (1.63 g, 89%) as a pale-yellow oil.

$^1$H-NMR (CDCl$_3$): δ1.19 (d, J=6.8 Hz, 3H), 1.43-1.83 (M, 7H), 2.71-2.77 (M, 2H), 2.96 (td, J=13.0, 3.0 Hz, 1H), 3.60 (t, J=4.9 Hz, 2H), 3.72 (brs, 1H), 3.75 (s, 2H), 3.80 (s, 2H), 4.49-4.59 (M, 1H), 7.17-7.35 (M, 5H), 7.91 (s, 1H).

ESI-MS: m/z 375 (M+H)$^+$.

Reference Example 24

8-benzyl-3-(2-methylpiperidin-1-yl)-6,7,8,9-tetrahydropyrazino[2,3-f][1,4]oxazepine To a solution of potassium tert-butoxide (0.65 g) in DMF (4 mL) was added dropwise a solution of 2-(benzyl{[3-chloro-5-(2-methylpiperidin-1-yl)pyrazin-2-yl]methyl}amino)ethanol (1.63 g) in DMF (4 mL) at 0° C., and the mixture was stirred for 2 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 5→33% ethyl acetate/hexane) to give the title compound (1.27 g, 78%) as a pale-yellow oil.

$^1$H-NMR (CDCl$_3$): δ1.17 (d, J=6.8 Hz, 3H), 1.43-1.84 (M, 6H), 2.88-3.03 (M, 3H), 3.72 (s, 2H), 3.90 (s, 2H), 4.04-4.14 (M, 1H), 4.18-4.24 (M, 2H), 4.53-4.65 (M, 1H), 7.21-7.36 (M, 5H), 7.71 (s, 1H).

ESI-MS: m/z 339 (M+H)$^+$.

Reference Example 25

3-chloro-5-(2-methylpyrrolidin-1-yl)pyrazine-2-carbaldehyde (Step 1)

A mixture of 2,6-dichloropyrazine (1.12 g), 2-methylpyrrolidine (1.14 mL), potassium carbonate (1.55 g) and DMA (7.5 mL) was stirred at 80° C. for 18 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. This was used without purification for the next reaction.

(Step 2)

Phosphoryl chloride (1.39 mL) was added dropwise to DMF (6 mL) at 0° C. The mixture was stirred for 15 min, and a solution of the residue obtained in step 1 in DMF (1 mL) was added dropwise thereto. The mixture was stirred at 50° C. for 20 hr, water (5 mL) was added at 0° C., and the mixture was stirred at room temperature for 1 hr and extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→33% ethyl acetate/hexane) to give the title compound (1.49 g, 2 steps 88%) as a pale-yellow powder.

$^1$H-NMR (CDCl$_3$): δ1.30 (d, J=6.40 Hz, 3H), 1.83 (brs, 1H), 2.12 (brs, 4H), 3.54 (brs, 1H), 3.72 (brs, 1H), 7.91 (brs, 1H), 10.15 (s, 1H).

ESI-MS: m/z 226 (M+H)$^+$.

Reference Example 26

2-(benzyl{[3-chloro-5-(2-methylpyrrolidin-1-yl)pyrazin-2-yl]methyl}amino)ethanol Sodium triacetoxyborohydride (2.09 g) was added to a solution of 3-chloro-5-(2-methylpyrrolidin-1-yl)pyrazine-2-carbaldehyde (1.49 g), N-benzylethanolamine (1.19 g) and acetic acid (1.13 mL) in acetonitrile (12 mL), and the mixture was stirred at room temperature for 16 hr. The reaction mixture was basified with saturated aqueous sodium hydrogen carbonate solution, and extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 20→50% ethyl acetate/hexane) to give the title compound (1.82 g, 76%) as a pale-yellow oil.

¹H-NMR (CDCl₃): δ1.22 (d, J=6.44 Hz, 3H), 1.74 (dt, J=5.02, 2.60 Hz, 1H), 1.95-2.17 (M, 3H), 2.71-2.77 (M, 2H), 3.31-3.44 (M, 1H), 3.51-3.63 (M, 3H), 3.63-3.73 (M, 1H), 3.75 (s, 2H), 3.81 (s, 2H), 4.10-4.20 (M, 1H), 7.17-7.35 (M, 5H), 7.72 (s, 1H).
ESI-MS: m/z 361 (M+H)⁺.

Reference Example 27

8-benzyl-3-(2-methylpyrrolidin-1-yl)-6,7,8,9-tetrahydropyrazino[2,3-f][1,4]oxazepine To a solution of potassium tert-butoxide (0.68 g) in DMF (5 mL) was added dropwise a solution of 2-(benzyl{[3-chloro-5-(2-methylpyrrolidin-1-yl)pyrazin-2-yl]methyl}amino) ethanol (1.82 g) in DMF (5 mL) at 0° C., and the mixture was stirred for 1.5 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→33% ethyl acetate/hexane) to give the title compound (1.38 g, 85%) as a pale-yellow oil.
¹H-NMR (CDCl₃): δ1.22 (d, J=6.40 Hz, 3H), 1.73 (dt, J=4.71, 2.54 Hz, 1H), 1.91-2.17 (M, 3H), 2.97-3.02 (M, 2H), 3.32-3.44 (M, 1H), 3.53-3.62 (M, 3H), 3.72 (s, 2H), 3.91 (s, 2H), 4.13-4.24 (m, 3H), 7.21-7.36 (M, 5H), 7.51 (s, 1H).
ESI-MS: m/z 325 (M+H)⁺.

Reference Example 28

6-chloro-N-methyl-N-(1-methylpropyl)pyrazin-2-amine

A mixture of 2,6-dichloropyrazine (1.49 g), N-methylbutan-2-amine (1.31 mL), potassium carbonate (2.07 g) and DMA (10 mL) was stirred at 80° C. for 40 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 5→20% ethyl acetate/hexane) to give the title compound (1.43 g, 72%) as a pale-yellow oil.
¹H-NMR (CDCl₃): δ0.85 (t, J=7.38 Hz, 3H), 1.17 (d, J=6.82 Hz, 3H), 1.49-1.66 (M, 2H), 2.87 (s, 3H), 4.44-4.58 (M, 1H), 7.73 (s, 1H), 7.86 (s, 1H).
ESI-MS: m/z 200(M)⁺.

Reference Example 29

3-chloro-5-[methyl(1-methylpropyl)amino]pyrazine-2-carbaldehyde

Phosphoryl chloride (1.33 mL) was added dropwise to DMF (5 mL) at 0° C. The mixture was stirred for 15 min, and a solution of 6-chloro-N-methyl-N-(1-methylpropyl) pyrazin-2-amine (1.43 g) in DMF (1 mL) was added dropwise thereto. The mixture was stirred at 80° C. for 18 hr, water (5 mL) was added at 0° C., and the mixture was stirred at room temperature for 1.5 hr. The mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10'50% ethyl acetate/hexane) to give the title compound (1.43 g, 88%) as a pale-yellow oil.
¹H-NMR (CDCl₃): δ0.88 (t, J=7.35 Hz, 3H), 1.15-1.32 (M, 3H), 1.59-1.70 (M, 2H), 3.02 (s, 3H), 7.26 (s, 1H), 8.06 (brs, 1H), 10.14 (s, 1H).
ESI-MS: m/z 228 (M+H)⁺.

Reference Example 30

2-[benzyl({3-chloro-5-[methyl(1-methylpropyl) amino]pyrazin-2-yl}methyl)amino]ethanol Sodium triacetoxyborohydride (2.0 g) was added to a solution of 3-chloro-5-[methyl(1-methylpropyl)amino]pyrazine-2-carbaldehyde (1.43 g), N-benzylethanolamine (1.14 g) and acetic acid (1.08 mL) in acetonitrile (10 mL), and the mixture was stirred at room temperature for 5 hr. The reaction mixture was basified with saturated aqueous sodium hydrogen carbonate solution, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 20→80% ethyl acetate/hexane) to give the title compound (2.07 g, 91%) as a pale-yellow oil.
¹H-NMR (CDCl₃): δ0.85 (t, J=7.38 Hz, 3H), 1.16 (d, J=6.82 Hz, 3H), 1.48-1.65 (M, 3H), 2.72-2.77 (M, 2H), 2.85 (s, 3H), 3.60 (t, J=4.92 Hz, 2H), 3.76 (s, 2H), 3.81 (s, 2H), 4.45 (sxt, J=6.97 Hz, 1H), 7.17-7.35 (M, 5H), 7.85 (s, 1H).
ESI-MS: m/z 363 (M+H)⁺.

Reference Example 31

8-benzyl-N-methyl-N-(1-methylpropyl)-6,7,8,9-tetrahydropyrazino[2,3-f][1,4]oxazepin-3-amine To a solution of potassium tert-butoxide (0.77 g) in DMF (5 mL) was added dropwise a solution of 2-[benzyl({3-chloro-5-[methyl(1-methylpropyl)amino]pyrazin-2-yl}methyl) amino]ethanol (2.07 g) in DMF (5 mL) at 0° C., and the mixture was stirred for 2.5 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 20→80% ethyl acetate/hexane) to give the title compound (1.44 g, 77%) as a pale-yellow oil.
¹H-NMR (CDCl₃): δ0.80-0.89 (M, 3H), 1.14 (d, J=6.44 Hz, 3H), 1.46-1.62 (M, 2H), 2.84 (s, 3H), 2.97-3.02 (M, 2H), 3.72 (s, 2H), 3.91 (s, 2H), 4.19-4.24 (M, 2H), 4.45-4.59 (M, 1H), 7.21-7.36 (M, 5H), 7.64 (s, 1H).
ESI-MS: m/z 327 (M+H)⁺.

Reference Example 32

6-chloro-N-(cyclopropylmethyl)pyrazin-2-amine

A mixture of 2,6-dichloropyrazine (2.99 g), 1-cyclopropylmethanamine (2.14 g), potassium carbonate (4.14 g) and DMA (20 mL) was stirred at 80° C. for 23 hr. Water (15 mL) was added, and the mixture was extracted with ethyl acetate. The aqueous layer was extracted again with ethyl acetate. The combined organic layer was washed with water and saturated brine, dried over magnesium sulfate, and concentrated. This was used without purification for the next reaction.
ESI-MS: m/z 184 (M+H)⁺.

Reference Example 33

6-chloro-N-(cyclopropylmethyl)-N-methylpyrazin-2-amine

To a solution of 6-chloro-N-(cyclopropylmethyl)pyrazin-2-amine (0.60 g) in tetrahydrofuran (5 mL) was added dropwise n-butyllithium (3.06 mL, 1.6 M hexane solution) at −78° C. The mixture was stirred at −78° C. for 5 min, and iodomethane (1.02 mL) was added dropwise thereto. The mixture was stirred at −78° C. for 30 min, and further stirred at 0° C. for 1 hr. Saturated aqueous sodium thiosulfate solution (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 5→15% ethyl acetate/hexane) to give the title compound (0.46 g, 70%) as a pale-yellow oil.

$^1$H-NMR (CDCl$_3$): δ0.25-0.32 (M, 2H), 0.51-0.59 (M, 2H), 0.93-1.11 (m, 1H), 3.14 (s, 3H), 3.43 (d, J=6.78 Hz, 2H), 7.75 (s, 1H), 7.88 (s, 1H).

ESI-MS: m/z 198 (M+H)$^+$.

Reference Example 34

3-chloro-5-[(cyclopropylmethyl)(methyl)amino]pyrazine-2-carbaldehyde

Phosphoryl chloride (0.43 mL) was added dropwise to DMF (1 mL) at 0° C. The mixture was stirred for 15 min, and a solution of 6-chloro-N-(cyclopropylmethyl)-N-methylpyrazin-2-amine (0.46 g) in DMF (1 mL) was added dropwise thereto. The mixture was stirred at 50° C. for 16 hr, water (5 mL) was added at 0° C., and the mixture was stirred at room temperature for 1.5 hr. The mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 5→20% ethyl acetate/hexane) to give the title compound (0.37 g, 71%) as a pale-yellow oil.

$^1$H-NMR (CDCl$_3$): δ0.34 (q, J=4.92 Hz, 2H), 0.55-0.68 (M, 2H), 1.01-1.16 (M, 1H), 1.57 (d, J=4.54 Hz, 1H), 3.29 (s, 3H), 3.55 (d, J=6.82 Hz, 1H), 8.07 (s, 1H), 10.15 (s, 1H).

ESI-MS: m/z 226 (M+H)$^+$.

Reference Example 35

2-[benzyl({3-chloro-5-[(cyclopropylmethyl)(methyl)amino]pyrazin-2-yl}methyl)amino]ethanol Sodium triacetoxyborohydride (0.51 g) was added to a solution of 3-chloro-5-[(cyclopropylmethyl)(methyl)amino]pyrazine-2-carbaldehyde (0.37 g), N-benzylethanolamine (0.29 g) and acetic acid (0.28 mL) in acetonitrile (5 mL), and the mixture was stirred at room temperature for 24 hr. The reaction mixture was basified with saturated aqueous sodium hydrogen carbonate solution, and extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 20-*40% ethyl acetate/hexane) to give the title compound (0.5 g, 86%) as a pale-yellow oil.

$^1$H-NMR (CDCl$_3$): δ0.27 (q, J=4.92 Hz, 2H), 0.49-0.59 (M, 2H), 0.96-1.12 (M, 1H), 2.71-2.79 (M, 2H), 3.12 (s, 3H), 3.40 (d, J=6.82 Hz, 2H), 3.59 (t, J=4.92 Hz, 2H), 3.65-3.73 (M, 1H), 3.75 (s, 2H), 3.81 (s, 2H), 7.17-7.37 (M, 5H), 7.88 (s, 1H).

ESI-MS: m/z 361 (M+H)$^+$.

Reference Example 36

8-benzyl-N-(cyclopropylmethyl)-N-methyl-6,7,8,9-tetrahydropyrazino[2,3-f][1,4]oxazepin-3-amine To a solution of 2-[benzyl({3-chloro-5-[(cyclopropylmethyl)(methyl)amino]pyrazin-2-yl}methyl)amino]ethanol (0.50 g) in DMF (3 mL) was added potassium tert-butoxide (0.19 g) at 0° C., and the mixture was stirred for 2.5 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→40% ethyl acetate/hexane) to give the title compound (0.36 g, 79%) as a pale-yellow oil.

$^1$H-NMR (CDCl$_3$): δ0.26 (q, J=4.90 Hz, 2H), 0.44-0.60 (M, 2H), 0.95-1.13 (M, 1H), 2.96-3.03 (M, 2H), 3.11 (s, 3H), 3.40 (s, 1H), 3.42 (s, 1H), 3.72 (s, 2H), 3.91 (s, 2H), 4.19-4.24 (M, 2H), 7.27-7.35 (M, 5H), 7.67 (s, 1H).

ESI-MS: m/z 325 (M+H)$^+$.

Reference Example 37

6-chloro-N-cyclobutylpyrazin-2-amine

A solution of 2,6-dichloropyrazine (4.47 g), cyclobutanamine (3.8 mL) and potassium carbonate (6.20 g) in DMA (30 mL) was stirred at 80° C. for 14 hr. Water was added to the reaction mixture, and the mixture was extracted with ethyl acetate. The extract was washed with water and saturated brine, dried over magnesium sulfate, and the solvent was evaporated under reduced pressure. The residue was purified by silica gel column chromatography (solvent gradient: 5→15% ethyl acetate/hexane) to give the title compound (4.42 g, 80%).

$^1$H-NMR (CDCl$_3$): δ1.70-1.99 (M, 4H), 2.39-2.53 (M, 2H), 4.16-4.31 (m, 1H), 4.91 (brs, 1H), 7.68 (s, 1H), 7.79 (s, 1H).

ESI-MS: m/z 184 (M+H)$^+$.

Reference Example 38

6-chloro-N-cyclobutyl-N-methylpyrazin-2-amine

To a solution of 6-chloro-N-cyclobutylpyrazin-2-amine (535 mg) in THF (30 mL) was added dropwise n-butyllithium (1.6 M hexane solution, 2.4 mL) under an argon stream at −78° C., and the mixture was stirred for 30 min. To the reaction mixture was added dropwise a solution of methyl iodide (542 μL) in THF (1 mL), and the mixture was stirred at room temperature for 1.5 hr. To the reaction mixture was added dropwise a saturated ammonium chloride solution, and the mixture was extracted with ethyl acetate. The extract was washed with saturated brine and dried over magnesium sulfate, and the solvent was evaporated under reduced pressure.

The residue was purified by silica gel column chromatography (solvent gradient: 5→33% ethyl acetate/hexane) to give the title compound (492 mg, 85%).

$^1$H-NMR (CDCl$_3$): δ1.67-1.82 (M, 2H), 2.10-2.35 (M, 4H), 3.04 (s, 3H), 4.58-4.73 (M, 1H), 7.76 (s, 1H), 7.84 (s, 1H).

ESI-MS: m/z 198 (M+H)$^+$.

Reference Example 39

3-chloro-5-[cyclobutyl(methyl)amino]pyrazine-2-carbaldehyde

Phosphoryl chloride (4.3 mL) was added dropwise to DMF (20 mL) at 0° C., and the mixture was stirred for 20 min. To the reaction mixture was added a solution of 6-chloro-N-cyclobutyl-N-methylpyrazin-2-amine (4.61 g) in DMF (5 mL), and the mixture was stirred at 50° C. for 15 hr. Water was added to the reaction mixture and the mixture was stirred for 2 hr and extracted with ethyl acetate. The extract was washed with water and saturated brine and dried over magnesium sulfate, and the solvent was evaporated under reduced pressure. The residue was purified by silica gel column chromatography (solvent gradient: 10→50% ethyl acetate/hexane) and recrystallized from hexane-diisopropyl ether to give the title compound (3.46 g, 66%).

$^1$H-NMR (CDCl$_3$): δ1.73-1.90 (M, 2H), 2.16-2.42 (M, 4H), 3.19 (s, 3H), 4.79 (brs, 1H), 8.03 (s, 1H), 10.15 (s, 1H).

ESI-MS: m/z 226 (M+H)$^+$.

Reference Example 40

2-[benzyl({3-chloro-5-[cyclobutyl(methyl)amino]pyrazin-2-yl}methyl)amino]ethanol Sodium triacetoxyborohydride (0.71 g) was added to a solution of 3-chloro-5-[cyclobutyl(methyl)amino]pyrazine-2-carbaldehyde (0.50 g), N-benzylethanolamine (0.40 g) and acetic acid (0.38 mL) in acetonitrile (8 mL), and the mixture was stirred at room temperature for 2 hr. The reaction mixture was basified with saturated aqueous sodium hydrogen carbonate solution, and extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→60% ethyl acetate/hexane) to give the title compound (0.74 g, 92%) as a pale-yellow oil.

$^1$H-NMR (CDCl$_3$): δ1.66-1.81 (M, 2H), 2.09-2.34 (M, 4H), 2.70-2.77 (m, 2H), 3.02 (s, 3H), 3.59 (t, J=5.09 Hz, 2H), 3.68 (brs, 1H), 3.74 (s, 2H), 3.81 (s, 2H), 4.55-4.71 (M, 1H), 7.17-7.35 (M, 5H), 7.83 (s, 1H).

ESI-MS: m/z 361 (M+H)$^+$.

Reference Example 41

8-benzyl-N-cyclobutyl-N-methyl-6,7,8,9-tetrahydropyrazino[2,3-f][1,4]oxazepin-3-amine To a solution of 2-[benzyl({3-chloro-5-[cyclobutyl(methyl)amino]pyrazin-2-yl}methyl)amino]ethanol (0.74 g) in DMF (4 mL) was added potassium tert-butoxide (0.28 g) at 0° C., and the mixture was stirred for 2 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→40% ethyl acetate/hexane) to give the title compound (0.48 g, 71%) as a pale-yellow oil.

ESI-MS: m/z 325 (M+H)$^+$.

Reference Example 42

N-benzyl-6-chloro-N-(1-methylethyl)pyrazin-2-amine

A mixture of 2,6-dichloropyrazine (7.45 g), N-benzylpropan-2-amine (12.5 mL), potassium carbonate (10.4 g) and DMA (50 mL) was stirred at 80° C. for 15 hr. Water (100 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 2→10% ethyl acetate/hexane) to give the title compound (1.55 g, 12%) as a pale-yellow oil.

$^1$H-NMR (CDCl$_3$): δ1.23 (d, J=6.78 Hz, 6H), 4.58 (s, 2H), 4.96 (quin, J=6.78 Hz, 1H), 7.18-7.36 (M, 5H), 7.64 (s, 1H), 7.75 (s, 1H).

ESI-MS: m/z 262 (M+H)$^+$.

Reference Example 43

5-[benzyl(1-methylethyl)amino]-3-chloropyrazine-2-carbaldehyde

Phosphoryl chloride (5.6 mL) was added dropwise to DMF (12 mL) at 0° C. The mixture was stirred for 15 min, and a solution of N-benzyl-6-chloro-N-(1-methylethyl)pyrazin-2-amine (3.40 g) in DMF (3 mL) was added dropwise thereto. The mixture was stirred at 100° C. for 13 hr, water (50 mL) was added at 0° C., and the mixture was stirred at room temperature for 1 hr. The mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 5-420% ethyl acetate/hexane) to give the title compound (2.42 g, 70%) as a pale-yellow oil.

$^1$H-NMR (CDCl$_3$): δ1.29 (d, J=6.78 Hz, 6H), 4.73 (s, 2H), 4.94-5.26 (M, 1H), 7.16-7.38 (M, 5H), 7.85 (brs, 1H), 10.12 (s, 1H).

ESI-MS: m/z 290 (M+H)$^+$.

Reference Example 44

2-[benzyl({5-[benzyl(1-methylethyl)amino]-3-chloropyrazin-2-yl}methyl)amino]ethanol Sodium triacetoxyborohydride (2.65 g) was added to a solution of 5-[benzyl(1-methylethyl)amino]-3-chloropyrazine-2-carbaldehyde (2.42 g), N-benzylethanolamine (1.42 g) and acetic acid (1.43 mL) in acetonitrile (14 mL), and the mixture was stirred at room temperature for 16 hr. The reaction mixture was basified with saturated aqueous sodium hydrogen carbonate solution, and extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 20→50% ethyl acetate/hexane) to give the title compound (3.32 g, 94%) as a pale-yellow oil.

¹H-NMR (CDCl₃): δ1.17-1.24 (M, 6H), 2.69-2.77 (M, 2H), 3.59 (t, J=5.27 Hz, 2H), 3.73 (s, 2H), 3.79 (s, 2H), 4.56 (s, 2H), 4.80-4.99 (M, 1H), 7.14-7.39 (M, 10H), 7.63 (s, 1H).
ESI-MS: m/z 425 (M+H)⁺.

Reference Example 45

N 8-dibenzyl-N-(1-methylethyl)-6,7,8,9-tetrahydropyrazino[2,3-f][1,4]oxazepin-3-amine To a solution of 2-[benzyl({5-[benzyl(1-methylethyl)amino]-3-chloropyrazin-2-yl}methyl)amino]ethanol (3.32 g) in DMF (12 mL) was added potassium tert-butoxide (1.05 g) at 0° C., and the mixture was stirred for 2 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→30% ethyl acetate/hexane) to give the title compound (2.55 g, 84%) as a pale-yellow oil.
¹H-NMR(CDCl₃): δ1.20 (d, J=6.78 Hz, 6H), 2.96-3.01 (m, 2H), 3.71 (s, 2H), 3.86 (s, 2H), 4.20-4.25 (m, 2H), 4.54 (s, 2H), 5.02 (dt, J=13.28, 6.73 Hz, 1H), 7.19-7.35 (m, 10H), 7.41 (s, 1H).
ESI-MS: m/z 389(M+H)⁺.

Reference Example 46

N-benzyl-N-(1-methylethyl)-6,7,8,9-tetrahydropyrazino[2,3-f][1,4]oxazepin-3-amine To a solution of N,8-benzyl-N-(1-methylethyl)-6,7,8,9-tetrahydropyrazino[2,3-f][1,4]oxazepin-3-amine (2.55 g) in methanol (20 mL) was added 20% Pd(OH)₂/C (260 mg), and the mixture was stirred under a hydrogen atmosphere at 50° C. for 2 hr. 20% Pd(OH)₂/C (500 mg) was further added, and the mixture was stirred under a hydrogen atmosphere at 50° C. for 4 hr. The reaction mixture was filtered, and the filtrate was concentrated to give the title compound (1.95 g, quantitative) as a colorless oil.
ESI-MS: m/z 299 (M+H)⁺

Reference Example 47 tert-butyl 3-[(1-methylethyl)amino]-6,7-dihydropyrazino[2,3-f][1,4]oxazepine-8(9H)-carboxylate Boc₂O (1.56 g) was added to a solution of N-benzyl-N-(1-methylethyl)-6,7,8,9-tetrahydropyrazino[2,3-f][1,4]oxazepin-3-amine (1.15 g) and triethylamine (1.10 mL) in ethyl acetate (15 mL), and the mixture was stirred at room temperature for 16 hr. The reaction mixture was neutralized with 1 N hydrochloric acid, and extracted with tetrahydrofuran. The organic layer was washed with water and saturated brine, dried over magnesium sulfate, and concentrated. The residue was purified by recrystallization (ethyl acetate-hexane) to give a colorless powder. To a solution of this in methanol (20 mL) was added 20% Pd(OH)₂/C (400 mg), and the mixture was stirred under a hydrogen atmosphere at 50° C. for 3 hr. 20% Pd(OH)₂/C (400 mg) was further added, and the mixture was stirred under a hydrogen atmosphere at 50° C. for 17 hr. The reaction mixture was filtered, and the filtrate was concentrated to give the title compound (1.24 g, 79%) as a pale-yellow oil.

¹H-NMR (CDCl₃): δ1.23 (d, J=6.40 Hz, 6H), 1.43 (s, 9H), 3.79-3.88 (M, 2H), 3.91-4.03 (M, 1H), 4.26-4.32 (M, 2H), 4.39 (d, J=7.91 Hz, 1H), 4.60 (brs, 2H), 7.49 (s, 1H).
ESI-MS: m/z 309 (M+H)⁺.

Reference Example 48 tert-butyl 3-[(D₃)methyl-(1-methylethyl)amino]-6,7-dihydropyrazino[2,3-f][1,4]oxazepine-8(9H)-carboxylate To a solution of tert-butyl 3-[(1-methylethyl)amino]-6,7-dihydropyrazino[2,3-f][1,4]oxazepine-8(9H)-carboxylate (150 mg) in tetrahydrofuran (3 mL) was added dropwise n-butyllithium (0.37 mL, 1.6 M hexane solution) at 0° C. The mixture was stirred at 0° C. for 15 min and methyl iodide-D₃ (90 μL) was added dropwise thereto. The mixture was stirred at 0° C. for 2 hr, and further at room temperature for 3 hr. Saturated aqueous sodium thiosulfate solution (5 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 20→25% ethyl acetate/hexane) to give the title compound (66 mg, 42%) as a pale-yellow oil.
¹H-NMR (CDCl₃): δ1.17 (d, J=6.78 Hz, 6H), 1.43 (s, 9H), 3.79-3.86 (M, 2H), 4.28-4.34 (M, 2H), 4.56-4.80 (M, 3H), 7.62 (s, 1H).
ESI-MS: m/z 326 (M+H)⁺.

Reference Example 49 tert-butyl 3-[ethyl(1-methylethyl)amino]-6,7-dihydropyrazino[2,3-f][1,4]oxazepine-8(9H)-carboxylate To a solution of tert-butyl 3-[(1-methylethyl)amino]-6,7-dihydropyrazino[2,3-f][1,4]oxazepine-8(9H)-carboxylate (137 mg) in tetrahydrofuran (3 mL) was added dropwise potassium hexamethyl disilazide (1.06 mL, 0.5 M toluene solution) at 0° C. The mixture was stirred at 0° C. for 15 min, and iodoethane (105 μL) was added dropwise thereto. The mixture was stirred at 0° C. for 1.5 hr, and further at room temperature overnight. Water (5 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→40% ethyl acetate/hexane) to give the title compound (10 mg, 7%) as a pale-yellow oil.
¹H-NMR (CDCl₃): δ1.12-1.28 (M, 9H), 1.43 (s, 9H), 3.37 (q, J=7.16 Hz, 2H), 3.83 (d, J=4.52 Hz, 2H), 4.26-4.36 (M, 2H), 4.61 (brs, 2H), 4.74 (dt, J=13.56, 6.78 Hz, 1H), 7.59 (s, 1H).
ESI-MS: m/z 337 (M+H)⁺.

Reference Example 50

3-chloro-5-[methyl(propyl)amino]pyrazine-2-carbaldehyde

A solution of 2,6-dichloropyrazine (4.47 g), N-methylpropan-1-amine (4.6 mL) and potassium carbonate (6.20 g) in DMA (30 mL) was stirred at 80° C. for 16 hr. Water was added to the reaction mixture, and the mixture was extracted with ethyl acetate. The extract was washed with saturated brine and dried over magnesium sulfate, and the solvent was evaporated under reduced pressure to give a crude product. Phosphoryl chloride (5.5 mL) was added dropwise to DMF (30 mL) at 0° C., and the mixture was stirred for 30 min. To this reaction mixture was added a solution of the obtained crude product in DMF (10 mL), and the mixture was stirred at 50° C. for 14 hr. Water was added to the reaction mixture and the mixture was stirred for 1 hr and extracted with ethyl acetate. The extract was washed with water and saturated brine and dried over magnesium sulfate, and the solvent was evaporated under reduced pressure. The residue was recrystallized from diisopropyl ether to give the title compound (4.76 g, 74%).

$^1$H-NMR (CDCl$_3$): δ0.98 (t, J=7.3 Hz, 3H), 1.63-1.79 (M, 2H), 3.23 (s, 3H), 3.51-3.69 (M, 2H), 8.04 (s, 1H), 10.14 (s, 1H).

ESI-MS: m/z 214 (M+H)$^+$.

Reference Example 51

2-[benzyl({3-chloro-5-[methyl(propyl)amino]pyrazin-2-yl}methyl)amino]ethanol

Sodium triacetoxyborohydride (0.74 g) was added to a solution of 3-chloro-5-[methyl(propyl)amino]pyrazine-2-carbaldehyde (0.50 g), N-benzylethanolamine (0.42 g) and acetic acid (0.40 mL) in acetonitrile (8 mL), and the mixture was stirred at room temperature for 6 hr. The reaction mixture was basified with saturated aqueous sodium hydrogen carbonate solution, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→40% ethyl acetate/hexane) to give the title compound (0.75 g, 91%) as a pale-yellow oil.

$^1$H-NMR (CDCl$_3$): δ0.94 (t, J=7.54 Hz, 3H), 1.63 (d, J=7.54 Hz, 2H), 2.71-2.77 (M, 2H), 3.07 (s, 3H), 3.40-3.49 (M, 2H), 3.56-3.64 (M, 2H), 3.75 (s, 2H), 3.81 (s, 2H), 7.15-7.36 (M, 5H), 7.83 (s, 1H).

ESI-MS: m/z 349 (M+H)$^+$.

Reference Example 52

8-benzyl-N-methyl-N-propyl-6,7,8,9-tetrahydropyrazino[2,3-f][1,4]oxazepin-3-amine To a solution of 2-[benzyl({3-chloro-5-[methyl(propyl)amino]pyrazin-2-yl}methyl)amino]ethanol (0.75 g) in DMF (4 mL) was added potassium tert-butoxide (0.29 g) at 0° C., and the mixture was stirred for 6 hr. Water (10 mL) was added, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 10→50% ethyl acetate/hexane) to give the title compound (50 mg, 8%) as a pale-yellow oil.

$^1$H-NMR (CDCl$_3$): δ0.93 (t, J=7.38 Hz, 3H), 1.61-1.70 (M, 2H), 2.97-3.03 (M, 2H), 3.03-3.09 (M, 3H), 3.41-3.50 (M, 2H), 3.72 (s, 2H), 3.90 (s, 2H), 4.19-4.25 (M, 2H), 7.20-7.38 (M, 5H), 7.62 (s, 1H).

ESI-MS: m/z 313 (M+H)$^+$.

Reference Example 53

8-benzyl-6,7,8,9-tetrahydropyrazino[2,3-f][1,4]oxazepin-3-amine

To a solution of 8-benzyl-3-chloro-6,7,8,9-tetrahydropyrazino[2,3-f][1,4]oxazepine (213 mg) in THF (5 mL) were added 2-(dicyclohexylphosphino)biphenyl (19 mg), Pd$_2$(dba)$_3$ (21 mg) and lithium hexamethyl disilazide (1 M THF solution, 1.16 mL) under an argon stream at room temperature. The reaction mixture was stirred at 60° C. to 70° C. for 1.5 hr. The reaction mixture was cooled to room temperature, 1 N hydrochloric acid (10 mL) was added, and the mixture was stirred at room temperature for 10 min. The aqueous layer was basified with saturated aqueous sodium hydrogen carbonate, and extracted with ethyl acetate. The combined organic layer was washed with water and saturated brine, dried over magnesium sulfate, and concentrated. The residue was purified by basic silica gel column chromatography (solvent gradient: 20→100% ethyl acetate/hexane) to give the title compound (97 mg, 49%) as a pale-yellow solid.

$^1$H-NMR (CDCl$_3$): δ2.93-3.08 (M, 2H), 3.72 (s, 2H), 3.92 (s, 2H), 4.15-4.29 (M, 2H), 4.43 (brs, 2H), 7.00-7.45 (M, 5H), 7.64 (s, 1H)

ESI-MS: m/z 257 (M+H)$^+$.

Reference Example 54

8-benzyl-3-(2,5-dimethyl-1H-pyrrol-1-yl)-6,7,8,9-tetrahydropyrazino[2,3-f][1,4]oxazepine A mixture of 8-benzyl-6,7,8,9-tetrahydropyrazino[2,3-f][1,4]oxazepin-3-amine (100 mg), 2,5-hexanedione (50 μL), acetic acid (164 μL) and toluene (3 mL) was stirred at 80° C. for 24 hr. The mixture was diluted with ethyl acetate at room temperature, and the organic layer was washed with water and saturated brine, dried over magnesium sulfate, and concentrated. The residue was purified by silica gel column chromatography (solvent gradient: 10→100% ethyl acetate/hexane) to give the title compound (60 mg, 46%) as a pale-yellow oil.

$^1$H-NMR (CDCl$_3$): δ2.17 (s, 6H), 3.05-3.13 (M, 2H), 3.80 (s, 2H), 4.08 (s, 2H), 4.29-4.36 (M, 2H), 5.91 (s, 2H), 7.28-7.38 (M, 5H), 8.19 (s, 1H).

ESI-MS: m/z 335 (M+H)$^+$.

Reference Example 55

8-benzyl-3-(2-methyl-1H-imidazol-1-yl)-6,7,8,9-tetrahydropyrazino[2,3-f][1,4]oxazepine A solution of 8-benzyl-3-chloro-6,7,8,9-tetrahydropyrazino[2,3-f][1,4]oxazepine (100 mg), 2-methyl-1H-imidazole (42 mg), copper iodide (14 mg) and cesium carbonate (236 mg) in DMF (2 mL) was stirred at 100° C. overnight. The reaction mixture was filtered, water (10 mL) was added to the filtrate, and the mixture was extracted with ethyl acetate. The aqueous layer was extracted again with ethyl acetate. The combined organic layer was washed with water and saturated brine, dried over magnesium sulfate, and concentrated. The residue was purified by silica gel column chromatography (solvent gradient: 50→100% ethyl acetate/hexane) to give the title compound (18 mg, 15%) as a pale-yellow oil.

$^1$H-NMR(CDCl$_3$): δ2.63 (s, 3H), 3.07-3.16 (M, 2H), 3.79 (s, 2H), 4.07 (s, 2H), 4.30-4.43 (M, 2H), 7.04 (s, 1H), 7.28-7.40 (M, 6H), 8.32 (s, 1H).

ESI-MS: m/z 322 (M+H)$^+$.

Reference Example 56

8-benzyl-2-chloro-N-methyl-N-(1-methylethyl)-6,7,8,9-tetrahydropyrazino[2,3-f][1,4]oxazepin-3-amine A mixture of 8-benzyl-N-methyl-N-(1-methylethyl)-6,7,8,9-tetrahydropyrazino[2,3-f][1,4]oxazepin-3-amine (500 mg), N-chlorosuccinimide (257 mg) and acetonitrile (10 mL) was stirred at room temperature for 16 hr and at 50° C. for 24 hr. Water was added, and the mixture was extracted with ethyl acetate. The organic layer was washed with water and saturated brine, dried over sodium sulfate, and concentrated under reduced pressure. The obtained residue was purified by silica gel column chromatography (solvent gradient: 0→40% ethyl acetate/hexane) to give the title compound (437 mg, 79%) as a yellow oil.

$^1$H-NMR (CDCl$_3$): δ1.20 (d, J=6.78 Hz, 6H), 2.85 (s, 3H), 2.93-3.05 (M, 2H), 3.73 (s, 2H), 3.90 (s, 2H), 4.18-4.27 (M, 2H), 4.38 (quip, J=6.59 Hz, 1H), 7.27-7.36 (M, 5H).
ESI-MS: m/z 347 (M+H)$^+$.

Reference Example 57

8-benzyl-2-bromo-N-methyl-N-(1-methylethyl)-6,7,8,9-tetrahydropyrazino[2,3-f][1,4]oxazepin-3-amine A mixture of 8-benzyl-N-methyl-N-(1-methylethyl)-6,7,8,9-tetrahydropyrazino[2,3-f][1,4]oxazepin-3-amine (500 mg), N-bromosuccinimide (342 mg) and acetonitrile (10 mL) was stirred at room temperature for 16 hr and at 50° C. for 24 hr. Water was added, and the mixture was extracted with ethyl acetate. The organic layer was washed with water and saturated brine, dried over sodium sulfate, and concentrated under reduced pressure. The obtained residue was purified by silica gel column chromatography (solvent gradient: 0→40% ethyl acetate/hexane) to give the title compound (122 mg, 20%) as a colorless oil.

$^1$H-NMR (CDCl$_3$): δ1.13-1.24 (M, 6H), 2.83 (s, 3H), 2.93-3.06 (M, 2H), 3.74 (s, 2H), 3.91 (s, 2H), 4.19-4.28 (M, 2H), 4.28-4.44 (m, 1H), 7.26-7.38 (M, 5H).
ESI-MS: m/z 391 (M+H)$^+$.

Reference Example 58 tert-butyl 3-[methyl(1-methylethyl)amino]-6,7-dihydropyrazino[2,3-f][1,4]oxazepine-8(9H)-carboxylate A mixture of 8-benzyl-N-methyl-N-(1-methylethyl)-6,7,8,9-tetrahydropyrazino[2,3-f][1,4]oxazepin-3-amine (2.0 g), 20% Pd(OH)$_2$/C (200 mg) and methanol (20 mL) was stirred under a hydrogen atmosphere at 50° C. for 2 hr. Insoluble material was filtered off, and the filtrate was concentrated under reduced pressure. Boc$_2$O (2.1 g), 1N aqueous sodium hydroxide solution (10 mL) and THF (20 mL) were added, and the mixture was stirred at room temperature for 16 hr. Ethyl acetate was added, and the organic layer was separated. The organic layer was washed with water and saturated brine, dried over sodium sulfate, and concentrated under reduced pressure. The obtained residue was purified by silica gel column chromatography (solvent gradient: 3→40% ethyl acetate/hexane) to give the title compound (2.2 g, quantitative) as a colorless oil.

$^1$H-NMR (CDCl$_3$): δ1.17 (d, J=6.78 Hz, 6H), 1.43 (s, 9H), 2.87 (s, 3H), 3.79-3.92 (M, 2H), 4.26-4.38 (M, 2H), 4.57-4.81 (M, 3H), 7.62 (s, 1H).
ESI-MS: m/z 323 (M+H)$^+$.

Reference Example 59 tert-butyl 2-bromo-3-[methyl(1-methylethyl)amino]-6,7-dihydropyrazino[2,3-f][1,4]oxazepine-8(9H)-carboxylate A mixture of tert-butyl 3-[methyl(1-methylethyl)amino]-6,7-dihydropyrazino[2,3-f][1,4]oxazepine-8(9H)-carboxylate (1.0 g), N-bromosuccinimide (608 mg) and acetonitrile (20 mL) was stirred at room temperature for 16 hr. Water was added, and the mixture was extracted with ethyl acetate. The organic layer was washed with water and saturated brine, dried over sodium sulfate, and concentrated under reduced pressure. The obtained residue was purified by silica gel column chromatography (solvent gradient: 3→30% ethyl acetate/hexane) to give the title compound (915 mg, 74%) as a colorless oil.

$^1$H-NMR (CDCl$_3$): δ1.20 (d, J=6.78 Hz, 6H), 1.43 (s, 9H), 2.82 (s, 3H), 3.77-3.92 (M, 2H), 4.25-4.41 (M, 3H), 4.60 (brs, 2H).
ESI-MS: 401 (M+H)$^+$.

Reference Example 60 tert-butyl 2-methyl-3-[methyl(1-methylethyl)amino]-6,7-dihydropyrazino[2,3-f][1,4]oxazepine-8(9H)-carboxylate A mixture of tert-butyl 2-bromo-3-[methyl(1-methylethyl)amino]-6,7-dihydropyrazino[2,3-f][1,4]oxazepine-8(9H)-carboxylate (200 mg), methylboronic acid (119 mg), tetrakis(triphenylphosphine)palladium(0) (58 mg), tripotassium phosphate (423 mg) and DME (3 mL) was stirred under an argon atmosphere at 90° C. for 16 hr. Water was added, and the mixture was extracted with ethyl acetate. The organic layer was washed with water and saturated brine, dried over sodium sulfate, and concentrated under reduced pressure. The obtained residue was purified by silica gel column chromatography (solvent gradient: 3→40% ethyl acetate/hexane) to give the title compound (109 mg, 65%) as a pale-yellow oil.

$^1$H-NMR (CDCl$_3$): δ1.16 (d, J=6.82 Hz, 6H), 1.42 (s, 9H), 2.43 (s, 3H), 2.73 (s, 3H), 3.79-3.95 (M, 3H), 4.25-4.38 (M, 2H), 4.63 (brs, 2H).
ESI-MS: m/z 337 (M+H)$^+$.

Reference Example 61

8-benzyl-3-[(1-methylethyl)sulfanyl]-6,7,8,9-tetrahydropyrazino[2,3-f][1,4]oxazepine A suspension of 8-benzyl-3-chloro-6,7,8,9-tetrahydropyrazino[2,3-f][1,4]oxazepine (300 mg), isopropylthiol (0.121 mL) and potassium carbonate (451 mg) in DMF (5 mL) was stirred with heating at 100° C. for 16 hr. Water was added to the reaction mixture, and the mixture was extracted with ethyl acetate. The organic layer was washed with saturated brine, dried over sodium sulfate, and concentrated under reduced pressure. The obtained residue was purified by basic silica gel column chromatography (solvent gradient: 36→40% ethyl acetate/hexane), and further by preparative HPLC to give the title compound (111 mg, 32%) as a yellow oil.

$^1$H-NMR (CDCl$_3$): δ1.40 (d, J=6.8 Hz, 6H), 2.98-3.12 (M, 2H), 3.7 (s, 2H), 3.93-4.03 (M, 1H), 3.97 (s, 2H), 4.21-4.32 (M, 2H), 7.28-7.43 (M, 5H), 8.07 (s, 1H).

ESI-MS: m/z 316 (M+H)⁺.

Reference Example 62

(2R)-1-[benzyl({3-chloro-5-[methyl(1-methylethyl)amino]pyrazin-2-yl}methyl)amino]-3-methoxypropan-2-ol To a solution of 3-chloro-5-[methyl(1-methylethyl)amino]pyrazine-2-carbaldehyde (321 mg), (2R)-1-(benzylamino)-3-methoxypropan-2-ol (351 mg) and acetic acid (258 μL) in acetonitrile (5 mL) was added sodium triacetoxyborohydride (477 mg), and the mixture was stirred at room temperature for 5.5 hr. To the reaction mixture was added dropwise saturated sodium hydrogen carbonate solution, and the mixture was extracted with ethyl acetate. The organic layer was washed with saturated brine and dried over magnesium sulfate, and the solvent was evaporated under reduced pressure. The residue was purified by silica gel column chromatography (solvent gradient: 10→50% ethyl acetate/hexane) to give the title compound (370 mg, 70%).

¹H-NMR (CDCl₃): δ1.19 (d, J=6.4 Hz, 6H), 2.54-2.72 (M, 2H), 2.88 (s, 3H), 3.28-3.40 (M, 5H), 3.60-3.98 (M, 5H), 4.33 (brs, 1H), 4.61-4.76 (M, 1H), 7.15-7.36 (M, 5H), 7.84 (s, 1H).
ESI-MS: m/z 393 (M+H)⁺.

Reference Example 63

(6R)-8-benzyl-6-(methoxymethyl)-N-methyl-N-(1-methylethyl)-6,7,8,9-tetrahydropyrazino[2,3-f][1,4]oxazepin-3-amine To a solution of (2R)-1-[benzyl({3-chloro-5-[methyl(1-methylethyl)amino]pyrazin-2-yl}methyl)amino]-3-methoxypropan-2-ol (363 mg) in DMF (5 mL) was added potassium tert-butoxide (124 mg) at 0° C., and the mixture was stirred at room temperature for 2.5 hr. Water was added to the reaction mixture, and the mixture was extracted with ethyl acetate. The extract was washed with water and saturated brine and dried over magnesium sulfate, and the solvent was evaporated under reduced pressure. The residue was purified by silica gel column chromatography (solvent gradient: 10→50% ethyl acetate/hexane) to give the title compound (270 mg, 82%).

ESI-MS: m/z 357 (M+H)⁺.
¹H-NMR (CDCl₃): δ1.17 (dd, J=7.9, 6.8 Hz, 6H), 2.87 (3H, s), 2.88-3.10 (2H, m), 3.38 (3H, s), 3.46-3.55 (1H, m), 3.61-3.87 (4H, m), 3.91-4.01 (1H, m), 4.27-4.37 (1H, m, J=9.3, 5.4, 5.4, 2.1 Hz), 4.69-4.84 (1H, m), 7.21-7.36 (5H, m), 7.61 (1H, s).

Reference Example 64

(2R)-1-[benzyl({3-chloro-5-[methyl(1-methylpropyl)amino]pyrazin-2-yl}methyl)amino]-3-methoxypropan-2-ol To a solution of 3-chloro-5-[methyl(1-methylpropyl)amino]pyrazine-2-carbaldehyde (342 mg), (2R)-1-(benzylamino)-3-methoxypropan-2-ol (351 mg) and acetic acid (258 μL) in acetonitrile (5 mL) was added sodium triacetoxyborohydride (477 mg), and the mixture was stirred at room temperature for 3 hr. To the reaction mixture was added dropwise saturated sodium hydrogen carbonate solution, and the mixture was extracted with ethyl acetate. The organic layer was washed with saturated brine and dried over magnesium sulfate, and the solvent was evaporated under reduced pressure. The residue was purified by silica gel column chromatography (solvent gradient: 10→50% ethyl acetate/hexane) to give the title compound (389 mg, 64%).

¹H-NMR (CDCl₃): δ0.85 (t, J=7.3 Hz, 3H), 1.15 (d, J=6.8 Hz, 3H), 1.48-1.69 (M, 3H), 2.54-2.72 (M, 2H), 2.85 (s, 3H), 3.29-3.40 (m, 5H), 3.61-3.79 (M, 2H), 3.83-3.97 (M, 3H), 4.35-4.52 (M, 1H), 7.16-7.36 (M, 5H), 7.85 (s, 1H).
ESI-MS: m/z 407 (M+H)⁺.

Reference Example 65

(6R)-8-benzyl-6-(methoxymethyl)-N-methyl-N-(1-methylpropyl)-6,7,8,9-tetrahydropyrazino[2,3-f][1,4]oxazepin-3-amine To a solution of (2R)-1-[benzyl({3-chloro-5-[methyl(1-methylpropyl)amino]pyrazin-2-yl}methyl)amino]-3-methoxypropan-2-ol (385 mg) in DMF (10 mL) was added potassium tert-butoxide (126 mg), and the mixture was stirred at room temperature for 1.5 hr. Water was added to the reaction mixture, and the mixture was extracted with ethyl acetate. The extract was washed with water and saturated brine and dried over magnesium sulfate, and the solvent was evaporated under reduced pressure. The residue was purified by silica gel column chromatography (solvent gradient: 20→50% ethyl acetate/hexane) to give the title compound (300 mg, 86%).

¹H-NMR (CDCl₃): δ0.78-0.91 (M, 3H), 1.08-1.19 (M, 3H), 1.47-1.59 (m, 2H), 2.84 (s, 3H), 2.87-2.98 (M, 1H), 3.00-3.09 (M, 1H), 3.38 (s, 3H), 3.46-3.55 (M, 1H), 3.61-3.87 (M, 4H), 3.90-4.00 (m, 1H), 4.26-4.38 (M, 1H), 4.44-4.59 (M, 1H), 7.20-7.36 (M, 5H), 7.62 (s, 1H).
ESI-MS: m/z 371 (M+H)⁺.

Reference Example 66

(2R)-1-[benzyl({3-chloro-5-[methyl(propyl)amino]pyrazin-2-yl}methyl)amino]-3-methoxypropan-2-ol To a solution of 3-chloro-5-[methyl(propyl)amino]pyrazine-2-carbaldehyde (427 mg), (2R)-1-(benzylamino)-3-methoxypropan-2-ol (469 mg) and acetic acid (343 μL) in acetonitrile (10 mL) was added sodium triacetoxyborohydride (636 mg), and the mixture was stirred at room temperature for 1.5 hr. To the reaction mixture was added dropwise a saturated sodium hydrogen carbonate solution, and the mixture was extracted with ethyl acetate. The organic layer was washed with saturated brine and dried over magnesium sulfate, and the solvent was evaporated under reduced pressure. The residue was purified by silica gel column chromatography to (solvent gradient: 5→50% ethyl acetate/hexane) to give the title compound (579 mg, 74%).

¹H-NMR (CDCl₃): δ0.93 (t, J=7.3 Hz, 3H), 1.53-1.71 (M, 3H), 2.54-2.72 (M, 2H), 3.06 (s, 3H), 3.28-3.38 (M, 5H), 3.39-3.48 (m, 2H), 3.60-3.79 (M, 2H), 3.82-3.96 (M, 3H), 7.17-7.35 (M, 5H), 7.83 (s, 1H).
ESI-MS: m/z 393 (M+H)⁺.

Reference Example 67

(6R)-8-benzyl-6-(methoxymethyl)-N-methyl-N-propyl-6,7,8,9-tetrahydropyrazino[2,3-f][1,4]oxazepin-3-amine To a solution of (2R)-1-[benzyl({3-chloro-5-[methyl(propyl)amino]pyrazin-2-yl}methyl)amino]-3-methoxypropan-2-ol (574 mg) in DMF (15 mL) was added potassium tert-butoxide (197 mg), and the mixture was stirred at room temperature for 1.5 hr. Water was added to the reaction mixture, and the mixture was extracted with ethyl acetate. The extract was washed with water and saturated brine and dried over magnesium sulfate, and the solvent was evaporated under reduced pressure. The residue was purified by silica gel column chromatography (solvent gradient: 10→33% ethyl acetate/hexane) to give the title compound (468 mg, 90%).

$^1$H-NMR (CDCl$_3$): δ0.92 (t, J=7.3 Hz, 3H), 1.55-1.70 (M, 2H), 2.87-2.97 (M, 1H), 3.00-3.09 (M, 4H), 3.38 (s, 3H), 3.40-3.55 (m, 3H), 3.61-3.87 (M, 4H), 3.91-4.00 (M, 1H), 4.26-4.36 (M, 1H), 7.21-7.36 (M, 5H), 7.60 (s, 1H).

ESI-MS: m/z 357 (M+H)$^+$.

Reference Example 68

2-chloro-6-[2-(methoxymethyl)pyrrolidin-1-yl]pyrazine

A solution of 2,6-dichloropyrazine (1.18 g), 2-(methoxymethyl)pyrrolidine (1.0 g) and potassium carbonate (1.64 g) in DMA (15 mL) was stirred at 80° C. for 16 hr. Water was added to the reaction mixture, and the mixture was extracted with ethyl acetate. The extract was washed with water and saturated brine and dried over magnesium sulfate, and the solvent was evaporated under reduced pressure. The residue was purified by silica gel column chromatography (solvent gradient: 5→15% ethyl acetate/hexane) to give the title compound (1.45 g, 80%).

$^1$H-NMR (CDCl$_3$): δ1.93-2.19 (M, 4H), 3.33-3.45 (M, 5H), 3.48-3.61 (m, 2H), 4.19-4.29 (M, 1H), 7.76 (s, 1H), 7.81 (s, 1H).

ESI-MS: m/z 228 (M+H)$^+$.

Reference Example 69

3-chloro-5-[2-(methoxymethyl)pyrrolidin-1-yl]pyrazine-2-carbaldehyde

Phosphoryl chloride (1.2 mL) was added dropwise to DMF (10 mL) at 0° C., and the mixture was stirred for 20 min. To the reaction mixture was added a solution of 2-chloro-6-[2-(methoxymethyl)pyrrolidin-1-yl]pyrazine (1.45 g) in DMF (3 mL), and the mixture was stirred at 50° C. for 16 hr. Water was added to the reaction mixture, and the mixture was stirred for 2 hr, and extracted with ethyl acetate. The extract was washed with water and saturated brine and dried over magnesium sulfate, and the solvent was evaporated under reduced pressure. The residue was purified by silica gel column chromatography (solvent gradient: 5→50% ethyl acetate/hexane) to give the title compound (1.04 g, 64%).

$^1$H-NMR (CDCl$_3$): δ1.94-2.33 (M, 4H), 3.35 (s, 3H), 3.38-3.82 (M, 4H), 4.23-4.60 (M, 1H), 8.02 (brs, 1H), 10.15 (s, 1H).

ESI-MS: m/z 256 (M+H)$^+$.

Reference Example 70

(2R)-1-[benzyl({3-chloro-5-[2-(methoxymethyl)pyrrolidin-1-yl]pyrazin-2-yl}methyl)amino]-3-methoxypropan-2-ol To a solution of 3-chloro-5-[2-(methoxymethyl)pyrrolidin-1-yl]pyrazine-2-carbaldehyde (511 mg), (2R)-1-(benzylamino)-3-methoxypropan-2-ol (469 mg) and acetic acid (343 µL) in acetonitrile (10 mL) was added sodium triacetoxyborohydride (636 mg), and the mixture was stirred at room temperature for 14.5 hr. To the reaction mixture was added dropwise a saturated sodium hydrogen carbonate solution, and the mixture was extracted with ethyl acetate. The organic layer was washed with saturated brine and dried over magnesium sulfate, and the solvent was evaporated under reduced pressure. The residue was purified by silica gel column chromatography (solvent gradient: 10→50% ethyl acetate/hexane) to give the title compound (583 mg, 67%).

$^1$H-NMR (CDCl$_3$): δ1.91-2.17 (M, 4H), 2.54-2.72 (M, 2H), 3.27-3.43 (m, 10H), 3.46-3.79 (M, 4H), 3.82-3.96 (M, 3H), 4.13-4.34 (M, 2H), 7.16-7.36 (M, 5H), 7.80 (s, 1H).

ESI-MS: m/z 435 (M+H)$^+$.

Reference Example 71

(6R)-8-benzyl-6-(methoxymethyl)-3-[2-(methoxymethyl)pyrrolidin-1-yl]-6,7,8,9-tetrahydropyrazino[2,3-f][1,4]oxazepine To a solution of (2R)-1-[benzyl({3-chloro-5-[2-(methoxymethyl)pyrrolidin-1-yl]pyrazin-2-yl}methyl)amino]-3-methoxypropan-2-ol (578 mg) in DMF (10 mL) was added potassium tert-butoxide (179 mg), and the mixture was stirred at room temperature for 2 hr. Water was added to the reaction mixture, and the mixture was extracted with ethyl acetate. The extract was washed with water and saturated brine and dried over magnesium sulfate, and the solvent was evaporated under reduced pressure. The residue was purified by silica gel column chromatography (solvent gradient: 10→50% ethyl acetate/hexane) to give the title compound (467 mg, 88%).

$^1$H-NMR (CDCl$_3$): δ1.93-2.14 (M, 4H), 2.88-3.10 (M, 2H), 3.28-3.43 (m, BH), 3.47-4.01 (M, 8H), 4.16-4.35 (M, 2H), 7.21-7.35 (M, 5H), 7.58 (s, 1H).

ESI-MS: m/z 399 (M+H)$^+$.

Reference Example 72

(2R)-1-[benzyl({3-chloro-5-[cyclobutyl(methyl)amino]pyrazin-2-yl}methyl)amino]-3-methoxypropan-2-ol To a solution of 3-chloro-5-[cyclobutyl(methyl)amino]pyrazine-2-carbaldehyde (451 mg), (2R)-1-(benzylamino)-3-methoxypropan-2-ol (469 mg) and acetic acid (343 µL) in acetonitrile (10 mL) was added sodium triacetoxyborohydride (636 mg), and the mixture was stirred at room temperature for 1 hr. To the reaction mixture was added dropwise a saturated sodium hydrogen carbonate solution, and the mixture was extracted with ethyl acetate. The organic layer was washed with saturated brine and dried over magnesium sulfate, and the solvent was evaporated under reduced pressure. The residue was purified by silica gel column chromatography (solvent gradient: 10→50% ethyl acetate/hexane) to give the title compound (674 mg, 83%).

$^1$H-NMR (CDCl$_3$): δ1.65-1.81 (M, 2H), 2.09-2.33 (M, 4H), 2.53-2.72 (m, 2H), 3.02 (s, 3H), 3.27-3.39 (M, 5H), 3.59-3.79 (M, 2H), 3.81-3.96 (M, 3H), 4.30 (brs, 1H), 4.54-4.69 (M, 1H), 7.16-7.34 (M, 5H), 7.83 (s, 1H).

ESI-MS: m/z 405 (M+H)$^+$.

Reference Example 73

(6R)-8-benzyl-N-cyclobutyl-6-(methoxymethyl)-N-methyl-6,7,8,9-tetrahydropyrazino[2,3-f][1,4]oxazepin-3-amine To a solution of (2R)-1-[benzyl({3-chloro-5-[cyclobutyl(methyl)amino]pyrazin-2-yl}methyl)amino]-3-methoxypropan-2-ol (670 mg) in DMF (10 mL) was added potassium tert-butoxide (223 mg), and the mixture was stirred at room temperature for 2 hr. Water was added to the reaction mixture, and the mixture was extracted with ethyl acetate. The extract was washed with water and saturated brine and dried over magnesium sulfate, and the solvent was evaporated under reduced pressure. The residue was purified by silica gel column chromatography (solvent gradient: 10→50% ethyl acetate/hexane) to give the title compound (530 mg, 87%).

¹H-NMR (CDCl₃): δ1.61-1.79 (M, 2H), 2.08-2.32 (M, 4H), 2.88-3.10 (m, 5H), 3.39 (s, 3H), 3.50 (dd, J=10.2, 5.3 Hz, 1H), 3.60-3.88 (M, 4H), 3.91-4.02 (M, 1H), 4.27-4.37 (M, 1H), 4.65-4.80 (m, 1H), 7.21-7.35 (M, 5H), 7.60 (s, 1H).

ESI-MS: m/z 369 (M+H)⁺.

Example 1

3-cyclopentyl-6,7,8,9-tetrahydropyrazino[2,3-f][1,4]oxazepine hydrochloride

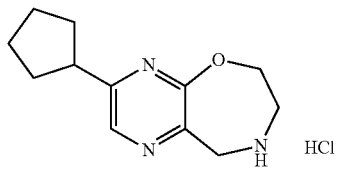

A mixture of 8-benzyl-3-(cyclopent-1-en-1-yl)-6,7,8,9-tetrahydropyrazino[2,3-f][1,4]oxazepine (290 mg), 10% Pd/C (150 mg) and methanol (3 mL) was stirred under a hydrogen atmosphere at 50° C. for 4 hr. Insoluble material was filtered off, and the filtrate was concentrated under reduced pressure. The residue was purified by basic silica gel column chromatography (solvent gradient; 10→100% ethyl acetate/hexane). To a solution of the obtained oil in methanol (2 mL) was added 1 N hydrochloric acid (0.75 mL), and the mixture was concentrated under reduced pressure. The obtained crude crystals were purified by recrystallization (ethanol-diisopropyl ether) to give the title compound (165 mg, 68%) as colorless crystals.

¹H-NMR (DMSO-d₆): δ1.44-1.86 (M, 6H), 1.87-2.13 (M, 2H), 3.07-3.28 (M, 1H), 3.46-3.64 (M, 2H), 4.36-4.63 (M, 4H), 8.33 (s, 1H), 9.87 (brs, 2H)

ESI-MS (free base): m/z 220 (M+H)⁺.

Example 2

3-(1-methylethoxy)-6,7,8,9-tetrahydropyrazino[2,3-f][1,4]oxazepine hydrochloride

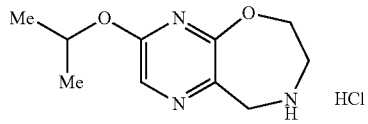

A mixture of 8-benzyl-3-(1-methylethoxy)-6,7,8,9-tetrahydropyrazino[2,3-f][1,4]oxazepine (137 mg), 20% Pd(OH)₂/C (100 mg) and methanol (2 mL) was stirred under a hydrogen atmosphere at 50° C. for 1 hr. Insoluble material was filtered off, and the filtrate was concentrated under reduced pressure.

To a solution of the obtained oil in methanol (1 mL) was added 1 N hydrochloric acid (0.42 mL) and the mixture was concentrated under reduced pressure. The obtained crude crystals were purified by recrystallization (ethanol-diisopropyl ether) to give the title compound (83.7 mg, 74%) as colorless crystals.

¹H-NMR (DMSO-d₆): δ1.31 (d, J=6.03 Hz, 6H), 3.55 (dt, J=4.57, 2.52 Hz, 2H), 4.43 (s, 2H), 4.49 (dt, J=4.52, 2.45 Hz, 2H), 5.13 (quintet, J=6.17 Hz, 1H), 7.99 (s, 1H), 9.64 (brs, 2H)

ESI-MS (free base): m/z 210 (M+H)⁺.

Example 3

3-[(1R)-1-cyclopropylethoxy]-6,7,8,9-tetrahydropyrazino[2,3-f][1,4]oxazepine hydrochloride

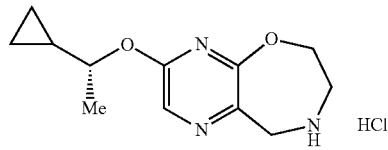

To a solution of 8-benzyl-3-[(1R)-1-cyclopropylethoxy]-6,7,8,9-tetrahydropyrazino[2,3-f][1,4]oxazepine (32.9 mg) in toluene (3 mL) was added 1-chloroethyl chloroformate (0.11 mL), and the mixture was stirred at 90° C. for 3 hr. The reaction mixture was cooled to room temperature, and concentrated. To the obtained residue was added methanol (3 mL), and the mixture was stirred at 60° C. for 1 hr. The reaction mixture was cooled to room temperature, and concentrated. The concentrate was diluted with ethyl acetate, and washed with saturated aqueous sodium hydrogen carbonate, water and saturated brine. The organic layer was dried over anhydrous magnesium sulfate, and concentrated under reduced pressure. The obtained residue was purified by basic silica gel column chromatography (solvent gradient; 10→100% ethyl acetate/hexane). To a solution of the obtained oil in methanol (1 mL) was added 1 N hydrochloric acid (0.45 mL), and the mixture was concentrated under reduced pressure. The obtained crude crystals were purified by recrystallization (ethanol-diisopropyl ether) to give the title compound (8.6 mg, 3%) as colorless crystals.

¹H-NMR (DMSO-d₅): δ0.35 (d, 2H), 0.42-0.60 (M, 2H), 1.01-1.25 (M, 1H), 1.33 (d, J=6.03 Hz, 3H), 3.45-3.64 (M, 2H), 4.29-4.67 (M, 5H), 8.01 (s, 1H), 9.55 (brs, 2H)

ESI-MS (free base): m/z 236 (M+H)⁺.

Example 4

3-(morpholin-4-yl)-6,7,8,9-tetrahydropyrazino[2,3-f][1,4]oxazepine

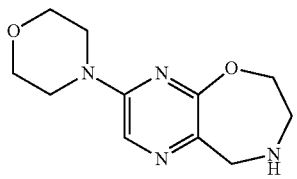

A mixture of 8-benzyl-3-(morpholin-4-yl)-6,7,8,9-tetrahydropyrazino[2,3-f][1,4]oxazepine (259 mg), 20% Pd(OH)₂/C (300 mg) and methanol (2 mL) was stirred under a hydrogen atmosphere at 50° C. for 2 hr. Insoluble material was filtered off, and the filtrate was concentrated under reduced pressure. The residue was purified by basic silica gel column chromatography (solvent gradient; 0→10% methanol/ethyl acetate) and recrystallized (ethyl acetate-hexane) to give the title compound (54.1 mg, 29%) as colorless crystals.

$^1$H-NMR (CDCl$_2$): δ3.11-3.35 (M, 2H), 3.45-3.65 (M, 4H), 3.73-3.88 (m, 4H), 4.08 (s, 2H), 4.17-4.34 (M, 2H), 7.71 (s, 1H)

Example 5

3-[(3R)-3-methylmorpholin-4-yl]-6,7,8,9-tetrahydropyrazino[2,3-f][1,4]oxazepine hydrochloride

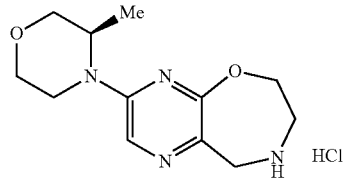

A mixture of 8-benzyl-3-[(3R)-3-methylmorpholin-4-yl]-6,7,8,9-tetrahydropyrazino[2,3-f][1,4]oxazepine (124 mg), 20% Pd(OH)$_2$/C (60 mg) and methanol (3 mL) was stirred under a hydrogen atmosphere at 50° C. for 2 hr. Insoluble material was filtered off, and the filtrate was concentrated under reduced pressure. The residue was purified by basic silica gel column chromatography (solvent gradient; 10→100% ethyl acetate/hexane). To a solution of the obtained oil in methanol (1 mL) was added 1 N hydrochloric acid (0.28 mL), and the mixture was concentrated under reduced pressure. The obtained crude crystals were purified by recrystallization (ethanol-diisopropyl ether) to give the title compound (62.6 mg, 60%) as colorless crystals.

$^1$H-NMR (DMSO-d$_6$): δ1.15 (d, 3H), 3.12 (td, J=12.72, 3.96 Hz, 1H), 3.39-3.55 (M, 3H), 3.56-3.65 (M, 1H), 3.67-3.76 (M, 1H), 3.82-3.99 (M, 2H), 4.24-4.35 (M, 3H), 4.38 (dt, J=4.43, 2.50 Hz, 2H), 7.98 (s, 1H), 9.59 (brs, 2H)

A mixture of 8-benzyl-3-[(3R)-3-methylmorpholin-4-yl]-6,7,8,9-tetrahydropyrazino[2,3-f][1,4]oxazepine (733 mg), 20% Pd(OH)$_2$/C (300 mg) and methanol (5 mL) was stirred under a hydrogen atmosphere at 50° C. for 2 hr. Insoluble material was filtered off, and the filtrate was concentrated under reduced pressure. The residue was purified by basic silica gel column chromatography (solvent gradient; 5→100% ethyl acetate/hexane). To a solution of the obtained oil in methanol (3 mL) was added 1 N hydrochloric acid (1.8 mL), and the mixture was concentrated under reduced pressure. The obtained crude crystals were purified by recrystallization (ethanol-diisopropyl ether) to give the title compound as crystals (418 mg, 68%).

powder X ray crystal diffraction: 2θ(°)=5.14, 9.76, 10.36, 12.24, 15.62, 16.14, 16.96, 18.98, 20.66, 20.90, 22.68, 23.74, 24.86

Example 6

(6S)-6-methyl-3-(morpholin-4-yl)-6,7,8,9-tetrahydropyrazino[2,3-f][1,4]oxazepine

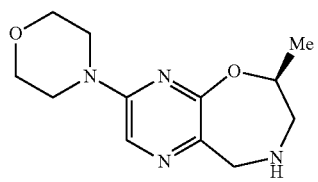

A mixture of (6S)-8-benzyl-6-methyl-3-(morpholin-4-yl)-6,7,8,9-tetrahydropyrazino[2,3-f][1,4]oxazepine (70 mg), 20% Pd(OH)$_2$/C (70 mg) and methanol (2 mL) was stirred under a hydrogen atmosphere at 50° C. for 2 hr. Insoluble material was filtered off, and the filtrate was concentrated under reduced pressure. The residue was purified by basic silica gel column chromatography (solvent gradient; 20→100% ethyl acetate/hexane) and recrystallized (ethyl acetate-hexane) to give the title compound (11.1 mg, 21%) as colorless crystals.

$^1$H-NMR (CDCl$_3$): δ1.40 (d, 3H), 3.00 (dd, J=14.20, 9.66 Hz, 1H), 3.13-3.27 (M, 1H), 3.41-3.57 (M, 4H), 3.71-3.85 (M, 4H), 3.90-4.04 (M, 1H), 4.06-4.19 (M, 1H), 4.19-4.33 (M, 1H), 7.69 (s, 1H)

ESI-MS: m/z 251 (M+H)$^+$.

Example 7

(6S)-6-methyl-3-[(3R)-3-methylmorpholin-4-yl]-6,7,8,9-tetrahydropyrazino[2,3-f][1,4]oxazepine hydrochloride

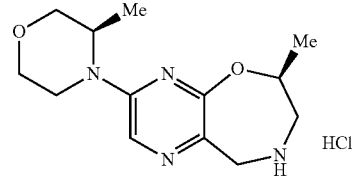

A mixture of (6S)-8-benzyl-6-methyl-3-[(3R)-3-methylmorpholin-4-yl]-6,7,8,9-tetrahydropyrazino[2,3-f][1,4]oxazepine (233 mg), 20% Pd(OH)$_2$/C (200 mg) and methanol (4 mL) was stirred under a hydrogen atmosphere at 50° C. for 2 hr. Insoluble material was filtered off, and the filtrate was concentrated under reduced pressure. The residue was purified by basic silica gel column chromatography (solvent gradient; 10→100% ethyl acetate/hexane). To a solution of the obtained oil in methanol (2 mL) was added 1 N hydrochloric acid (0.42 mL), and the mixture was concentrated under reduced pressure. The obtained crude crystals were purified by recrystallization (ethanol-diisopropyl ether) to give the title compound (94.7 mg, 48%) as colorless crystals.

$^1$H-NMR (DMSO-d$_6$): δ1.14 (d, J=6.78 Hz, 3H), 1.37 (d, J=6.40 Hz, 3H), 3.13 (td, J=12.62, 3.77 Hz, 1H), 3.38-3.56 (M, 2H), 3.56-3.67 (M, 1H), 3.67-3.77 (M, 1H), 3.77-4.02 (M, 3H), 4.18 (d, J=15.07 Hz, 1H), 4.26-4.37 (M, 1H), 4.43 (d, J=14.69 Hz, 1H), 4.49-4.65 (M, 1H), 7.97 (s, 1H), 9.79 (brs, 2H)

ESI-MS (free base): m/z 265 (M+H)$^+$.

Example 8

N-methyl-N-(1-methylethyl)-6,7,8,9-tetrahydropyrazino[2,3-f][1,4]oxazepin-3-amine hydrochloride

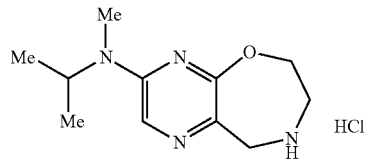

A mixture of 8-benzyl-N-methyl-N-(1-methylethyl)-6,7,8,9-tetrahydropyrazino[2,3-f][1,4]oxazepin-3-amine (79 mg), 20% Pd(OH)$_2$/C (80 mg) and methanol (2 mL) was stirred under a hydrogen atmosphere at 50° C. for 1 hr. Insoluble material was filtered off, and the filtrate was concentrated under reduced pressure. The residue was purified by basic silica gel column chromatography (solvent gradient; 10→100% ethyl acetate/hexane). To a solution of the obtained oil in methanol (2 mL) was added 1 N hydrochloric acid (0.19 mL), and the mixture was concentrated under reduced pressure. The obtained crude crystals were purified by recrystallization (ethanol-diisopropyl ether) to give the title compound (37.3 mg, 57%) as colorless crystals.

$^1$H-NMR (DMSO-d$_6$): δ1.12 (d, 6H), 2.85 (s, 3H), 3.49 (dt, J=4.52, 2.26 Hz, 2H), 4.30 (s, 2H), 4.36 (dt, J=4.52, 2.26 Hz, 2H), 4.66 (quintet, J=6.69 Hz, 1H), 7.85 (s, 1H), 9.53 (brs, 2H)

ESI-MS (free base): m/z 223 (M+H)$^+$.

The title compound (300 mg) was dissolved in methanol (about 6 mL), and the mixture was filtered. The solvent was evaporated while stirring the filtrate at 5° C. under a nitrogen stream, and the precipitated crystals were collected by filtration to give the title compound as crystals (280 mg).

powder X ray crystal diffraction: 2θ(°)=8.10, 10.26, 12.90, 16.28, 16.70, 19.98, 23.02, 24.14, 24.60, 26.04

Example 9

3-[(3R)-3-ethylmorpholin-4-yl]-6,7,8,9-tetrahydropyrazino[2,3-f][1,4]oxazepine hydrochloride

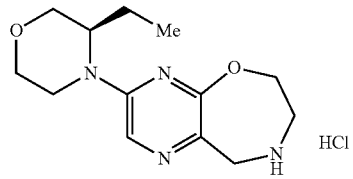

A mixture of 8-benzyl-3-[(3R)-3-ethylmorpholin-4-yl]-6,7,8,9-tetrahydropyrazino[2,3-f][1,4]oxazepine (130 mg), 20% Pd(OH)$_2$/C (80 mg) and methanol (2 mL) was stirred under a hydrogen atmosphere at 50° C. for 1 hr. Insoluble material was filtered off, and the filtrate was concentrated under reduced pressure. The residue was purified by basic silica gel column chromatography (solvent gradient; 10→100% ethyl acetate/hexane). To a solution of the obtained oil in methanol (1 mL) was added 1 N hydrochloric acid (0.27 mL), and the mixture was concentrated under reduced pressure. The obtained crude crystals were purified by recrystallization (ethanol-diisopropyl ether) to give the title compound (66.7 mg, 60%) as colorless crystals.

$^1$H-NMR (DMSO-d$_6$): δ0.84 (t, J=4.90 Hz, 3H), 1.46-1.86 (M, 2H), 3.12 (td, J=12.72, 3.96 Hz, 1H), 3.37-3.56 (M, 4H), 3.75-4.02 (m, 3H), 4.05-4.18 (M, 1H), 4.31 (s, 2H), 4.38 (d, J=4.14 Hz, 2H), 7.99 (s, 1H), 9.53 (brs, 2H)

ESI-MS (free base): m/z 265 (M+H)$^+$.

Example 10

3-cyclopropyl-6,7,8,9-tetrahydropyrazino[2,3-f][1,4]oxazepine hydrochloride

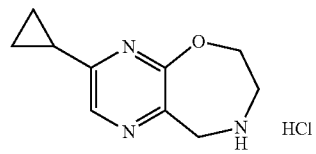

To a solution of 8-benzyl-3-cyclopropyl-6,7,8,9-tetrahydropyrazino[2,3-f][1,4]oxazepine (79.9 mg) in toluene (3 mL) was added 1-chloroethyl chloroformate (0.033 mL), and the mixture was stirred at 100° C. for 3 hr. The reaction mixture was cooled to room temperature, and concentrated. To the obtained residue was added methanol (3 mL) and the mixture was stirred at 60° C. for 2 hr. The reaction mixture was cooled to room temperature, and concentrated. The concentrate was diluted with ethyl acetate, and washed with saturated aqueous sodium hydrogen carbonate, water and saturated brine. The organic layer was dried over anhydrous magnesium sulfate, and concentrated under reduced pressure. The obtained residue was purified by basic silica gel column chromatography (solvent gradient; 10→100% ethyl acetate/hexane). To a solution of the obtained oil in methanol (1 mL) was added 0.1 N hydrochloric acid (0.6 mL), and the mixture was concentrated under reduced pressure. The obtained crude crystals were purified by recrystallization (ethanol-diisopropyl ether) to give the title compound (10.2 mg, 16%) as colorless crystals.

$^1$H-NMR (DMSO-d$_6$): δ0.81-0.94 (M, 2H), 0.98-1.16 (M, 2H), 1.95-2.26 (M, 1H), 3.53 (dt, J=4.43, 2.50 Hz, 2H), 4.29-4.61 (M, 4H), 8.39 (s, 1H), 9.72 (brs, 2H)

ESI-MS (free base): m/z 192 (M+H)$^+$.

Example 11

3-(cyclopent-1-en-1-yl)-6,7,8,9-tetrahydropyrazino[2,3-f][1,4]oxazepine hydrochloride

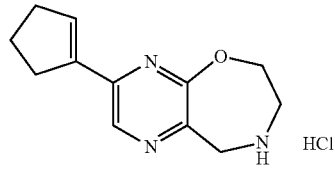

To a solution of 8-benzyl-3-(cyclopent-1-en-1-yl)-6,7,8,9-tetrahydropyrazino[2,3-f][1,4]oxazepine (99 mg) in toluene (1 mL) was added 1-chloroethyl chloroformate (0.038 mL), and the mixture was stirred at 90° C. for 4 hr. 1-Chloroethyl chloroformate (0.038 mL) was further added, and the mixture was stirred at 90° C. for 1 hr. The reaction mixture was cooled to room temperature, and concentrated. To the obtained residue was added methanol (1 mL), and the mixture was stirred at 60° C. for 0.5 hr. The reaction mixture was cooled to room temperature, and concentrated. The concentrate was diluted with ethyl acetate, and washed with saturated aqueous sodium hydrogen carbonate, water and saturated brine. The organic layer was dried over anhydrous magnesium sulfate, and concentrated under reduced pressure. The obtained residue was purified by basic silica gel column chromatography (solvent gradient; 10→100% ethyl acetate/hexane). To a solution of the obtained oil in methanol (1 mL) was added 1 N hydrochloric acid (0.18 mL), and the mixture was concentrated under reduced pressure. The obtained crude crystals were purified by recrystallization (ethanol-diisopropyl ether) to give the title compound (41.1 mg, 50%) as colorless crystals.

$^1$H-NMR (DMSO-$d_6$): δ1.98 (quintet, 2H), 2.53-2.61 (M, 2H), 2.63-2.79 (M, 2H), 3.56 (dt, J=4.71, 2.54 Hz, 2H), 4.36-4.61 (M, 4H), 6.83 (s, 1H), 8.59 (s, 1H), 9.70 (brs, 2H)

ESI-MS (free base): m/z 218 (M+H)$^+$.

Example 12

3-(2-methylpiperidin-1-yl)-6,7,8,9-tetrahydropyrazino[2,3-f][1,4]oxazepine hydrochloride

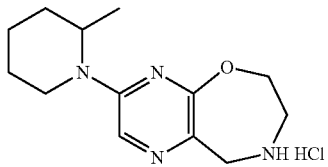

To a solution of 8-benzyl-3-(2-methylpiperidin-1-yl)-6,7,8,9-tetrahydropyrazino[2,3-f][1,4]oxazepine (0.65 g) in methanol (20 mL) was added 20% Pd(OH)$_2$/C (0.13 g), and the mixture was stirred under a hydrogen atmosphere at 50° C. for 2.5 hr. The reaction mixture was filtered, and the filtrate was concentrated. To a solution of the obtained crude product in ethyl acetate (20 mL) was added a 4 N hydrogen chloride-ethyl acetate solution (628 μL) and the mixture was stirred for 30 min. The reaction mixture was filtered, and the obtained crystals were purified by recrystallization (methanol-ethyl acetate) to give the title compound (0.40 g, 73%) as a pale-yellow powder.

$^1$H-NMR (DMSO-$d_6$): δ1.11 (d, J=6.8 Hz, 3H), 1.39 (d, J=4.1 Hz, 1H), 1.50-1.80 (M, 5H), 2.85-3.00 (M, 1H), 3.43-3.55 (M, 2H), 4.12 (dd, J=13.2, 2.6 Hz, 1H), 4.28 (s, 2H), 4.37 (dt, J=4.5, 2.3 Hz, 2H), 4.60 (d, J=6.4 Hz, 1H), 7.97 (s, 1H), 9.66 (brs, 2H).

ESI-MS (free base): m/z 249 (M+H)$^+$.

Example 13

3-(2-methylpyrrolidin-1-yl)-6,7,8,9-tetrahydropyrazino[2,3-f][1,4]oxazepine hydrochloride

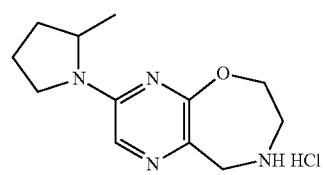

To a solution of 8-benzyl-3-(2-methylpyrrolidin-1-yl)-6,7,8,9-tetrahydropyrazino[2,3-f][1,4]oxazepine (0.51 g) in methanol (15 mL) was added 20% Pd(OH)$_2$/C (0.08 g), and the mixture was stirred under a hydrogen atmosphere at 50° C. for 1 hr. The reaction mixture was filtered, and the filtrate was concentrated. To a solution of the obtained crude product in ethyl acetate (15 mL) was added a 4 N hydrogen chloride-ethyl acetate solution (430 μL), and the mixture was stirred for 30 min. The reaction mixture was filtered, and the obtained crystals were purified by recrystallization (methanol-ethyl acetate) to give the title compound (0.30 g, 71%) as a colorless powder.

$^1$H-NMR (DMSO-$d_6$): δ1.10-1.20 (M, 3H), 1.62-1.76 (M, 1H), 1.88-2.12 (M, 3H), 3.23-3.29 (M, 1H), 3.44-3.57 (M, 3H), 4.12 (quin, J=5.77 Hz, 1H), 4.25-4.31 (M, 2H), 4.31-4.45 (M, 2H), 7.67 (s, 1H), 9.68 (brs, 2H).

ESI-MS (free base): m/z 235 (M+H)$^+$.

Example 14

N-methyl-N-(1-methylpropyl)-6,7,8,9-tetrahydropyrazino[2,3-f][1,4]oxazepin-3-amine hydrochloride

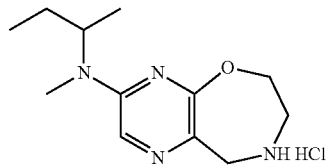

To a solution of 8-benzyl-N-methyl-N-(1-methylpropyl)-6,7,8,9-tetrahydropyrazino[2,3-f][1,4]oxazepin-3-amine (0.64 g) in methanol (20 mL) was added 20% Pd(OH)$_2$/C (0.13 g), and the mixture was stirred under a hydrogen atmosphere at 50° C. for 2 hr. The reaction mixture was filtered, and the filtrate was concentrated. To a solution of the obtained crude product in ethyl acetate (20 mL) was added a 4 N hydrogen chloride-ethyl acetate solution (540 μL), and the mixture was stirred for 30 min. The reaction mixture was filtered, and the obtained crystals were purified by recrystallization (methanol-ethyl acetate) to give the title compound (0.44 g, 82%) as a pale-yellow powder.

$^1$H-NMR (DMSO-$d_6$): δ0.76 (t, J=7.38 Hz, 3H), 1.09 (d, J=6.82 Hz, 3H), 1.53 (tq, J=13.68, 6.78 Hz, 2H), 2.82 (s, 3H), 3.49 (br.s, 2H), 4.30 (brs, 2H), 4.33-4.41 (M, 2H), 4.41-4.54 (M, 1H), 7.87 (s, 1H), 9.58 (br.s, 2H).

ESI-MS (free base): m/z 237 (M+H)$^+$.

Example 15

N-methyl-N-[(1R or S)-1-methylpropyl]-6,7,8,9-tetrahydropyrazino[2,3-f][1,4]oxazepin-3-amine hydrochloride

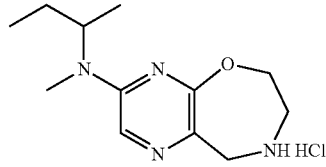

(Step 1)

To a solution of N-methyl-N-(1-methylpropyl)-6,7,8,9-tetrahydropyrazino[2,3-f][1,4]oxazepin-3-amine hydrochloride (0.38 g) in tetrahydrofuran-ethyl acetate (1:1, 20 mL)

was added a 1 M aqueous sodium hydroxide solution (8.3 mL), and the mixture was stirred at room temperature for 1 hr. The obtained reaction mixture was extracted with ethyl acetate. The aqueous layer was extracted again with ethyl acetate. The obtained crude product was optically resolved by CHIRALPAK AD JG0001, 50 mmID×500 mmL manufactured by Daicel Chemical Industries Limited (solvent: 80% ethanol/hexane) to give compound A (147 mg, >99.9% ee) with retention time 12.1 min and compound B (146 mg, 99.8% ee) with retention time 15 min each as a colorless oil.
(Step 2)

To a solution of compound A (147 mg, >99.9% ee) obtained in the above-mentioned step 1 in ethyl acetate (6 mL) was added a 4 N hydrogen chloride-ethyl acetate solution (170 μL), and the mixture was stirred for 1 hr. The reaction mixture was filtered, and the obtained crystals were purified by recrystallization (methanol-ethyl acetate) to give the title compound (0.11 g, 65%) as a colorless powder.

$^1$H-NMR (DMSO-$d_6$): δ0.76 (t, J=7.35 Hz, 3H), 1.09 (d, J=6.40 Hz, 3H), 1.53 (dq, J=13.70, 6.99 Hz, 2H), 2.82 (s, 3H), 3.47 (dt, J=4.62, 2.40 Hz, 2H), 4.28 (s, 2H), 4.37 (dt, J=4.33, 2.35 Hz, 2H), 4.41-4.54 (M, 1H), 7.86 (s, 1H), 9.73 (brs, 2H).

ESI-MS (free base): m/z 237 (M+H)$^+$.

Example 16

N-methyl-N-[(1R or S)-1-methylpropyl]-6,7,8,9-tetrahydropyrazino[2,3-f][1,4]oxazepin-3-amine hydrochloride

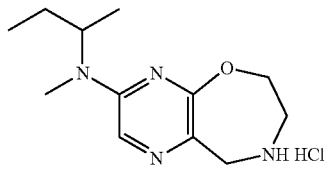

To a solution of compound B (146 mg, 99.8% ee) obtained in step 1 of Example 15 in ethyl acetate (6 mL) was added a 4 N hydrogen chloride-ethyl acetate solution (170 μL), and the mixture was stirred for 1 hr. The reaction mixture was filtered, and the obtained crystals were purified by recrystallization (methanol-ethyl acetate) to give the title compound (0.10 g, 65%) as a colorless powder.

$^1$H-NMR (DMSO-$d_6$): δ0.75 (t, J=7.35 Hz, 3H), 1.09 (d, J=6.78 Hz, 3H), 1.45-1.62 (M, 2H), 2.82 (s, 3H), 3.48 (dt, J=4.33, 2.35 Hz, 2H), 4.29 (s, 2H), 4.36 (dt, J=4.52, 2.26 Hz, 2H), 4.41-4.54 (M, 1H), 7.87 (s, 1H), 9.54 (brs, 2H).

ESI-MS (free base): m/z 237 (M+H)$^+$.

Example 17

N-(cyclopropylmethyl)-N-methyl-6,7,8,9-tetrahydropyrazino[2,3-f][1,4]oxazepin-3-amine hydrochloride

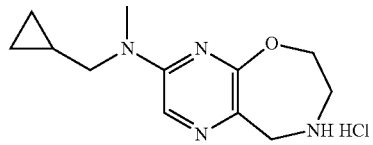

To a solution of 8-benzyl-N-(cyclopropylmethyl)-N-methyl-6,7,8,9-tetrahydropyrazino[2,3-f][1,4]oxazepin-3-amine (0.36 g) in methanol (10 mL) was added 20% Pd(OH)$_2$/C (70 mg), and the mixture was stirred under a hydrogen atmosphere at 50° C. for 2.5 hr. The reaction mixture was filtered, and the filtrate was concentrated. To a solution of the obtained crude product in ethyl acetate (10 mL) was added a 4 N hydrogen chloride-ethyl acetate solution (300 μL), and the mixture was stirred for 30 min. The reaction mixture was filtered, and the obtained crystals were purified by recrystallization (methanol-ethyl acetate) to give the title compound (197 mg, 67%) as a colorless powder.

$^1$H-NMR (DMSO-$d_6$): δ0.23-0.32 (M, 2H), 0.40-0.50 (M, 2H), 0.94-1.08 (M, 1H), 3.08 (s, 3H), 3.41 (d, J=6.82 Hz, 2H), 3.48 (dt, J=4.73, 2.18 Hz, 2H), 4.29 (s, 2H), 4.37 (dt, 4.54, 2.27 Hz, 2H), 7.87 (s, 1H), 9.70 (brs, 2H).

ESI-MS (free base): m/z 235 (M+H)$^+$.

Example 18

N-cyclobutyl-N-methyl-6,7,8,9-tetrahydropyrazino[2,3-f][1,4]oxazepin-3-amine hydrochloride

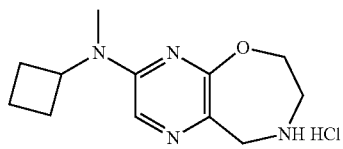

To a solution of 8-benzyl-N-cyclobutyl-N-methyl-6,7,8,9-tetrahydropyrazino[2,3-f][1,4]oxazepin-3-amine (0.48 g) in methanol (10 mL) was added 20% Pd(OH)$_2$/C (90 mg), and the mixture was stirred under a hydrogen atmosphere at 50° C. for 3 hr. The reaction mixture was filtered, and the filtrate was concentrated. To a solution of the obtained crude product in ethyl acetate (10 mL) was added a 4 N hydrogen chloride-ethyl acetate solution (400 μL), and the mixture was stirred for 30 min. The reaction mixture was filtered, and the obtained crystals were purified by recrystallization (methanol-ethyl acetate) to give the title compound (257 mg, 65%) as a colorless powder.

$^1$H-NMR (DMSO-$d_6$): δ1.56-1.75 (M, 2H), 2.09-2.24 (M, 4H), 2.96-3.03 (M, 3H), 3.47 (dt, J=4.54, 2.27 Hz, 2H), 4.25-4.32 (M, 2H), 4.38 (dt, J=4.54, 2.27 Hz, 2H), 4.71 (t, J=8.52 Hz, 1H), 7.83 (s, 1H), 9.87 (brs, 2H).

ESI-MS (free base): m/z 235 (M+H)$^+$.

Example 19

N-benzyl-N-(1-methylethyl)-6,7,8,9-tetrahydropyrazino[2,3-f][1,4]oxazepin-3-amine hydrochloride

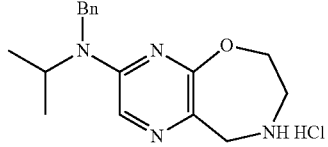

To a solution of N,8-benzyl-N-(1-methylethyl)-6,7,8,9-tetrahydropyrazino[2,3-f][1,4]oxazepin-3-amine (2.55 g) in methanol (20 mL) was added 20% Pd(OH)$_2$/C (260 mg), and the mixture was stirred under a hydrogen atmosphere at 50° C. for 2 hr. 20% Pd(OH)$_2$/C (500 mg) was further added, and the mixture was stirred under a hydrogen atmosphere at 50° C. for 4 hr. The reaction mixture was filtered, and the filtrate was concentrated to give a colorless oil (1.95 g). 53 mg of this oil was dissolved in ethyl acetate (1 mL), a 4 N hydrogen chloride-ethyl acetate solution (49 μL) was added, and the mixture was stirred for 30 min. The reaction mixture was filtered, and the obtained crystals were purified by recrystallization (ethanol-diisopropyl ether) to give the title compound (47 mg, 79%) as a pale-yellow powder.

$^1$H-NMR (DMSO-d$_6$): δ1.15 (d, J=6.40 Hz, 6H), 3.47 (brs, 2H), 4.28 (brs, 2H), 4.35-4.41 (M, 2H), 4.66 (s, 2H), 4.82 (quin, J=6.59 Hz, 1H), 7.18-7.36 (M, 5H), 7.60 (s, 1H), 9.67 (brs, 2H).

ESI-MS (free base): m/z 299 (M+H)$^+$

Example 20

N-(D$_3$)methyl-N-(1-methylethyl)-6,7,8,9-tetrahydropyrazino[2,3-f][1,4]oxazepin-3-amine hydrochloride

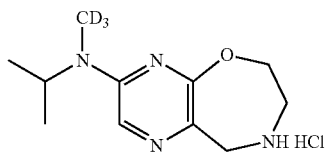

To a solution of tert-butyl 3-[(D$_3$)methyl-(1-methylethyl)amino]-6,7-dihydropyrazino[2,3-f][1,4]oxazepine-8(9H)-carboxylate (66 mg) in ethyl acetate (0.5 mL) was added 4 N hydrogen chloride-ethyl acetate solution (0.5 mL), and the mixture was stirred for 1.5 hr. The reaction mixture was basified with saturated aqueous sodium hydrogen carbonate solution, and extracted with ethyl acetate. The aqueous layer was extracted again with ethyl acetate. The combined organic layer was washed with water and saturated brine, dried over magnesium sulfate, and concentrated. To a solution of the obtained crude product in methanol (1 mL) was added 1.0 N hydrochloric acid (156 μL), and the mixture was stirred for 30 min. The reaction mixture was concentrated, and the obtained crystals were purified by recrystallization (methanol-ethyl acetate) to give the title compound (6 mg, 61%) as a pale-yellow powder.

$^1$H-NMR (DMSO-d$_6$): δ1.12 (d, J=6.78 Hz, 6H), 3.48 (dt, J=4.80, 2.31 Hz, 2H), 4.29 (s, 2H), 4.35 (dt, J=4.52, 2.26 Hz, 2H), 4.66 (quin, J=6.69 Hz, 1H), 7.84 (s, 1H), 9.48 (brs, 2H).

ESI-MS (free base): m/z 226 (M+H)$^+$.

Example 21

N-ethyl-N-(1-methylethyl)-6,7,8,9-tetrahydropyrazino[2,3-f][1,4]oxazepin-3-amine hydrochloride

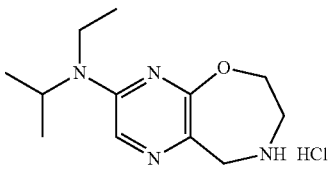

To a solution of tert-butyl 3-[ethyl(1-methylethyl)amino]-6,7-dihydropyrazino[2,3-f][1,4]oxazepine-8(9H)-carboxylate (10 mg) in ethyl acetate (0.1 mL) was added 4 N hydrogen chloride-ethyl acetate solution (0.5 mL), and the mixture was stirred for 30 min. The reaction mixture was basified with saturated aqueous sodium hydrogen carbonate solution, and extracted with ethyl acetate. The aqueous layer was extracted again with ethyl acetate. The combined organic layer was washed with water and saturated brine, dried over magnesium sulfate, and concentrated. To a solution of the obtained crude product in methanol (0.5 mL) was added 1.0 N hydrochloric acid (33 μL), and the mixture was stirred for 5 min. The reaction mixture was concentrated, and the obtained crystals were purified by recrystallization (ethanol-diisopropyl ether) to give the title compound (10 mg, 100%) as a pale-yellow powder.

$^1$H-NMR (DMSO-d$_6$): δ1.06-1.22 (M, 9H), 3.40 (q, J=7.03 Hz, 2H), 3.45-3.54 (M, 2H), 4.30 (s, 2H), 4.33-4.40 (M, 2H), 4.61 (dt, J=13.28, 6.73 Hz, 1H), 7.82 (s, 1H), 9.47 (brs, 2H).

ESI-MS (free base): m/z 237 (M+H)$^+$.

Example 22

N-methyl-N-propyl-6,7,8,9-tetrahydropyrazino[2,3-f][1,4]oxazepin-3-amine hydrochloride

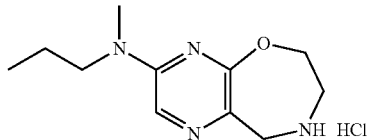

To a solution of 8-benzyl-N-methyl-N-propyl-6,7,8,9-tetrahydropyrazino[2,3-f][1,4]oxazepin-3-amine (50 mg) in methanol (4 mL) was added 20% Pd(OH)$_2$/C (10 mg), and the mixture was stirred under a hydrogen atmosphere at 50° C. for 2 hr. The reaction mixture was filtered, and the filtrate was concentrated. To a solution of the obtained crude product in ethyl acetate (2 mL) was added a 4 N hydrogen chloride-ethyl acetate solution (44 μL), and the mixture was stirred for 30 min. The reaction mixture was filtered, and the obtained crystals were purified by recrystallization (methanol-ethyl acetate) to give the title compound (27 mg, 65%) as a colorless powder.

$^1$H-NMR (DMSO-d$_6$): δ0.86 (t, J=7.16 Hz, 3H), 1.54 (dq, J=14.18, 6.83 Hz, 2H), 3.02 (s, 3H), 3.47 (d, J=6.03 Hz, 4H), 4.22-4.44 (m, 4H), 7.85 (s, 1H), 9.68 (brs, 2H).

ESI-MS (free base): m/z 223 (M+H)$^+$.

Example 23

N-(1-methylethyl)-6,7,8,9-tetrahydropyrazino[2,3-f][1,4]oxazepin-3-amine hydrochloride

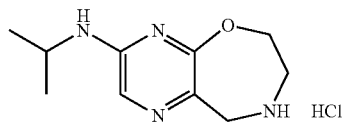

tert-Butyl 3-[(1-methylethyl)amino]-6,7-dihydropyrazino[2,3-f][1,4]oxazepine-8(9H)-carboxylate (72 mg) and TFA (2 mL) were stirred at room temperature for 30 min. The solvent was evaporated under reduced pressure, a saturated sodium hydrogen carbonate solution was added to the residue, and the mixture was extracted with an ethyl acetate-THF mixed solution (1:1). The extract was washed with water and saturated brine and dried over magnesium sulfate, and the solvent was evaporated under reduced pressure. The residue was dissolved in methanol, and the mixture was purified using an ion exchange resin (Argonaut Inc., SPE column MP-TsOH) (eluate: 2 M ammonia/methanol). To the obtained residue was added 1 N hydrochloric acid (0.184 mL) and the mixture was recrystallized from ethanol-diethyl ether-diisopropyl ether to give the title compound (27 mg, 48%).

$^1$H-NMR (DMSO-d$_6$): δ1.14 (d, J=6.4 Hz, 6H), 3.45 (brs, 2H), 3.79-3.98 (M, 1H), 4.25 (brs, 2H), 4.31-4.38 (M, 2H), 7.28 (d, J=6.8 Hz, 1H), 7.61 (s, 1H), 9.50 (brs, 2H).

Example 24

6,7,8,9-tetrahydropyrazino[2,3-f][1,4]oxazepin-3-amine

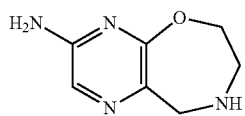

A mixture of 8-benzyl-6,7,8,9-tetrahydropyrazino[2,3-f][1,4]oxazepin-3-amine (87 mg), 20% Pd(OH)$_2$/C (150 mg) and methanol (2 mL) was stirred under a hydrogen atmosphere at 50° C. for 1 hr. Insoluble material was filtered off, and the filtrate was concentrated under reduced pressure. The residue was purified by recrystallization (ethanol-hexane) to give the title compound (19.7 mg, 35%) as colorless crystals.

$^1$H-NMR (CDCl$_3$): δ3.08-3.43 (M, 2H), 4.07 (s, 2H), 4.22 (d, J=9.42 Hz, 2H), 4.44 (brs, 2H), 7.61 (s, 1H).

Example 25

3-(2,5-dimethyl-1H-pyrrol-1-yl)-6,7,8,9-tetrahydropyrazino[2,3-f][1,4]oxazepine hydrochloride

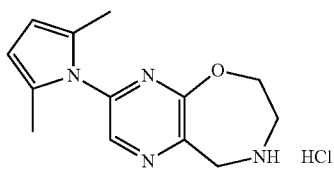

To a solution of 8-benzyl-3-(2,5-dimethyl-1H-pyrrol-1-yl)-6,7,8,9-tetrahydropyrazino[2,3-f][1,4]oxazepine (60 mg) in methanol (4 mL) was added 20% Pd(OH)$_2$/C (10 mg), and the mixture was stirred under a hydrogen atmosphere at 50° C. for 2 hr. The reaction mixture was filtered, and the filtrate was concentrated. To a solution of the obtained crude product in ethyl acetate (4 mL) was added a 4 N hydrogen chloride-ethyl acetate solution (50 μL), and the mixture was stirred for 30 min. The reaction mixture was filtered to give the title compound (28 mg, 56%) as a brown powder.

$^1$H-NMR (DMSO-d$_6$): δ2.11 (s, 6H), 3.30-3.90 (M, 2H), 4.53-4.73 (M, 4H), 5.88 (s, 2H), 8.53 (s, 1H), 10.10 (brs, 2H).
ESI-MS (free base): m/z 245 (M+H)$^+$.

Example 26

3-(2-methyl-1H-imidazol-1-yl)-6,7,8,9-tetrahydropyrazino[2,3-f][1,4]oxazepine hydrochloride

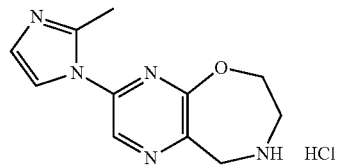

To a solution of 8-benzyl-3-(2-methyl-1H-imidazol-1-yl)-6,7,8,9-tetrahydropyrazino[2,3-f][1,4]oxazepine (18 mg) in methanol (2.5 mL) was added 20% Pd(OH)$_2$/C (10 mg), and the mixture was stirred under a hydrogen atmosphere at 50° C. for 5 hr. The reaction mixture was filtered, and the filtrate was concentrated. To a solution of the obtained crude product in methanol (0.3 mL) was added 0.1 N hydrochloric acid (410 μL), and the mixture was stirred for 30 min. The reaction mixture was concentrated, and the obtained crystals were purified by recrystallization (methanol-ethyl acetate) to give the title compound (6 mg, 61%) as a pale-yellow powder.

$^1$H-NMR (DMSO-d$_6$): δ2.59 (s, 3H), 3.58-3.65 (M, 2H), 4.59 (s, 2H), 4.62-4.70 (M, 2H), 7.17 (s, 1H), 7.81 (d, J=1.88 Hz, 1H), 8.77 (s, 1H), 10.27 (brs, 2H).

Example 27

2-chloro-N-methyl-N-(1-methylethyl)-6,7,8,9-tetrahydropyrazino[2,3-f][1,4]oxazepin-3-amine hydrochloride

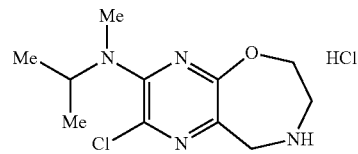

To a solution of 8-benzyl-2-chloro-N-methyl-N-(1-methylethyl)-6,7,8,9-tetrahydropyrazino[2,3-f][1,4]oxazepin-3-amine (200 mg) in toluene (3 mL) was added 1-chloroethyl chloroformate (0.075 mL), and the mixture was stirred at 80° C. for 2 hr. The reaction mixture was cooled to room temperature, and concentrated. To the obtained residue was added methanol (3 mL) and the mixture was stirred at 80° C. for 1 hr. The reaction mixture was cooled to room temperature, and concentrated. The obtained residue was purified by recrystallization (methanol-diisopropyl ether) to give the title compound (102 mg, 60%) as pale-yellow crystals.

$^1$H-NMR (DMSO-d$_6$): δ1.16 (d, J=6.44 Hz, 6H), 2.82 (s, 3H), 3.48-3.61 (M, 2H), 4.30-4.40 (M, 3H), 4.43 (dt, J=4.54, 2.27 Hz, 2H), 9.63 (brs, 2H).
ESI-MS (free base): m/z 257 (M+H)$^+$.

Example 28

2-bromo-N-methyl-N-(1-methylethyl)-6,7,8,9-tetrahydropyrazino[2,3-f][1,4]oxazepin-3-amine hydrochloride

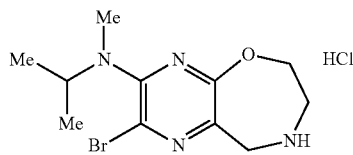

To a solution of 8-benzyl-2-bromo-N-methyl-N-(1-methylethyl)-6,7,8,9-tetrahydropyrazino[2,3-f][1,4]oxazepin-3-amine (122 mg) in toluene (2 mL) was added 1-chloroethyl chloroformate (0.040 mL), and the mixture was stirred at 80° C. for 2 hr. The reaction mixture was cooled to room temperature, and concentrated. To the obtained residue was added methanol (2 mL), and the mixture was stirred at 80° C. for 1 hr. The reaction mixture was cooled to room temperature, and concentrated. The obtained residue was purified by recrystallization (methanol-diisopropyl ether) to give the title compound (59 mg, 56%) as pale-yellow crystals.

$^1$H-NMR (DMSO-$d_6$): δ1.16 (d, J=6.82 Hz, 6H), 2.80 (s, $^3$H). 3.53 (brs, 2H), 4.22-4.38 (M, 3H), 4.42-4.50 (M, 2H), 9.61 (brs, 2H).

ESI-MS (free base): m/z 301 (M+H)$^+$.

Example 29

N,2-dimethyl-N-(1-methylethyl)-6,7,8,9-tetrahydropyrazino[2,3-f][1,4]oxazepin-3-amine hydrochloride

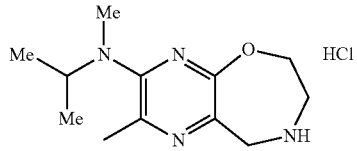

A mixture of tert-butyl 2-methyl-3-[methyl(1-methylethyl)amino]-6,7-dihydropyrazino[2,3-f][1,4]oxazepine-8(9H)-carboxylate (109 mg) and 2N hydrogen chloride-ethyl acetate (4 mL) was stirred at room temperature for 4 hr. The reaction mixture was basified with 1N sodium hydroxide, and extracted with ethyl acetate. The organic layer was washed with saturated brine, dried over sodium sulfate, and concentrated under reduced pressure. To the obtained residue were added methanol (5 mL) and 1 N hydrochloric acid (0.325 mL), and the mixture was concentrated under reduced pressure. The obtained residue was purified by recrystallization (ethanol-diisopropyl ether) to give the title compound (67 mg, 76%) as a colorless powder.

$^1$H-NMR (DMSO-$d_6$): δ1.13 (d, J=6.44 Hz, 6H), 2.41 (s, 3H), 2.71 (s, 3H), 3.49 (brs, 2H), 3.99 (dt, J=13.16, 6.48 Hz, 1H), 4.23-4.41 (M, 4H), 9.66 (brs, 2H).

ESI-MS (free base): m/z 237 (M+H)$^+$.

Example 30

3-[(1-methylethyl)sulfanyl]-6,7,8,9-tetrahydropyrazino[2,3-f][1,4]oxazepine hydrochloride

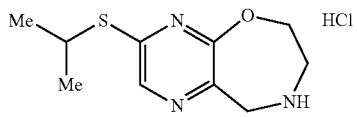

To a solution of 8-benzyl-3-[(1-methylethyl)sulfanyl]-6,7,8,9-tetrahydropyrazino[2,3-f][1,4]oxazepine (111 mg) in toluene (3 mL) was added 1-chloroethyl chloroformate (0.042 mL), and the mixture was stirred at 80° C. for 4 hr. The reaction mixture was cooled to room temperature, and concentrated. The obtained residue was purified by silica gel column chromatography (solvent gradient; 3→40% ethyl acetate/hexane). To the obtained oil was added methanol (3 mL), and the mixture was stirred at 80° C. for 2 hr. The reaction mixture was cooled to room temperature, and concentrated. The obtained residue was purified by recrystallization (ethanol-diisopropyl ether) to give the title compound (19.2 mg, 21%) as pale-yellow crystals.

$^1$H-NMR (DMSO-$d_6$): δ1.36 (d, J=6.8 Hz, 6H), 3.50-3.62 (M, 2H), 3.89 (quin, J=6.8 Hz, 1H), 4.46 (s, 2H), 4.49-4.57 (M, 2H), 8.30 (s, 1H), 9.65 (brs, 2H).

ESI-MS (free base): m/z 226 (M+H)$^+$.

Example 31

(6R)-6-(methoxymethyl)-N-methyl-N-(1-methylethyl)-6,7,8,9-tetrahydropyrazino[2,3-f][1,4]oxazepin-3-amine hydrochloride

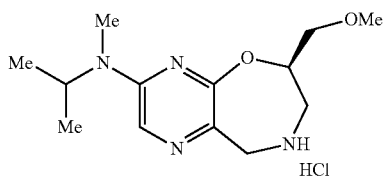

To a solution of (6R)-8-benzyl-6-(methoxymethyl)-N-methyl-N-(1-methylethyl)-6,7,8,9-tetrahydropyrazino[2,3-f][1,4]oxazepin-3-amine (261 mg) in methanol (7 mL) was added 20% Pd(OH)$_2$/C (40 mg), and the mixture was stirred under a hydrogen atmosphere at 50° C. for 7 hr. The reaction mixture was filtered, and the filtrate was concentrated under reduced pressure. To a solution of the obtained crude product in ethyl acetate (10 mL) was added a 4 N hydrogen chloride-ethyl acetate solution (200 µL), and the mixture was stirred for 30 min. The reaction mixture was filtered, and the obtained crystals were washed with ethyl acetate to give the title compound (136 mg, 61%).

$^1$H-NMR (DMSO-$d_6$): δ1.12 (dd, J=10.0, 6.6 Hz, 6H), 2.85 (s, 3H), 3.24-3.43 (M, 4H), 3.45-3.70 (M, 3H), 4.17 (d, J=15.1 Hz, 1H), 4.38-4.75 (M, 3H), 7.84 (s, 1H), 9.66 (brs, 2H).

ESI-MS (free base): m/z 267 (M+H)$^+$.

Example 32

(6R)-6-(methoxymethyl)-N-methyl-N-(1-methylpropyl)-6,7,8,9-tetrahydropyrazino[2,3-f][1,4]oxazepin-3-amine hydrochloride

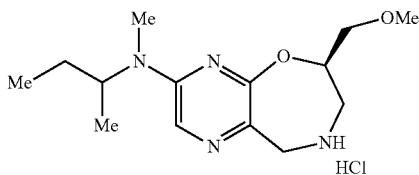

To a solution of (6R)-8-benzyl-6-(methoxymethyl)-N-methyl-N-(1-methylpropyl)-6,7,8,9-tetrahydropyrazino[2,3-f][1,4]oxazepin-3-amine (297 mg) in methanol (10 mL) was added 20% Pd(OH)$_2$/C (40 mg), and the mixture was stirred under a hydrogen atmosphere at 50° C. for 4 hr. The reaction mixture was filtered, and the filtrate was concentrated under reduced pressure. To a solution of the obtained crude product in ethyl acetate (10 mL) was added a 4 N hydrogen chloride-ethyl acetate solution (220 and the mixture was stirred for 1 hr. The reaction mixture was filtered, and the obtained crystals were washed with ethyl acetate to give the title compound (141 mg, 55%).

$^1$H-NMR (DMSO-d$_6$): δ0.69-0.81 (M, 3H), 1.04-1.14 (M, 3H), 1.45-1.63 (M, 2H), 2.82 (s, 3H), 3.34-3.42 (M, 4H), 3.46-3.69 (M, 3H), 4.17 (d, J=15.1 Hz, 1H), 4.38-4.63 (M, 3H), 7.80-7.95 (M, 1H), 9.64 (brs, 2H).

ESI-MS (free base): m/z 282 (M+H)$^+$.

Example 33

(6R)-6-(methoxymethyl)-N-methyl-N-propyl-6,7,8,9-tetrahydropyrazino[2,3-f][1,4]oxazepin-3-amine hydrochloride

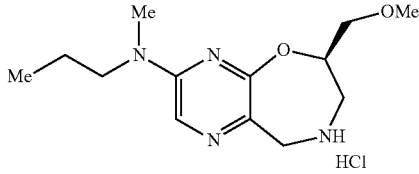

To a solution of (6R)-8-benzyl-6-(methoxymethyl)-N-methyl-N-propyl-6,7,8,9-tetrahydropyrazino[2,3-f][1,4]oxazepin-3-amine (465 mg) in methanol (10 mL) was added 20% Pd(OH)$_2$/C (50 mg), and the mixture was stirred under a hydrogen atmosphere at 50° C. for 3 hr. The reaction mixture was filtered, and the filtrate was concentrated under reduced pressure. To a solution of the obtained crude product in ethyl acetate (10 mL) was added a 4 N hydrogen chloride-ethyl acetate solution (359 μL), and the mixture was stirred for 1 hr. The reaction mixture was filtered, and the obtained crystals were washed with ethyl acetate to give the title compound (223 mg, 56%).

$^1$H-NMR (DMSO-d$_6$): δ0.86 (t, J=7.4 Hz, 3H), 1.47-1.63 (M, 2H), 3.02 (s, 3H), 3.23-3.69 (M, 9H), 4.16 (d, J=14.8 Hz, 1H), 4.43 (d, J=15.1 Hz, 1H), 4.52-4.62 (M, 1H), 7.84 (s, 1H), 9.78 (brs, 2H).

Example 34

(6R)-6-(methoxymethyl)-3-[2-(methoxymethyl)pyrrolidin-1-yl]-6,7,8,9-tetrahydropyrazino[2,3-f][1,4]oxazepine hydrochloride

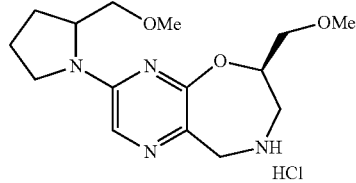

To a solution of (6R)-8-benzyl-6-(methoxymethyl)-3-[2-(methoxymethyl)pyrrolidin-1-yl]-6,7,8,9-tetrahydropyrazino[2,3-f][1,4]oxazepine (329 mg) in methanol (10 mL) was added 20% Pd(OH)$_2$/C (40 mg), and the mixture was stirred under a hydrogen atmosphere at 50° C. for 3 hr. The reaction mixture was filtered, and the filtrate was concentrated under reduced pressure. To a solution of the obtained crude product in ethyl acetate (10 mL) was added a 4 N hydrogen chloride-ethyl acetate solution (227 μL), and the mixture was stirred for 30 min. The reaction mixture was filtered, and the obtained crystals were washed with ethyl acetate to give the title compound (155 mg, 54%).

$^1$H-NMR (DMSO-d$_6$): δ1.85-2.08 (M, 4H), 3.21-3.45 (M, 10H), 3.45-3.69 (M, 4H), 4.12-4.25 (M, 2H), 4.43 (d, J=15.1 Hz, 1H), 4.51-4.61 (M, 1H), 7.74 (s, 1H), 9.81 (brs, 2H).

ESI-MS (free base): m/z 309 (M+H)$^+$.

Example 35

(6R)—N-cyclobutyl-6-(methoxymethyl)-N-methyl-6,7,8,9-tetrahydropyrazino[2,3-f][1,4]oxazepin-3-amine hydrochloride

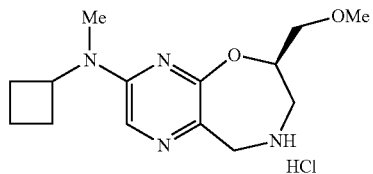

To a solution of (6R)-8-benzyl-N-cyclobutyl-6-(methoxymethyl)-N-methyl-6,7,8,9-tetrahydropyrazino[2,3-f][1,4]oxazepin-3-amine (390 mg) in methanol (10 mL) was added 20% Pd(OH)$_2$/C (50 mg), and the mixture was stirred under a hydrogen atmosphere at 50° C. for 6 hr. The reaction mixture was filtered, and the filtrate was concentrated under reduced pressure. To a solution of the obtained crude product in ethyl acetate (10 mL) was added a 4 N hydrogen chloride-ethyl acetate solution (291 μL), and the mixture was stirred for 5.5 hr. The reaction mixture was filtered, and the obtained crystals were washed with ethyl acetate to give the title compound (206 mg, 62%).

$^1$H-NMR (DMSO-$d_6$): δ1.58-1.73 (M, 2H), 2.07-2.27 (M, 4H), 2.99 (s, 3H), 3.28-3.42 (M, 8H), 3.46-3.68 (M, 3H), 4.17 (d, J=15.1 Hz, 1H), 4.44 (d, J=15.1 Hz, 1H), 4.53-4.63 (M, 1H), 4.65-4.80 (M, 1H), 7.83 (s, 1H), 9.82 (brs, 2H).

ESI-MS (free base): m/z 279 (M+H)$^+$.

Formulation Example 1

| | |
|---|---|
| (1) The compound of Example 1 | 10 mg |
| (2) Lactose | 60 mg |
| (3) Cornstarch | 35 mg |
| (4) Hydroxypropylmethylcellulose | 3 mg |
| (5) Magnesium stearate | 2 mg |

A mixture of 10 mg of the compound obtained in Example 1, 60 mg of lactose and 35 mg of corn starch is granulated using 0.03 mL of a 10 wt % aqueous hydroxypropylmethylcellulose solution (3 mg as hydroxypropylmethylcellulose), and then dried at 40° C. and sieved. The obtained granules are mixed with 2 mg of magnesium stearate and compressed. The obtained uncoated tablets are sugar-coated with an aqueous suspension of sucrose, titanium dioxide, talc and gum arabic. The thus-coated tablets are glazed with beeswax to give finally-coated tablets.

Formulation Example 2

| | |
|---|---|
| (1) The compound of Example 1 | 10 mg |
| (2) Lactose | 70 mg |
| (3) Cornstarch | 50 mg |
| (4) Soluble starch | 7 mg |
| (5) Magnesium stearate | 3 mg |

The compound (10 mg) obtained in Example 1 and 3 mg of magnesium stearate are granulated with 0.07 mL of an aqueous solution of soluble starch (7 mg as soluble starch), dried, and mixed with 70 mg of lactose and 50 mg of corn starch. The mixture is compressed to give tablets.

Reference Formulation Example 1

| | |
|---|---|
| (1) Rofecoxib | 5.0 mg |
| (2) Sodium chloride | 20.0 mg |
| (3) Distilled water | amount to make total volume 2.0 mL |

Rofecoxib (5.0 mg) and 20.0 mg of sodium chloride are dissolved in distilled water, and water is added to make the total volume 2.0 mL. The solution is filtered, and filled into 2 mL of ampoule under sterile condition. The ampoule is sterilized, and then sealed to give a solution for injection.

Reference Formulation Example 2

| | |
|---|---|
| (1) Rofecoxib | 50 mg |
| (2) Lactose | 34 mg |
| (3) Cornstarch | 10.6 mg |
| (4) Cornstarch (paste) | 5 mg |
| (5) Magnesium stearate | 0.4 mg |
| (6) Calcium carboxymethylcellulose | 20 mg |
| total | 120 mg |

The above-mentioned (1) to (6) are mixed according to a conventional method and the mixture is tableted by a tableting machine to give a tablet.

Formulation Example 3

The formulation prepared in Formulation Example 1 or 2, and the formulation prepared in Reference Formulation Example 1 or 2 are combined.

Experimental Example 1

The serotonin 5-HT$_{2C}$ receptor agonist activity of the compound of the present invention was evaluated based on the changes in the intracellular calcium concentration by the following method. After transcription, 5-HT$_{2C}$ undergoes RNA editing of the second intracellular loop, which results in the change of three amino acids and 14 receptor isoforms. 5-HT$_{2C}$ stably expressing CHO cell that expresses VSV type of the isoform stably was purchased from Euroscreen S.A., and cultured in UltraCHO (BioWhittaker) medium containing 1% dialyzed bovine serum and 400 μg/ml, G418. The cells were plated in a 384-well black clear bottom plate (PE Biosystems) at 5000 cells/well, and cultured for 24 hr in a $CO_2$ incubator, and changes in the intracellular calcium concentration mediated by the 5-HT$_2$ receptor were evaluated using Calcium Kit-Fluo 3 (Dojindo Laboratories). A calcium kit buffer containing 2.5 mM probenecid, 0.04% Pluronic F-127 and 2.5 μg Fluo-3 AM (calcium indicator fluorescent dye) was prepared and used as a Fluo-3 loading solution (contained in Dojindo Laboratories Calcium Kit). The loading solution was incubated at 37° C., the medium in the wells of the cell culture plate was removed, and the loading solution was added to each well by 40 μL. The cells were reacted at 37° C. for 1 hr to allow uptake of Fluo-3 AM into the cells and washed.

The compound of the present invention was diluted with a calcium kit buffer, and dispensed to each well of the 384-well plate (REMP) by 40 μL to give a test compound plate. The cell culture plate and test compound plate were set on a Fluometric Imaging Plate Reader (FLIPR, Molecular Devices), and changes in the intracellular calcium concentration were measured. An increase in the fluorescence intensity of Fluo-3 matches with an increase in the intracellular calcium concentration mediated by a receptor. The changes in the intracellular fluorescence intensity were measured every second with a CCD camera of FLIPR and, after measurement for 5 seconds before addition of the compound, a diluted solution of the compound of the present invention was added by 20 μL to each well of the cell culture plate using an automatic dispenser in FLIPR.

The agonist activity was evaluated based on the difference in the fluorescence level obtained by subtracting the fluorescence intensity before addition of the compound from the maximum fluorescence intensity after the addition thereof. The results are shown in Table 1. The activity of the test compound is shown by the ratio (%) relative to the maximum response by 5-HT.

TABLE 1

| Example No. of test compound | ratio (%) relative to maximum response by 5-HT (1 μM) |
|---|---|
| 2 | 93 |
| 5 | 95 |
| 6 | 102 |
| 7 | 108 |
| 8 | 95 |
| 9 | 103 |
| 10 | 89 |

Experimental Example 2

The oral absorbability of the compound of the present invention can be evaluated by the bioavailability after oral administration as shown below.

The compound of the present invention is intravenously and orally administered to IGS rats. The rat plasma samples are prepared after the serial blood sampling. The plasma concentration is measured using a liquid chromatograph-tandem mass spectrometry (LC/MS/MS), and bioavailability by oral administration is calculated from the ratio of area under curves.

Experimental Example 3

The phototoxicity of the compound of the present invention is evaluated by measuring the cell viability between light irradiation and non-irradiation according to the following method, or the method described in OECD Guideline for testing of chemicals: 432 in vitro 3T3 NRU phototoxicity test (Apr. 13, 2004) or a method analogous thereto.

Mouse embryonic cell line BALB/3T3 clone A31 cells are seeded in DMEM (Dulbecco's Modified Eagle Medium) containing 10% calf serum in a 384 well plate at $2.5 \times 10^3$ cells/well, and cultured in an incubator at 37° C., 5% $CO_2$ for 1 day. The culture medium is removed, the compound of the present invention dissolved in EBSS (Earle's Balanced Salt Solution) containing 10 mM HEPES (4-(2-hydroxyethyl)-1-piperazineethanesulfonic acid) buffer is added, and the mixture is cultured in an incubator at 37° C., 5% $CO_2$ for 1 hr, and subjected to a light irradiation treatment using a solar simulator (SXL-2500V2, Seric). As a control, a non-irradiation treatment group is prepared. The compound is removed, DMEM containing 10% calf serum is added, and the mixture is cultured in an incubator at 37° C., 5% $CO_2$ for 1 day. The ATP content of the cell is quantified using ATPLite™-M (PerkinElmer), and the cell viability is compared between the non-irradiation group and the irradiation group.

Experimental Example 4

The phototoxicity of the compound of the present invention is evaluated by determining the presence or absence of skin reaction upon light irradiation using the following method, or the methods shown in cited references (e.g., (1) Forbes, P. D., Urbach, F. and Davies, R. E. (1977). Phototoxicity Testing of Fragrance Raw Materials. Fd. Cosmet. Toxicol., Vol. 15, pp. 55-60, (2) Sambuco, C. P. and Forbes, P. D. (1984). Quantitative Assessment of Phototoxicity in the Skin of Hairless Mice. Fd. Chem. Toxic., Vol. 22, no. 3, pp. 233-236 etc.) according to Guidance for Industry: photosafety testing; May 2003 issued by U.S. Dept of Health and Human Services Food and Drug Administration (CDER), Rockville (MD).

The compound of the present invention is suspended in methylcellulose solution and orally administered to female hairless mice (Hos: HR-1, about 8-week-old, body weight 10-30 g) at doses up to 2000 mg/kg. After the administration, the mice are anesthetized by intraperitoneal administration of an aqueous chloral hydrate solution (60 mg/mL, about 0.15 mL/mouse). The mouse is fixed at the prone position, and the whole body is covered with an aluminum foil with an about 1.3 cm (diameter) hole. Ultraviolet ray corresponding to 0.5 MED (minimal erythema dose) generated by a solar light irradiation system (SXL-5009V1, Seric) is starting at a time corresponding to Tmax of the compound of the present invention over the mid-dorsum through the hole (about 1.3 cm in diameter) for 0.5 hr. The presence or absence of a skin reaction at the irradiated part of the mouse is observed for 3 days from the irradiation, and the phototoxicity of the compound of the present invention is evaluated. For evaluation, the skin reaction observation results of the 0.5 w/v % methylcellulose solution oral administration group are used as a negative control and those of the lomefloxacin hydrochloride 100 mg/kg oral administration group are used as a positive control.

Experimental Example 5

The effect of the compound of the present invention for stress urinary incontinence can be measured by comparing the leak point pressure before and after the administration of the compound as shown below.

SD female rats (body weight 180-350 g) are anesthetized with urethane (Wako Pure Chemical Industries, Ltd.), and the spinal cord is cut at T8-9 level to eliminate the micturition reflex. During the operation, halothane (Takeda Pharmaceutical Company Limited) anesthesia is added as necessary. The rats are fixed at a dorsal position, and two catheters (PE-100; Clay Adams) are indwelled in the bladder. One of the catheters is filled with saline stained with Evans Blue dye (Merck), and connected to a 50 ml syringe (TERUMO CORPORATION) fixed on an infusion pump (KD Scientific) via a three-way cock. The other catheter is connected to a pressure transducer (DX-100; NIHON KOHDEN CORPORATION), and signals of the transducer are transmitted to computer via an amplifier (blood pressure amplification unit AP-641G; NIHON KOHDEN CORPORATION) and a data analyzer (BIOPAC; MP100), and recorded on a hard disk. The data is analyzed on the computer using a software (BIOPAC; Acq-Knowledge). Saline is injected into the bladder using the infusion pump at a rate of 360 ml/hr, infusion is stopped on the moment fluid leakage from the urethral meatus is observed, and the solution in the bladder is discharged by opening the three-way cock. The maximum intravesical pressure during infusion is taken as a leak point pressure, which is measured repeatedly until the value is stabilized, and the average value of the last three measures is taken as the data. The compound of the present invention is dissolved in DMA/PEG400 (1:1) and intravenously administered at 0.5 mL/kg. The leak point pressure is compared before and after the administration.

Experimental Example 5a

The effect of the compound of the present invention for stress urinary incontinence was measured by comparing the leak point pressure before and after the administration of the compound as shown below.

SD female rats (body weight 200-270 g) were anesthetized with urethane (Wako Pure Chemical Industries, Ltd.), and the spinal cord was cut at T8-9 level to eliminate the micturition reflex. During the operation, isoflurane anesthesia was added as necessary. The rats were fixed at a dorsal position, and two catheters (PE-100; Clay Adams) were indwelled in the bladder. One of the catheters was filled with saline stained with Evans Blue dye (Merck), and connected to a 50 ml syringe (TERUMO CORPORATION) fixed on an infusion pump (KD Scientific) via a three-way cock. The other catheter was connected to a pressure transducer (DX-100; NIHON KOHDEN CORPORATION), and signals of the transducer were transmitted to computer via an amplifier (blood pressure amplification unit AP-641G; NIHON KOHDEN CORPORATION) and a data analyzer (BIOPAC; MP100), and recorded on a hard disk. The data was analyzed on the computer using a software (BIOPAC; AcqKnowledge).

A DMA/PEG400 (1:1) solution was intravenously administered to the rats at 0.5 mL/kg. From 10 min later, saline was injected into the bladder using the infusion pump at a rate of 360 ml/hr, infusion was stopped on the moment fluid leakage from the urethral meatus was observed, and the solution in the bladder was discharged by opening the three-way cock. The maximum intravesical pressure during infusion was taken as a leak point pressure, which was measured repeatedly until the value was stabilized, and the average value of the last three measures was taken as the data. The compounds of Examples 5 and 8 were dissolved in DMA/PEG400 (1:1) and intravenously administered at 0.5 mL/kg, and the leak point pressure was compared before and after the administration. Williams test was used for statistical calculation. The results are shown in Tables 2 and 3.

TABLE 2

| group | dose (mg/kg, i.v.) | n | Change in leak point pressure (cmH$_2$O) |
|---|---|---|---|
| solvent | 0 | 20 | −0.2 ± 0.5 |
| compound of Example 5 | 0.03 | 5 | 5.2 ± 1.7* |
| | 0.1 | 5 | 9.1 ± 1.3* |
| | 0.3 | 5 | 13.6 ± 2.4* |
| | 1 | 5 | 19.6 ± 1.9* |

*P < 0.025, difference from solvent group was tested by comparison (one-side test, Williams test)

TABLE 3

| group | dose (mg/kg, i.v.) | n | Change in leak point pressure (cmH$_2$O) |
|---|---|---|---|
| solvent | 0 | 20 | −0.2 ± 0.5 |
| compound of Example 8 | 0.1 | 5 | 5.4 ± 1.6* |
| | 0.3 | 5 | 10.8 ± 3.3* |
| | 1 | 5 | 17.3 ± 3.4* |
| | 3 | 5 | 23.6 ± 3.3* |

*P < 0.025, difference from solvent group was tested by comparison (one-side test, Williams test)

Experimental Example 6

The effect of the compound of the present invention for obesity can be measured using the food consumption calculated as follows as an index.

Male F344 rats (CLEA Japan, Inc.) are purchased at 5 weeks of age, and raised by groups on a solid high-fat diet with fat content 45 kcal % (D12451, Research Diets). When sufficient obesity is observed (40 to 60-week-old), they are housed individually, and given a powder high-fat diet with fat content 45 kcal % (D12451M, Research Diets) in a feeder. The rats are grouped using body weight and food consumption (18:00-8:00) one day before administration as indices. The compound of the present invention is dissolved in 0.5% methylcellulose solution, and administered by gavage at a dose of 2 mL/kg at 18:00. A 0.5% methylcellulose solution is administered to the control group. After drug administration, a previously weighed feeder is placed in the breeding cage. The feeder is weighed 3, 14 and 24 hr after the administration and the food consumption is calculated (Williams test or t-test).

Experimental Example 6a The effect of the compound of the present invention for obesity was measured using the food consumption calculated as follows as an index.

Male F344 rats (CLEA Japan, Inc.) were purchased at 5 weeks of age, and raised by groups on a solid high-fat diet with fat content 45 kcal % (D12451, Research Diets). When sufficient obesity was observed (40 to 60-week-old), they were raised singly, and given a powder high-fat diet with lipid content 45 kcal % (D12451M, Research Diets) in a feeder. The rats were grouped using body weight and food consumption (18:00-8:00) one day before administration as indices. The compound of Example 5 was dissolved in 0.5% methylcellulose solution at a concentration of 0.5 mg/mL, and administered by gavage at a dose of 2 mL/kg at 18:00. A 0.5% methylcellulose solution was administered to the control group. After administration, a previously-weighed feeder was placed in the breeding cage. The feeder was weighed 24 hr after the administration and the food consumption was calculated. The compound of Example 5 suppressed food consumption by 21.8% as compared to the control group.

Experimental Example 6b

The effect of the compound of the present invention for obesity was measured using high-fat diet-loaded rats based on the effects on body weight and food consumption.

38 to 60-week-old male F344 rats (DIO-F344 rat) raised on a 42 kcal % fat high-fat diet (D12451, Research Diets) from 7 weeks of age were used. They were grouped based on the body weight one day before operation. The compound of Example 8 was dissolved in saline, filled in an osmotic pump (Alzet osmotic pump 2mL2 type), and subcutaneously implanted under isoflurane anesthesia. The body weight was measured on completion of the operation, and measured again at 14 days postoperation. In addition, the amount of remaining food was measured, and food consumption for 14 days was measured. For statistical calculation, Williams test was used. The results are shown in Table 4.

TABLE 4

| group | dose (mg/kg/day) | n | body weight loss (%) | food consumption/ 14 days (g) |
|---|---|---|---|---|
| solvent | 0 | 10 | 3.5 ± 0.6 | 155 ± 5 |
| compound of Example 8 | 3 | 10 | 4.8 ± 0.5 | 150 ± 7 |
| | 10 | 10 | 4.9 ± 0.3 | 140 ± 6 |
| | 30 | 10 | 7.5 ± 0.3* | 110 ± 2* |

*P < 0.025, difference from solvent group was tested by comparison (one-side test, Williams test).

Experimental Example 7

The effect of the compound of the present invention for organ prolapse can be measured by examining the enhancement of urethral closure response by pelvic floor muscles (iliococcygeal muscle, pubococcygeal muscle etc.) induced by an increased intravesical pressure, by compound administration.

Female SD rats (body weight 200-310 g) are anesthetized with urethane (Wako Pure Chemical Industries, Ltd.), and the spinal cord is transected at T8-9 level to eliminate the micturition reflex. During the operation, halothane (Takeda Pharmaceutical Company Limited) anesthesia is added when necessary. After abdominal section, bladder neck is ligated with a suture thread, and then the hypogastric nerve and pudendal nerve are bilaterally transected. A catheter (PE-90, Clay Adams) is placed in the bladder, and the other end of the bladder catheter is connected to a pressure transducer and a water reservoir (60 ml syringe) of saline via a three-way cock. A microtip transducer catheter (SPR-524, Millar Instruments Inc.) is inserted toward the bladder from the urethral orifice, and adjusted using a scale on the catheter surface so that the transducer part is positioned in the urethra at 10.0-15.0 mm from the urethral orifice.

The changes in the topical pressure within the urethra (hereinafter conveniently indicated as urethral pressure) as measured by the microtip transducer is transmitted to a computer via an amplifier (blood pressure amplification unit AP-641G; NIHON KOHDEN) and a data analyzer (MP-100; biopack; sampled at 500 Hz), and recorded on a hard disc. The intravesical pressure is rapidly increased to 50 cmH$_2$O for 30 sec by setting the position of the water reservoir of saline at 50 cm higher, and changes in the urethral pressure are observed. The reaction of the urethra induced by an increased intravesical pressure is measured 3 times, and the average of the last 2 measures is taken as the value before drug administration. The evaluation item is reflex urethral closure response, and the recorded values are subjected to smoothing process at 500 points to calculate an average urethral pressure per 1 sec, after which the value immediately before increase in the intravesical pressure is subtracted from the maximum value on increase in the intravesical pressure and taken as the urethral closure response. After measurement of the value before drug administration, the compound of the present invention is dissolved in N,N-dimethylformamide/polyethylene glycol 400 (1:1) and administered intravenously at a rate of 0.5 ml/kg, and the urethral closure response is evaluated again 10 min later.

Experimental Example 7a

The effect of the compound of the present invention for organ prolapse was measured by examining the enhancement of urethral closure response by pelvic floor muscles (iliococcygeal muscle, pubococcygeal muscle etc.) induced by an increased intravesical pressure, by compound administration.

The enhancing action of the compound on urethral closure response induced by an increased intravesical pressure was measured using female spinal cord-transected rats with bilaterally transected hypogastric nerve and pudendal nerve.

SD female rats (body weight 246-298 g) were anesthetized with urethane, and the spinal cord was cut at T8-9 level to eliminate the micturition reflex. During the operation, isoflurane anesthesia was added as necessary. After abdominal section, bladder neck was ligated with a suture thread, and then the hypogastric nerve and pudendal nerve were bilaterally transected. A catheter was placed in the bladder, and the other end of the bladder catheter was connected to a pressure transducer and a water reservoir (60 ml syringe) of saline via a three-way cock. A microtip transducer catheter (SPR-524, Millar Instruments Inc.) was inserted toward the bladder from the urethral orifice, and adjusted using a scale on the catheter surface so that the transducer part is positioned in the urethra at 10.0-15.0 mm from the urethral orifice. The changes in the topical pressure within the urethra (hereinafter conveniently indicated as urethral pressure) as measured by the microtip transducer was transmitted to a computer via an amplifier and a data intake device, and recorded on a hard disc.

The intravesical pressure was rapidly increased to 50 cmH$_2$O for 30 sec by setting the position of the water reservoir of saline at 50 cm higher, and changes in the urethral pressure were observed. The reaction of the urethra induced by an increased intravesical pressure was measured repeatedly until the value is stabilized, and the average of the last 2 measures was taken as the value before drug administration. The evaluation item was reflex urethral closure response, and an average urethral pressure upon intravesical pressure increase was calculated, after which the value immediately before increase in the intravesical pressure was subtracted and taken as the urethral closure response.

After measurement of the value before drug administration, the compounds of Examples 5 and 8 were dissolved in saline and administered intravenously at a rate of 1.0 ml/kg, and the urethral closure response was evaluated again 10 min later.

The changes in the urethral closure response of the present compound administration group and the saline administration group from the values before drug administration are shown in Table 5.

TABLE 5

| group | dose (mg/kg, i.v.) | n | urethral closure respons (ratio relative to value before administration) |
|---|---|---|---|
| saline | 0 | 4 | 94.5 ± 9.4 |
| compound of Example 5 | 1 | 3 | 227 ± 32** |
| compound of Example 8 | 1 | 4 | 192 ± 13** |

**$P < 0.01$, (two-side test, Dunnett-test)

INDUSTRIAL APPLICABILITY

Since the present compound has a superior serotonin 5-HT$_{2C}$ receptor activating action, they are useful as drugs for the prophylaxis or treatment of any serotonin 5-HT$_{2C}$-related diseases, for example, lower urinary tract symptom, obesity and/or organ prolapse and the like.

This application is based on a patent application No. 2009-142673 filed in Japan, the contents of which are incorporated in full herein.

The invention claimed is:

1. 3-(3-Methylmorpholin-4-yl)-6,7,8,9-tetrahydropyrazino[2,3-f][1,4]oxazepine or a salt thereof.

2. A pharmaceutical composition comprising 3-(3-Methylmorpholin-4-yl)-6,7,8,9-tetrahydropyrazino[2,3-f][1,4]oxazepine or a salt thereof and a pharmacologically acceptable carrier.

* * * * *